US008592465B2

(12) United States Patent
Miller et al.

(10) Patent No.: US 8,592,465 B2
(45) Date of Patent: Nov. 26, 2013

(54) COMPOUNDS FOR TREATMENT OF CANCER

(75) Inventors: Duane D. Miller, Germantown, TN (US); Wei Li, Germantown, TN (US); Zhao Wang, Memphis, TN (US); Yan Lu, Bartlett, TN (US); Jianjun Chen, Memphis, TN (US); James T. Dalton, Columbus, OH (US); Chien-Ming Li, Memphis, TN (US)

(73) Assignees: University of Tennessee Research Foundation, Columbus, OH (US); The Ohio State University Research Foundation, Knoxville, TN (US)

( * ) Notice: Subject to any disclaimer, the term of this patent is extended or adjusted under 35 U.S.C. 154(b) by 385 days.

(21) Appl. No.: 12/485,881

(22) Filed: Jun. 16, 2009

(65) Prior Publication Data
US 2009/0326020 A1 Dec. 31, 2009

Related U.S. Application Data

(60) Provisional application No. 61/061,875, filed on Jun. 16, 2008.

(51) Int. Cl.
C07D 277/04 (2006.01)
C07D 277/24 (2006.01)
A61K 31/426 (2006.01)

(52) U.S. Cl.
USPC ............ 514/365; 548/200; 548/203; 548/146

(58) Field of Classification Search
None
See application file for complete search history.

(56) References Cited

U.S. PATENT DOCUMENTS

| | | | | |
|---|---|---|---|---|
| 4,987,132 A | * | 1/1991 | Mase et al. | 514/253.1 |
| 6,080,764 A | * | 6/2000 | Chihiro et al. | 514/342 |
| 7,307,093 B2 | | 12/2007 | Miller et al. | |
| 2003/0144329 A1 | | 7/2003 | Pfahl et al. | |
| 2003/0225102 A1 | | 12/2003 | Sankaranarayanan | |
| 2004/0267017 A1 | * | 12/2004 | Bierer et al. | 544/370 |
| 2005/0131014 A1 | | 6/2005 | Collini et al. | |
| 2005/0256170 A1 | * | 11/2005 | Oxford et al. | 514/341 |
| 2006/0014740 A1 | | 1/2006 | Miller et al. | |
| 2006/0040998 A1 | | 2/2006 | Miller et al. | |
| 2006/0041006 A1 | * | 2/2006 | Ibrahim et al. | 514/422 |
| 2006/0211603 A1 | * | 9/2006 | Raju et al. | 514/8 |
| 2007/0155807 A1 | | 7/2007 | Miller et al. | |
| 2007/0167622 A1 | | 7/2007 | Gillespie et al. | |
| 2008/0255213 A1 | | 10/2008 | Miller et al. | |
| 2009/0143446 A1 | | 6/2009 | Miller et al. | |

FOREIGN PATENT DOCUMENTS

| | | |
|---|---|---|
| EP | 0 279 681 A2 | 8/1988 |
| EP | 0499987 A1 | 8/1992 |
| EP | 0513387 | 11/1992 |
| EP | 549 364 | 6/1993 |
| EP | 535 906 | 6/2005 |
| EP | 1 637 529 | 3/2006 |
| EP | 1 832 585 | 9/2007 |
| EP | 1 834 954 | 9/2007 |
| EP | 2 050 749 | 4/2009 |
| EP | 2 065 369 | 6/2009 |
| RU | 2139283 C1 | 10/1999 |
| RU | 97114846 A | 11/1999 |
| WO | WO 01/17992 | 3/2001 |
| WO | WO 02/085899 | 10/2002 |
| WO | WO 03/027076 | 4/2003 |
| WO | WO 03/027085 A2 | 4/2003 |
| WO | WO 03/037332 | 5/2003 |
| WO | WO 03/090680 | 11/2003 |
| WO | WO 2005/000940 | 1/2005 |
| WO | WO 2005/009940 A1 | 2/2005 |
| WO | 2005049591 A1 | 6/2005 |
| WO | WO 2005/086902 | 9/2005 |
| WO | WO 2006/063585 | 6/2006 |
| WO | WO 2006/076706 | 7/2006 |
| WO | WO 2006/078287 | 7/2006 |
| WO | WO 2006/127587 | 11/2006 |
| WO | WO 2007/016979 | 2/2007 |

(Continued)

OTHER PUBLICATIONS

Byrn et al. Solid-State Chemistry of Drugs, 2d, Chapter 11:Hydrates and Solvates, 233 247 (1999).*
Morissette et al., Adv. Drug Delivery Rev. 2004, 56, 275-300.*
Rouhi, A.M. Chem. & Eng. News, Feb. 24, 2003, 81(8), 32-35.*
Aitken, et al., J. Chem. Res. 2:76 (1998).*
STN Search Report: Pavlova et al Khimiko-Farmatsevticheskii Zhurnal, 20(9), 1083-1088 (1986) (abstract only).
Holmes et al., "Reagents for Combinatorial Organic Synthesis: Development of a New o-Nitrobenzyl Photolabile Linker for Solid Phase Syntheses," J. Org. Chem. 60:2318-2319 (1995).

(Continued)

*Primary Examiner* — Michael Barker
(74) *Attorney, Agent, or Firm* — Pearl Cohen Zedek Latzer Baratz, LLP; Mark S. Cohen

(57) ABSTRACT

Compounds according to formula (I) are disclosed

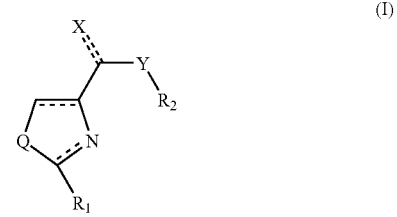

(I)

where Q is S, N, or O; X is optional, and can be O═, S═, ═N—NH$_2$, ═N—OH, or —OH; Y is optional and can be —N(H)—, O, or C$_1$ to C$_{20}$ hydrocarbon; and R$_1$ and R$_2$ are each independently substituted or unsubstituted single-, fused- or multiple-ring aryl or (hetero)cyclic ring systems. Methods of making these compounds, pharmaceutical compositions containing the compounds, and their use, particularly for treating or preventing cancer, are also disclosed.

32 Claims, 5 Drawing Sheets

(56) References Cited

FOREIGN PATENT DOCUMENTS

| | | |
|---|---|---|
| WO | WO 2007/058338 | 5/2007 |
| WO | WO 2007/104558 | 9/2007 |
| WO | WO 2007/115805 | 10/2007 |
| WO | WO 2008/006873 | 1/2008 |
| WO | WO 2008019357 A2 * | 2/2008 |
| WO | 2008036067 A2 | 3/2008 |
| WO | WO 2008/030448 | 3/2008 |
| WO | WO 2008/038955 | 4/2008 |
| WO | WO 2008/079277 | 7/2008 |
| WO | 2008128179 A1 | 10/2008 |
| WO | 2009070645 A1 | 6/2009 |

OTHER PUBLICATIONS

Chen et al., "Synthesis and Antiproliferative Activity of Imidazole and Imidazoline Analogs for Melanoma," Bioorg. Med. Chem. Lett. 18(11):3183-3187 (2008).
Lu et al., "Discovery of 4-Substituted Methoxybenzoyl-aryl-thiazole as Novel Anticancer Agents: Synthesis, Biological Evaluation, and Structure-Activity Relationships," J. Med. Chem. 52:1701-1711 (2009).
Li et al., "Synthesis and Antiproliferative Activity of Thiazolidine Analogs for Melanoma," Bioorg. Med. Chem. Lett. 17:4113-4117 (2007).
Gududuru et al., "Discovery of 2-Arylthiazolidine-4-Carboxylic Acid Amides as a New Class of Cytotoxic Agents for Prostate Cancer," J. Med. Chem. 48:2584-2588 (2005).
Gududuru et al., "SAR Studies of 2-Arylthiazolidine-4-Carboxylic Acid Amides: A Novel Class of Cytotoxic Agents for Prostate Cancer," Bioorg. Med. Chem. Lett. 15:4010-4013 (2005).
Gududuru et al., "Synthesis and Antiproliferactive Activity of 2-Aryl-4-Oxo-Thiazolidin-3-Yl-Amides for Prostate Cancer," Bioorg. Med. Chem. Lett. 14:5289-5293 (2004).
Li et al., "Structure-Activity Relationship Studies of Arythiazolidine Amides as Selective Cytotoxic Agents for Melanoma," Anticancer Research 27:883-888 (2007).
Supplementary Partial Search Report for European Patent Application No. EP 09 83 5407 dated Feb. 9, 2012.
International Search Report for International Application No. PCT/US09/47572 dated Jun. 9, 2010.
Mahboobi et al., Synthesis of Naturally Occurring Pyrazine and Imidazole Alkaloids from *Botryllus leachi*, Monatshefte Fuer Chemie, vol. 135, No. 3, 2004, pp. 333-342.
Tucker et al., Structure-Activity Relationships of Acyloxyamidine Cytomegalovirus DNA Polymerase Inhibitors, Bioorganic & Medical Chemistry, vol. 8, No. 3, 2000, pp. 601-615.
Sheppard et al., 3-(2-(3-Pyridinyl) thiazolidin-4-oyl) indoles, a Novel Series of Platelet Activating Factor Antagonists, Journal of Medicinal Chemistry, vol. 37, No. 13, 1997.
Giordano et al., New Strategy for Racemization of 2-Amino-1, 3-propanediols, Key Intermediates for the Synthesis of Antibiotic Drugs, Tetrahedron Letters, vol. 29, No. 43, 1988, pp. 5561-5564.
Stenhagen et al. Studies of Hydrocarbons Structurally Related to Phthiocerol, Journal Biological Chemistry, 1950, vol. 183, pp. 223-229; p. 224.
Roy et al., Thiazole and Oxazole Peptides: biosynthesis and molecular machinery, Natural Product Reports, 1999, vol. 16, pp. 249-263; p. 249 scheme1.
Lu et al., Synthesis and Biological Evaluation of 2-Arylthiazolidine-4-Caboxylic Acid Amides for Melanoma and Prostate Cancer, Abstracts of Papers, 234th ACS National Meeting, Boston, MA, United Staes, Aug. 19-23, 2007, MEDI-304.
Raj et al., Guanosine Phosphate Binding Protein Coupled Receptors in Prostate Cancer: A Review, J. Urol., 2002, vol. 167, pp. 1458-1463.
Kue et al., Essential Role for G Proteins in Prostate Cancer Cell Growth and Signaling, J. Urol., 2002, vol. 164, pp. 2162-2167.
Guo et al., Expression and Function of Lysophosphatidic Acid LPA1 Receptor in Prostate Cancer Cells, Endocrinology, 2006, vol. 147, pp.. 4883-4892.
Qi et al., Lysophosphatidic Acid Stimulates Phospholipase D Activity and Cell Proliferation in PC-3 Human Prostate Cancer Cells, J. Cell, Physiol, 1998, vol. 174, pp. 261-272.
Jesberger et al., Synthesis, 2003, 1929-1958.
Riedrich et al., "Peptide-embedded heterocycles by mild single and multiple Aza-Wittig ring closures" Angewandte Chemie, International Edition, 2007, vol. 46(15), ,pp. 2701-2703.
Bergeron et al., "Partition-variant desferrithiocin analogues: organ targeting and increased iron clearance" J. Med. Chem, vol. 48, pp. 821-831.
Hsu et al., Optically active derivatives of imidazolines. alpha-Adrenergic blocking properties J. Med. Chem., 1980, vol. 23(11), pp. 1232-1235.
Meyer et al., Tetrahedron: Asymmetry, 2003, vol. 14, pp. 2229-2238.
Deswal, S. et al.: 'Quantitative structure activity relationship studies of aryl heterocycle-based thrombin inhibitors' European Journal of Medicinal Chemistry vol. 41, 2006, pp. 1339-1346, XP024993923.
Staas, D.D.: 'Discovery of potent, selective 4-fluoroproline-based thrombin inhibitors with improved metabolic stability' Biorganic & Medicinal Chemistry vol. 14, 2006, pp. 6900-6916, XP025133602.
Young, M.B. et al: 'Discovery and Evaluation of potent P1 Aryl Heterocycle-Based Thrombin Inhibitors' Journal of Medicinal Chemistry vol. 47, No. 12, 2004, pp. 2995-3008, XP003026047.
Lange, U.E.W. et al: 'Orally active thrombin inhibitors. Part 2: Optimization of the P2-moiety' Bioorganic & Medicinal Chemistry Letters vol. 16, 2006, pp. 2648-2653, XP025106813.
Bergeron, "Evaluation of Desferrethiocin and its synthetic analogs as orally effective iron chelators", J. Med. Chem. 34:2072-8, 1991.
Bergeron et al., "Desazadesmethyldesferrethiocin analogues as orally effective iron chelators", J. Med. Chem. 42:95-108, 1999.
Zamri et al., "An improved stereocontrolled synthesis of pyochelin, siderophore of *Pseudomonas aeruginosa* and *Burkholderia cepacia*", Tetrahedron 56:249-256, 2000.
Nahm et al., "N-methoxy-N-methylamides as effective acylating agents", Tetrahedron Letters, 22:3815-3818, 1981.
Anderson et al., "Design, synthesis, antineoplastic activity, and chemical properties of bis(carbamate) derivatives of 4,5-bis(hydroxymethyl)imidazole" J. Med. Chem. 32(1), 119-127, 1989.
Williams et al., "Studies of mild dehydrogenations in heterocyclic systems", Tetrahedron Letters, 38:331-334, 1997.
Rubinstein et al., "Comparison of in vitro anticancer drug-screening data generated with a tetrazolium assay versus a protein assay against a diverse panel of human tumor cell lines", J. Natl. Cancer Inst. 82:1113-1118, 1990.
Dothager et al., "Synthesis and identification of small molecules that potently induce apoptosis in melanoma cells through G1 cell cycle arrest", J. Am. Chem. Soc. 127:8686-8696, 2005.
Margolis et al., "Addition of colchicine-tubulin complex to microtubule ends: the mechanism of substroichiometric colchicine poisoning", Proc. Natl. Acad. Sci. 74:3466-3470, 1977.

* cited by examiner

COMPOUNDS FOR TREATMENT OF CANCER

This application claims the benefit of U.S. Provisional Patent Application Ser. No. 61/061,875, filed Jun. 16, 2008, which is hereby incorporated by reference in its entirety.

This invention was made with funding received from the U.S. Department of Defense under grant DAMD 17-01-1-0830, the U.S. Public Heath Service under grant CA-125623, and the National Institutes of Health under Core Grant 21765. The U.S. government has certain rights in this invention.

FIELD OF THE INVENTION

The present invention relates to novel compounds having anti-cancer activity, methods of making these compounds, and their use for treating various forms of cancer.

BACKGROUND OF THE INVENTION

Cancer is the second most common cause of death in the United States, exceeded only by heart disease. In the United States, cancer accounts for 1 of every 4 deaths. The 5-year relative survival rate for all cancers patients diagnosed in 1996-2003 is 66%, up from 50% in 1975-1977 (*Cancer Facts & Figures* American Cancer Society: Atlanta, Ga. (2008)). This improvement in survival reflects progress in diagnosing at an earlier stage and improvements in treatment. Discovering highly effective anticancer agents with low toxicity is a primary goal of cancer research.

2-aryl-thiazolidine-4-carboxylic acid amides have been described as potent cytotoxic agents for both prostate cancer and melanoma (Li et al., "Synthesis and Antiproliferative Activity of Thiazolidine Analogs for Melanoma," *Bioorg. Med. Chem. Lett.* 17:4113-7 (2007); Li et al., "Structure-Activity Relationship Studies of Arylthiazolidine Amides as Selective Cytotoxic Agents for Melanoma," *Anticancer Res.* 27:883-888 (2007); Lu et al., "Synthesis and Biological Evaluation of 2-Arylthiazolidine-4-Carboxylic Acid Amides for Melanoma and Prostate Cancer," *Abstracts of Papers, 234th ACS National Meeting, Boston, Mass., United States, Aug.* 19-23, 2007, MEDI-304; Gududuru et al., "SAR Studies of 2-Arylthiazolidine-4-Carboxylic Acid Amides: A Novel Class of Cytotoxic Agents for Prostate Cancer," *Bioorg. Med. Chem. Lett.* 15:4010-4013 (2005); Gududuru et al., "Discovery of 2-Arylthiazolidine-4-Carboxylic Acid Amides as a New Class of Cytotoxic Agents for Prostate Cancer," *J. Med. Chem.* 48:2584-2588 (2005)). These 2-aryl-thiazolidine-4-carboxylic acid amides were designed from lysophosphatidic acid (LPA) structure with a lipid chain. This design choice was directed toward inhibition of GPCR (guanine-binding protein-coupled receptor) signaling, which is involved in proliferation and survival of prostate cancer (Raj et al., "Guanosine Phosphate Binding Protein Coupled Receptors in Prostate Cancer: A Review," *J. Urol.* 167:1458-1463 (2002); Kue et al., "Essential Role for G Proteins in Prostate Cancer Cell Growth and Signaling," *J. Urol.* 164:2162-7 (2000); Guo et al., "Expression and Function of Lysophosphatidic Acid LPA1 Receptor in Prostate Cancer Cells," *Endocrinology* 147:4883-4892 (2006); Qi et al., "Lysophosphatidic Acid Stimulates Phospholipase D Activity and Cell Proliferation in PC-3 Human Prostate Cancer Cells," *J. Cell. Physiol.* 174: 261-272 (1998)).

The most potent of the 2-aryl-thiazolidine-4-carboxylic acid amides could inhibit prostate cancer cells with an average $IC_{50}$ in the range from 0.7 to 1.0 μM and average $IC_{50}$ values against melanoma cells were 1.8~2.6 μM (Li et al., "Synthesis and Antiproliferative Activity of Thiazolidine Analogs for Melanoma," *Bioorg. Med. Chem. Lett,* 17:4113-7 (2007)). One preferred compound, (2RS,4R)-2-phenyl-thiazolidine-4-carboxylic acid hexadecylamide, was sent to the United States National Cancer Institute 60 human tumor cell line anticancer drug screen (NCI-60). Results from NCI-60 assay showed that this compound could inhibit growth of all nine types of cancer cells with $IC_{50}$ values in the range from 0.124 μM (Leukemia, CCRF-CEM) to 3.81 μM (Non-Small Cell Lung Cancer, NCI-H522). Further improvement in anticancer activity of these compounds, in terms of their $IC_{50}$ values, would be desirable.

The present invention is directed to overcoming these and other deficiencies in the prior art.

SUMMARY OF THE INVENTION

A first aspect of the present invention relates to compounds according to formula (I)

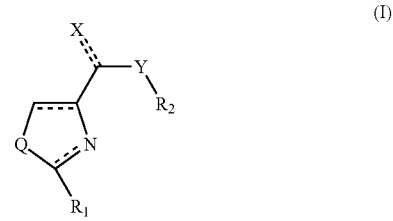

wherein
  Q is S, N, or O;
  X is optional, and can be O=, S=, =N—NH$_2$, =N—OH, or —OH;
  Y is optional and can be —N(H)—, O, or $C_1$ to $C_{20}$ hydrocarbon;
  $R_1$ and $R_2$ are each independently substituted or unsubstituted single-, fused- or multiple-ring aryl or heterocyclic ring systems, including saturated and unsaturated N-heterocycles, saturated and unsaturated S-heterocycles, and saturated and unsaturated O-heterocycles, saturated or unsaturated cyclic hydrocarbons, saturated or unsaturated mixed heterocycles, and aliphatic straight- or branched-chain $C_1$ to $C_{30}$ hydrocarbons. Compounds can be provided in the form of their pharmaceutically acceptable salts, hydrates, or prodrugs thereof.

A second aspect of the present invention relates to a pharmaceutical composition including a pharmaceutically acceptable carrier and a compound according to the first aspect of the present invention.

A third aspect of the present invention relates to a method of treating cancer that includes selecting a subject in need of treatment for cancer, and administering to the subject a pharmaceutical composition comprising a compound according to the first aspect of the present invention under conditions effective to treat cancer.

A fourth aspect of the present invention relates to a method of destroying a cancerous cell that includes: providing a compound of the present invention and then contacting a cancerous cell with the compound under conditions effective to destroy the contacted cancerous cell.

A fifth aspect of the present invention relates to methods of making a compound according to formula (I).

According to one embodiment, the method includes the step of reacting intermediate

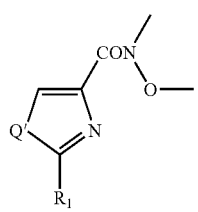

with either a Grignard reagent containing R² or Br—R² under conditions effective to form a compound according to formula (I) having a methanone linker group, where R¹ and R² are defined as for formula (I) and Q' is the same as Q except that Q' includes a protecting group when Q is N, and optionally deprotecting the compound when Q is N. Conversion of the methanone linker group into a hydrazono linker group, methanone oxime linker group, and a methylene linker are also encompassed by the present invention.

According to another preferred embodiment, the method includes the step of reacting intermediate

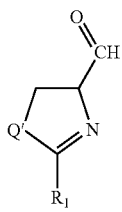

with a Grignard reagent containing R² under conditions effective to form a compound according to formula (I) having a —CH(OH)— linker group, where R¹ and R² are defined as in formula (I) and Q' is the same as Q except that Q' includes a protecting group when Q is N, and optionally deprotecting the compound when Q is N. Dehydrogenation to form a thiazole, oxazole, or imidazole central ring is also contemplated.

According to another preferred embodiment, the method includes reacting an intermediate

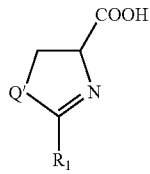

with Br—R² under conditions effective to form a compound according to formula (I) having an ester or amide linker group, where R¹ and R² are defined as in formula (I) and Q' is the same as Q except that Q' includes a protecting group when Q is N, and optionally deprotecting the compound when Q is N. Dehydrogenation to form a thiazole, oxazole, or imidazole central ring is also contemplated.

The present invention affords a new class of compounds that possess improved potency and selectivity (as compared to prior fatty acid thiazolidine carboxamides) during in vitro studies against several different cancer cells lines, including prostate and melanoma cancer cells. Using one preferred member of this class, it is also demonstrated in the accompanying examples that these compounds are inhibitors of tubulin polymerization. One of these compounds is demonstrated to possess significant anti-cancer activity during in vivo xenograft studies of melanoma in mice. Based on these data, and the demonstration of their mode of action, it is believed that the compounds of the present invention have significant activity against a number of forms of cancer.

BRIEF DESCRIPTION OF THE DRAWINGS

FIG. 3A illustrate the effect of various dosages (10 nM, 50 nM, 200 nM, and 500 nM) of compound 8f relative to control. Amounts in excess of the $IC_{50}$ value illustrate a significant change in cell cycle distribution. FIG. 3B graphically illustrates the change in G2/M versus G1 cell cycle distribution.

DETAILED DESCRIPTION OF THE INVENTION

Figure 1:
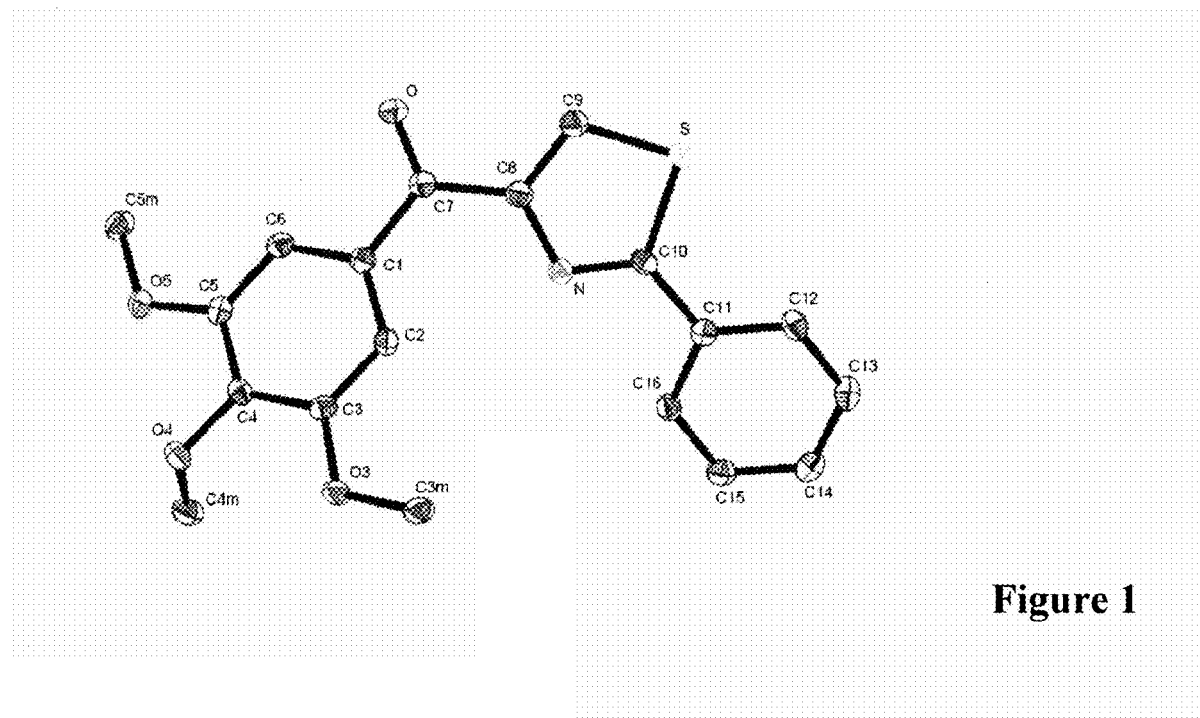
FIG. 1 is ORTEP drawing of compound 8f with thermal ellipsoids depicted at 50% probability level. The drawing was generated following X-ray crystallography studies.

One aspect of the present invention relates to compounds according to formula (I)

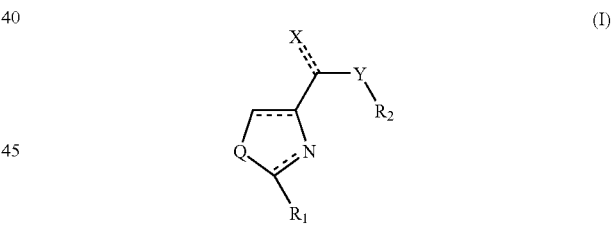

wherein
Q is S, N, or O;
X is optional, and can be S=, O=, =N—NH₂, =N—OH, or —OH;
Y is optional and can be —N(H)—, O, or $C_1$ to $C_{20}$ hydrocarbon; and
$R_1$ and $R_2$ are each independently substituted or unsubstituted single-, fused- or multiple-ring aryl or (hetero)cyclic ring systems, including saturated and unsaturated N-heterocycles, saturated and unsaturated S-heterocycles, and saturated and unsaturated O-heterocycles, saturated or unsaturated cyclic hydrocarbons, saturated or unsaturated mixed heterocycles, aliphatic straight- or branched-chain $C_1$ to $C_{30}$ hydrocarbons.

As used herein, "saturated or unsaturated cyclic hydrocarbons" can be any such cyclic hydrocarbon, including but not limited to phenyl, biphenyl, triphenyl, naphthyl, cycloalkyl, cycloalkenyl, cyclodienyl, fluorene, adamantane, etc.; "saturated or unsaturated N-heterocycles" can be any such N-containing heterocycle, including but not limited to aza- and diaza-cycloalkyls such as aziridinyl, azetidinyl, diazatidinyl, pyrrolidinyl, pipedidinyl, piperazinyl, and azocanyl, pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzimidazolyl, indazolyl, quinolizinyl, cinnolinyl, quinalolinyl, phthalazinyl, naphthyridinyl, quinoxalinyl, etc.; "saturated or unsaturated O-heterocycles" can be any such O-containing heterocycle including but not limited to oxiranyl, oxetanyl, tetrahydrofuranyl, tetrahydropyranyl, dioxanyl, furanyl, pyrylium, benzofuranyl, benzodioxolyl, etc.; "saturated or unsaturated S-heterocycles" can be any such S-containing heterocycle, including but not limited to thiranyl, thietanyl, tetrahydrothiophene-yl, dithiolanyl, tetrahydrothiopyranyl, thiophene-yl, thiepinyl, thianaphthenyl, etc.; "saturated or unsaturated mixed heterocycles" can be any heterocycle containing two or more S-, N-, or O-heteroatoms, including but not limited to oxathiolanyl, morpholinyl, thioxanyl, thiazolyl, isothiazolyl, thiadiazolyl, oxazolyl, isoxazolyl, oxadiaziolyl, etc.

As noted above, the $R^1$ and $R^2$ groups can be substituted or unsubstituted. Thus, although the exemplary groups recited in the preceding paragraph are unsubstituted, it should be appreciated by those of skill in the art that these groups can be substituted by one or more, two or more, three or more, and even up to five substituents (other than hydrogen). Preferred $R^1$ and $R^2$ groups can be generically represented by the following structures:

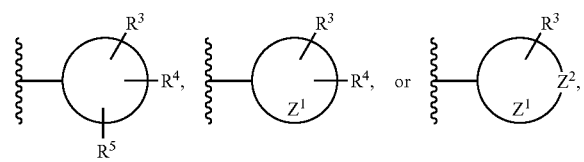

where $Z^1$ and $Z^2$ represent the one or more S-, N-, or O-heteroatoms present in the cyclic structure, and the rings are five- or six-member rings. In one embodiment, the $R^1$ and $R^2$ groups can have the structure:

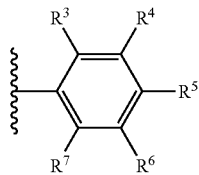

The substituents of these cyclic members (e.g., $R^3$, $R^4$, $R^5$, $R^6$, $R^7$) are independently selected from the group of hydrogen (e.g., no substitution at a particular position), hydroxyl, an aliphatic straight- or branched-chain $C_1$ to $C_{10}$ hydrocarbon, alkoxy, aryloxy, nitro, cyano, halo (e.g., chloro, fluoro, bromo, or iodo), haloalkyl, dihaloalkyl, trihaloalkyl, amino, alkylamino, mesylamino, dialkylamino arylamino, amido, urea, alkyl-urea, alkylamido (e.g., acetamide), haloalkylamido, arylamido, aryl, and $C_5$ to $C_7$ cycloalkyl, arylalkyl, and combinations thereof. Single substituents can be present at the ortho, meta, or para positions. When two or more substituents are present, one of them is preferably, though not necessarily, at the para position.

As used herein, "aliphatic straight- or branched-chain hydrocarbon" refers to both alkylene groups that contain a single carbon and up to a defined upper limit, as well as alkenyl groups and alkynyl groups that contain two carbons up to the upper limit, whether the carbons are present in a single chain or a branched chain. Unless specifically identified, a hydrocarbon can include up to about 30 carbons, or up to about 20 hydrocarbons, or up to about 10 hydrocarbons. Alkenyl and alkynyl groups can be mono-unsaturated or polyunsaturated.

As used herein, the term "alkyl" can be any straight- or branched-chain alkyl group containing up to about 30 carbons unless otherwise specified. The alkyl group can be a sole substituent or it can be a component of a larger substituent, such as in an alkoxy, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, etc.

As used herein, the term "aryl" refers to any aromatic ring substituent that is directly bonded to the $R^1$ or $R^2$ ring member(s). The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc.

Preferred $R^1$ and $R^2$ groups include substituted (with $R^3$-$R^7$ as defined above) and unsubstituted furanyl, indolyl, pyridinyl, phenyl, biphenyl, triphenyl, diphenylmethane, adamantane-yl, fluorene-yl, and other heterocyclic analogs such as those identified above (e.g., pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzimidazolyl, indazolyl, quinolizinyl, cinnolinyl, quinalolinyl, phthalazinyl, naphthyridinyl, quinoxalinyl, oxiranyl, oxetanyl, tetrahydrofuranyl, tetrahydropyranyl, dioxanyl, furanyl, pyrylium, benzofuranyl, benzodioxolyl, thiranyl, thietanyl, tetrahydrothiophene-yl, dithiolanyl, tetrahydrothiopyranyl, thiophene-yl, thiepinyl, thianaphthenyl, oxathiolanyl, morpholinyl, thioxanyl, thiazolyl, isothiazolyl, thiadiazolyl, oxazolyl, isoxazolyl, oxadiaziolyl).

The most preferred $R^2$ group is 3,4,5-trimethoxyphenyl, and the most preferred $R^1$ groups include substituted and unsubstituted phenyl, substituted and unsubstituted thiophene-yl, and substituted and unsubstituted indolyl groups. The preferred substituents of these preferred $R^1$ groups are methyl, ethyl, fluoro, bromo, cyano, nitro, trifluoro, and amino.

In certain embodiments, the compound of formula (I) is

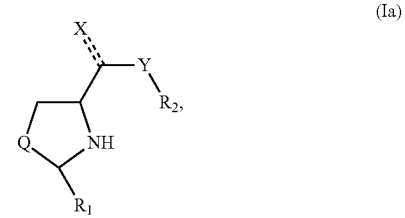

(Ia)

-continued (Ib)

(Ic)

Depending on the definition of Q, therefore, the compounds of the present invention include thiazoles, dihydro-thiazoles, thiazolidines, oxazoles, dihydro-oxazoles, oxazolidines, imidazoles, dihydro-imidazoles, and imidazolidines.

According to a preferred embodiment, the class of compounds has a structure according to formula (II):

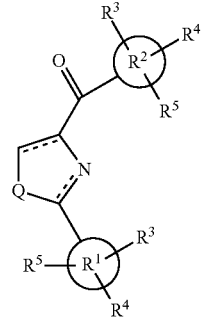

(II)

where X is O=, Y is omitted, and Q and $R^1$-$R^5$ are defined as above for formula (I).

Exemplary compounds of formula (II) include, without limitation: phenyl(2-phenylthiazol-4-yl)methanone (compound 8a); phenyl(2-phenylthiazolidin-4-yl)methanone; phenyl(2-phenyloxazolidin-4-yl)methanone; (4,5-dihydro-2-phenyloxazol-4-yl)(phenyl)methanone; phenyl(2-phenyloxazol-4-yl)methanone; (4-methoxyphenyl)(2-phenylthiazol-4-yl)methanone (compound 8b); (4-methoxyphenyl)(2-phenylthiazolidin-4-yl)methanone; (4,5-dihydro-2-phenylthiazol-4-yl)(4-methoxyphenyl)methanone; (4-methoxyphenyl)(2-phenyloxazol-4-yl)methanone; (4-methoxyphenyl)(2-phenyloxazolidin-4-yl)methanone; (4,5-dihydro-2-phenyloxazol-4-yl)(4-methoxyphenyl)methanone; (4-methoxyphenyl)(2-phenyl-1H-imidazol-4-yl)methanone; (4-methoxyphenyl)(2-phenylimidazolidin-4-yl)methanone; (4,5-dihydro-2-phenyl-1H-imidazol-4-yl)(4-methoxyphenyl)methanone; (3-methoxyphenyl)(2-phenylthiazol-4-yl)methanone (compound 8c); (3-methoxyphenyl)(2-phenylthiazolidin-4-yl)methanone; (4,5-dihydro-2-phenylthiazol-4-yl)(3-methoxyphenyl)methanone; (3-methoxyphenyl)(2-phenyloxazol-4-yl)methanone; (3-methoxyphenyl)(2-phenyloxazolidin-4-yl)methanone; (4,5-dihydro-2-phenyloxazol-4-yl)(3-methoxyphenyl)methanone; (3-methoxyphenyl)(2-phenyl-1H-imidazol-4-yl)methanone; (3-methoxyphenyl)(2-phenylimidazolidin-4-yl)methanone; (4,5-dihydro-2-phenyl-1H-imidazol-4-yl)(3-methoxyphenyl)methanone; (2-methoxyphenyl)(2-phenylthiazol-4-yl)methanone (compound 8d); (2-methoxyphenyl)(2-phenylthiazolidin-4-yl)methanone; (4,5-dihydro-2-phenylthiazol-4-yl)(2-methoxyphenyl)methanone; (2-methoxyphenyl)(2-phenyloxazol-4-yl)methanone; (2-methoxyphenyl)(2-phenyloxazolidin-4-yl)methanone; (4,5-dihydro-2-phenyloxazol-4-yl)(2-methoxyphenyl)methanone; (2-methoxyphenyl)(2-phenyl-1H-imidazol-4-yl)methanone; (2-methoxyphenyl)(2-phenylimidazolidin-4-yl)methanone; (4,5-dihydro-2-phenyl-1H-imidazol-4-yl)(2-methoxyphenyl)methanone; (3,4-dimethoxyphenyl)(2-phenylthiazol-4-yl)methanone (compound 8e); (3,4-dimethoxyphenyl)(2-phenylthiazolidin-4-yl)methanone; (4,5-dihydro-2-phenylthiazol-4-yl)(3,4-dimethoxyphenyl)methanone; (3,4-dimethoxyphenyl)(2-phenyloxazol-4-yl)methanone; (3,4-dimethoxyphenyl)(2-phenyloxazolidin-4-yl)methanone; (4,5-dihydro-2-phenyloxazol-4-yl)(3,4-dimethoxyphenyl)methanone; (3,4-dimethoxyphenyl)(2-phenyl-1H-imidazol-4-yl)methanone; (3,4-dimethoxyphenyl)(2-phenylimidazolidin-4-yl)methanone; (4,5-dihydro-2-phenyl-1H-imidazol-4-yl)(3,4-dimethoxyphenyl)methanone; (3,4,5-trimethoxyphenyl)(2-phenylthiazol-4-yl)methanone (compound 8f); (3,4,5-trimethoxyphenyl)(2-phenylthiazolidin-4-yl)methanone; (4,5-dihydro-2-phenylthiazol-4-yl)(3,4,5-trimethoxyphenyl)methanone, which readily converts to compound 8f; (3,4,5-trimethoxyphenyl)(2-phenyloxazolidin-4-yl)methanone; (4,5-dihydro-2-phenyloxazol-4-yl)(3,4,5-trimethoxyphenyl)methanone; (3,4,5-trimethoxyphenyl)(2-phenyloxazol-4-yl)methanone; (4,5-dihydro-2-phenyl-1H-imidazol-4-yl)(3,4,5-trimethoxyphenyl)methanone; (3,4,5-trimethoxyphenyl)(2-phenyl-1H-imidazol-4-yl)methanone; (3,4,5-trimethoxyphenyl)(2-phenylimidazolidin-4-yl)methanone; (3,5-dimethoxyphenyl)(2-phenylthiazol-4-yl)methanone (compound 8g); (3,5-dimethoxyphenyl)(2-phenylthiazolidin-4-yl)methanone; (4,5-dihydro-2-phenylthiazol-4-yl)(3,5-dimethoxyphenyl)methanone; (3,5-dimethoxyphenyl)(2-phenyloxazol-4-yl)methanone; (3,5-dimethoxyphenyl)(2-phenyloxazolidin-4-yl)methanone; (4,5-dihydro-2-phenyloxazol-4-yl)(3,5-dimethoxyphenyl)methanone; (3,5-dimethoxyphenyl)(2-phenyl-1H-imidazol-4-yl)methanone; (3,5-dimethoxyphenyl)(2-phenylimidazolidin-4-yl)methanone; (4,5-dihydro-2-phenyl-1H-imidazol-4-yl)(3,5-dimethoxyphenyl)methanone; (2-fluorophenyl)(2-phenylthiazol-4-yl)methanone (compound 8h); (2-fluorophenyl)(2-phenylthiazolidin-4-yl)methanone; (4,5-dihydro-2-phenylthiazol-4-yl)(2-fluorophenyl)methanone; (2-fluorophenyl)(2-phenyloxazol-4-yl)methanone; (2-fluorophenyl)(2-phenyloxazolidin-4-yl)methanone; (4,5-dihydro-2-phenyloxazol-4-yl)(2-fluorophenyl)methanone; (2-fluorophenyl)(2-phenyl-1H-imidazol-4-yl)methanone; (2-fluorophenyl)(2-phenylimidazolidin-4-yl)methanone; (4,5-dihydro-2-phenyl-1H-imidazol-4-yl)(2-fluorophenyl)methanone; (2-phenylthiazol-4-yl)(pyridin-2-yl)methanone (compound 8i); (4,5-dihydro-2-phenylthiazol-4-yl)(pyridin-2-yl)methanone; (2-phenylthiazolidin-4-yl)(pyridin-2-yl)methanone; (2-phenyloxazol-4-yl)(pyridin-2-yl)methanone; (4,5-dihydro-2-phenyloxazol-4-yl)(pyridin-2-yl)methanone; (2-phenyloxazolidin-4-yl)(pyridin-2-yl)methanone; (2-phenyl-1H-imidazol-4-yl)(pyridin-2-yl)methanone; (4,5-dihydro-2-phenyl-1H-imidazol-4-yl)(pyridin-2-yl)methanone; (2-phenylimidazolidin-4-yl)(pyridin-2-yl)methanone; (2-p-tolylthiazol-4-yl)(3,4,5-trimethoxyphenyl)methanone (compound 8k); (4,5-dihydro-2-p-tolylthiazol-4-yl)(3,4,5-trimethoxyphenyl)methanone; (3,4,5-trimethoxyphenyl)(2-p- tolylthiazolidin-4-yl)methanone; (2-p-tolyloxazol-4-yl)(3,4,5-trimethoxyphenyl)methanone; (4,5-dihydro-2-p-tolyloxazol-4-yl)(3,4,5-trimethoxyphenyl)methanone; (3,4,5-trimethoxyphenyl)(2-p-tolyloxazolidin-4-yl)methanone; (2-p-tolyl-1H-imidazol-4-yl)(3,4,5-trimethoxyphenyl)methanone; (4,5-dihydro-2-p-tolyl-1H-imidazol-4-yl)(3,4,5-trimethoxyphenyl)methanone; (3,4,5-trimethoxyphenyl)(2-p-tolylimidazolidin-4-yl)methanone; (2-(2-fluorophenyl)-thiazol-4-yl)-(3,4,5-trimethoxyphenyl)methanone (compound 8l); (4,5-dihydro-2-(2-fluorophenyl)thiazol-4-yl)(3,4,5-trimethoxyphenyl)methanone; (3,4,5-trimethoxyphenyl)(2-(2-fluorophenyl)thiazolidin-4-yl)methanone; (2-(2-fluorophenyl)oxazol-4-yl)(3,4,5-trimethoxyphenyl)methanone; (4,5-dihydro-2-(2-fluorophenyl)oxazol-4-yl)(3,4,5-trimethoxyphenyl)methanone; (3,4,5-trimethoxyphenyl)(2-(2-fluorophenyl)oxazolidin-4-yl)methanone; (2-(2-fluorophenyl)-1H-imidazol-4-yl)(3,4,5-trimethoxyphenyl)methanone; (4,5-dihydro-2-(2-fluorophenyl)-1H-imidazol-4-yl)(3,4,5-trimethoxyphenyl)methanone; (3,4,5-trimethoxyphenyl)(2-(2-fluorophenyl)imidazolidin-4-yl)methanone; (2-(3-fluorophenyl)-thiazol-4-yl)(3,4,5-trimethoxyphenyl)methanone (compound 8m); (4,5-dihydro-2-(3-fluorophenyl)thiazol-4-yl)(3,4,5-trimethoxyphenyl)methanone; (3,4,5-trimethoxyphenyl)(2-(3-fluorophenyl)thiazolidin-4-yl)methanone; (2-(3-fluorophenyl)oxazol-4-yl)(3,4,5-trimethoxyphenyl)methanone; (4,5-dihydro-2-(3-fluorophenyl)oxazol-4-yl)(3,4,5-trimethoxyphenyl)methanone; (3,4,5-trimethoxyphenyl)(2-(3-fluorophenyl)oxazolidin-4-yl)methanone; (2-(3-fluorophenyl)-1H-imidazol-4-yl)(3,4,5-trimethoxyphenyl)methanone; (4,5-dihydro-2-(3-fluorophenyl)-1H-imidazol-4-yl)(3,4,5-trimethoxyphenyl)methanone; (3,4,5-trimethoxyphenyl)(2-(3-fluorophenyl)imidazolidin-4-yl)methanone; (2-(4-fluorophenyl)-thiazol-4-yl)(3,4,5-trimethoxyphenyl)methanone (compound 8n); (4,5-dihydro-2-(4-fluorophenyl)thiazol-4-yl)(3,4,5-trimethoxyphenyl)methanone; (3,4,5-trimethoxyphenyl)(2-(4-fluorophenyl)thiazolidin-4-yl)methanone; (2-(4-fluorophenyl)oxazol-4-yl)(3,4,5-trimethoxyphenyl)methanone; (4,5-dihydro-2-(4-fluorophenyl)oxazol-4-yl)(3,4,5-trimethoxyphenyl)methanone; (3,4,5-trimethoxyphenyl)(2-(4-fluorophenyl)oxazolidin-4-yl)methanone; (2-(4-fluorophenyl)-1H-imidazol-4-yl)(3,4,5-trimethoxyphenyl)methanone; (4,5-dihydro-2-(4-fluorophenyl)-1H-imidazol-4-yl)(3,4,5-trimethoxyphenyl)methanone; (3,4,5-trimethoxyphenyl)(2-(4-fluorophenyl)imidazolidin-4-yl)methanone; (2-(3,4-dimethoxyphenyl)-thiazol-4-yl)(3,4,5-trimethoxyphenyl)methanone (compound 8o); (4,5-dihydro-2-(3,4-dimethoxyphenyl)thiazol-4-yl)(3,4,5-trimethoxyphenyl)methanone; (3,4,5-trimethoxyphenyl)(2-(3,4-dimethoxyphenyl)thiazolidin-4-yl)methanone; (2-(3,4-dimethoxyphenyl)oxazol-4-yl)(3,4,5-trimethoxyphenyl)methanone; (4,5-dihydro-2-(3,4-dimethoxyphenyl)oxazol-4-yl)(3,4,5-trimethoxyphenyl)methanone; (3,4,5-trimethoxyphenyl)(2-(3,4-dimethoxyphenyl)oxazolidin-4-yl)methanone; (2-(3,4-dimethoxyphenyl)-1H-imidazol-4-yl)(3,4,5-trimethoxyphenyl)methanone; (4,5-dihydro-2-(3,4-dimethoxyphenyl)-1H-imidazol-4-yl)(3,4,5-trimethoxyphenyl)methanone; (3,4,5-trimethoxyphenyl)(2-(3,4-dimethoxyphenyl)imidazolidin-4-yl)methanone; (2-(4-nitrophenyl)-thiazol-4-yl)(3,4,5-trimethoxyphenyl)methanone (compound 8p); (4,5-dihydro-2-(4-nitrophenyl)thiazol-4-yl)(3,4,5-trimethoxyphenyl)methanone; (3,4,5-trimethoxyphenyl)(2-(4-nitrophenyl)thiazolidin-4-yl)methanone; (2-(4-nitrophenyl)oxazol-4-yl)(3,4,5-trimethoxyphenyl)methanone; (4,5-dihydro-2-(4-nitrophenyl)oxazol-4-yl)(3,4,5-trimethoxyphenyl)methanone; (3,4,5-trimethoxyphenyl)(2-(4-nitrophenyl)oxazolidin-4-yl)methanone; (2-(4-nitrophenyl)-1H-imidazol-4-yl)(3,4,5-trimethoxyphenyl)methanone; (4,5-dihydro-2-(4-nitrophenyl)-1H-imidazol-4-yl)(3,4,5-trimethoxyphenyl)methanone; (3,4,5-trimethoxyphenyl)(2-(4-nitrophenyl)imidazolidin-4-yl)methanone; (2-(4-cyanophenyl)-thiazol-4-yl)(3,4,5-trimethoxyphenyl)methanone (compound 8q); (4,5-dihydro-2-(4-cyanophenyl)thiazol-4-yl)(3,4,5-trimethoxyphenyl)methanone; (3,4,5-trimethoxyphenyl)(2-(4-cyanophenyl)thiazolidin-4-yl)methanone; (2-(4-cyanophenyl)oxazol-4-yl)(3,4,5-trimethoxyphenyl)methanone; (4,5-dihydro-2-(4-cyanophenyl)oxazol-4-yl)(3,4,5-trimethoxyphenyl)methanone; (3,4,5-trimethoxyphenyl)(2-(4-cyanophenyl)oxazolidin-4-yl)methanone; (2-(4-cyanophenyl)-1H-imidazol-4-yl)(3,4,5-trimethoxyphenyl)methanone; (4,5-dihydro-2-(4-cyanophenyl)-1H-imidazol-4-yl)(3,4,5-trimethoxyphenyl)methanone; (3,4,5-trimethoxyphenyl)(2-(4-cyanophenyl)imidazolidin-4-yl)methanone; 4-(4-(3,4,5-trimethoxybenzoyl)-thiazol-2-yl)-benzoic acid (compound 8r); 4-(4-(3,4,5-trimethoxybenzoyl)-(1,3-dihydro)thiazol-2-yl)-benzoic acid; 4-(4-(3,4,5-trimethoxybenzoyl)-thiazolidin-2-yl)-benzoic acid; 4-(4-(3,4,5-trimethoxybenzoyl)-oxazol-2-yl)-benzoic acid; 4-(4-(3,4,5-trimethoxybenzoyl)-(1,3-dihydro)oxazol-2-yl)-benzoic acid; 4-(4-(3,4,5-trimethoxybenzoyl)-oxazolidin-2-yl)-benzoic acid; 4-(4-(3,4,5-trimethoxybenzoyl)-1H-imidazol-2-yl)-benzoic acid; 4-(4-(3,4,5-trimethoxybenzoyl)-(1,3-dihydro)-1H-imidazol-2-yl)-benzoic acid; 4-(4-(3,4,5-trimethoxybenzoyl)-imidazolidin-2-yl)-benzoic acid; methyl-4-(4-(3,4,5-trimethoxybenzoyl)-thiazol-2-yl)-benzoate (compound 8s); methyl-4-(4-(3,4,5-trimethoxybenzoyl)-(1,3-dihydro)thiazol-2-yl)-benzoate; methyl-4-(4-(3,4,5-trimethoxybenzoyl)-thiazolidin-2-yl)-benzoate; methyl-4-(4-(3,4,5-trimethoxybenzoyl)-oxazol-2-yl)-benzoate; methyl-4-(4-(3,4,5-trimethoxybenzoyl)-(1,3-dihydro)oxazol-2-yl)-benzoate; methyl-4-(4-(3,4,5-trimethoxybenzoyl)-oxazolidin-2-yl)-benzoate; methyl-4-(4-(3,4,5-trimethoxybenzoyl)-1H-imidazol-2-yl)-benzoate; methyl-4-(4-(3,4,5-trimethoxybenzoyl)-(1,3-dihydro)-1H-imidazol-2-yl)-benzoate; methyl-4-(4-(3,4,5-trimethoxybenzoyl)-imidazolidin-2-yl)-benzoate; (2-(4-(trifluoromethyl)-phenyl)-thiazol-4-yl)(3,4,5-trimethoxyphenyl)methanone (compound 8t); (4,5-dihydro-2-(4-(trifluoromethyl)-phenyl)thiazol-4-yl)(3,4,5-trimethoxyphenyl)methanone; (3,4,5-trimethoxyphenyl)(2-(4-cyanophenyl)thiazolidin-4-yl)methanone; (2-(4-(trifluoromethyl)-phenyl)oxazol-4-yl)(3,4,5-trimethoxyphenyl)methanone; (4,5-dihydro-2-(4-(trifluoromethyl)-phenyl)oxazol-4-yl)(3,4,5-trimethoxyphenyl)methanone; (3,4,5-trimethoxyphenyl)(2-(4-(trifluoromethyl)-phenyl)oxazolidin-4-yl)methanone; (2-(4-(trifluoromethyl)-phenyl)-1H-imidazol-4-yl)(3,4,5-trimethoxyphenyl)methanone; (4,5-dihydro-2-(4-(trifluoromethyl)-phenyl)-1H-imidazol-4-yl)(3,4,5-trimethoxyphenyl)methanone; (3,4,5-trimethoxyphenyl)(2-(4-(trifluoromethyl)-phenyl)imidazolidin-4-yl)methanone; (2-(4-bromophenyl)-thiazol-4-yl)-(3,4,5-trimethoxyphenyl)methanone (compound 8u); (4,5-dihydro-2-(4-bromophenyl)thiazol-4-yl)(3,4,5-trimethoxyphenyl)methanone; (3,4,5-trimethoxyphenyl)(2-(4-bromophenyl)thiazolidin-4-yl)methanone; (2-(4-bromophenyl)oxazol-4-yl)(3,4,5-trimethoxyphenyl)methanone; (4,5-dihydro-2-(4-bromophenyl)oxazol-4-yl)(3,4,5-trimethoxyphenyl)methanone; (3,4,5-trimethoxyphenyl)(2-(4-bromophenyl)oxazolidin-4-yl)methanone; (2-(4-bromophenyl)-1H-imidazol-4-yl)(3,4,5-trimethoxyphenyl)methanone; (4,5-dihydro-2-(4-bromophenyl)-1H-imidazol-4-yl)(3,4,5- trimethoxyphenyl)methanone; (3,4,5-trimethoxyphenyl)(2-(4-bromophenyl)imidazolidin-4-yl)methanone; (2-(4-ethylphenyl)-thiazol-4-yl)-(3,4,5-trimethoxy-phenyl)methanone (compound 8v); (4,5-dihydro-2-(4-ethylphenyl)thiazol-4-yl)(3,4,5-trimethoxyphenyl)methanone; (3,4,5-trimethoxyphenyl)(2-(4-ethylphenyl)thiazolidin-4-yl)methanone; (2-(4-ethylphenyl)oxazol-4-yl)(3,4,5-trimethoxyphenyl)methanone; (4,5-dihydro-2-(4-ethylphenyl)oxazol-4-yl)(3,4,5-trimethoxyphenyl)methanone; (3,4,5-trimethoxyphenyl)(2-(4-ethylphenyl)oxazolidin-4-yl)methanone; (2-(4-ethylphenyl)-1H-imidazol-4-yl)(3,4,5-trimethoxyphenyl)methanone; (4,5-dihydro-2-(4-ethylphenyl)-1H-imidazol-4-yl)(3,4,5-trimethoxyphenyl)methanone; (3,4,5-trimethoxyphenyl)(2-(4-ethylphenyl)imidazolidin-4-yl)methanone; (2-(4-aminophenyl)-thiazol-4-yl)-(3,4,5-trimethoxy-phenyl)methanone (compound 8w); (2-(4-aminophenyl)thiazolidin-4-yl)(3,4,5-trimethoxyphenyl)methanone; (2-(4-aminophenyl)-4,5-dihydrothiazol-4-yl)(3,4,5-trimethoxyphenyl)methanone; (2-(4-aminophenyl)-oxazol-4-yl)-(3,4,5-trimethoxy-phenyl)methanone; (2-(4-aminophenyl)oxazolidin-4-yl)(3,4,5-trimethoxyphenyl)methanone; (2-(4-aminophenyl)-4,5-dihydrooxazol-4-yl)(3,4,5-trimethoxyphenyl)methanone; (2-(4-aminophenyl)-1H-imidazol-4-yl)-(3,4,5-trimethoxy-phenyl)methanone; (2-(4-aminophenyl)-1H-imidazolidin-4-yl)(3,4,5-trimethoxyphenyl)methanone; (2-(4-aminophenyl)-4,5-dihydroimidazol-4-yl)(3,4,5-trimethoxyphenyl)methanone; (2-(4-acetamidophenyl)thiazolidin-4-yl)(3,4,5-trimethoxyphenyl)methanone; (2-(4-acetamidophenyl)-4,5-dihydrothiazol-4-yl)(3,4,5-trimethoxyphenyl)methanone; (2-(4-acetamidophenyl)-thiazol-4-yl)(3,4,5-trimethoxyphenyl)methanone; (3,4,5-trimethoxyphenyl)(2-(3,4,5-trimethoxyphenyl)thiazol-4-yl)methanone; (4,5-dihydro-2-(3,4,5-trimethoxyphenyl)thiazol-4-yl)(3,4,5-trimethoxyphenyl)methanone; (3,4,5-trimethoxyphenyl)(2-(3,4,5-trimethoxyphenyl)thiazolidin-4-yl)methanone; (3,4,5-trimethoxyphenyl)(2-(3,4-dimethoxyphenyl)thiazol-4-yl)methanone; (4,5-dihydro-2-(3,4-dimethoxyphenyl)thiazol-4-yl)(3,4,5-trimethoxyphenyl)methanone; (3,4,5-trimethoxyphenyl)(2-(3,4-dimethoxyphenyl)thiazolidin-4-yl)methanone; (2-(4-fluorophenyl)thiazolidin-4-yl)(3,4,5-trimethoxyphenyl)methanone; (2-(4-fluorophenyl)-4,5-dihydrothiazol-4-yl)(3,4,5-trimethoxyphenyl)methanone; (2-(4-fluorophenyl)-thiazol-4-yl)(3,4,5-trimethoxyphenyl)methanone; (3,4,5-trimethoxyphenyl)(2-(2-methoxyphenyl)thiazol-4-yl)methanone; (4,5-dihydro-2-(2-methoxyphenyl)thiazol-4-yl)(3,4,5-trimethoxyphenyl)methanone; (3,4,5-trimethoxyphenyl)(2-(2-methoxyphenyl)thiazolidin-4-yl)methanone; (2-(pyridin-4-yl)-thiazol-4-yl)-(3,4,5-trimethoxyphenyl)methanone (compound 8x); (4,5-dihydro-2-pyridin-4-yl)thiazol-4-yl)(3,4,5-trimethoxyphenyl)methanone; (3,4,5-trimethoxyphenyl)(2-(pyridin-4-yl)thiazolidin-4-yl)methanone; (2-(pyridin-4-yl)-oxazol-4-yl)-(3,4,5-trimethoxyphenyl)methanone; (4,5-dihydro-2-(pyridin-4-yl)oxazol-4-yl)(3,4,5-trimethoxyphenyl)methanone; (3,4,5-trimethoxyphenyl)(2-pyridin-4-yl)oxazolidin-4-yl)methanone; (2-(pyridin-4-yl)-1H-imidazol-4-yl)-(3,4,5-trimethoxyphenyl)methanone; (4,5-dihydro-2-(pyridin-4-yl)-1H-imidazol-4-yl)(3,4,5-trimethoxyphenyl)methanone; (3,4,5-trimethoxyphenyl)(2-(pyridin-4-yl)imidazolidin-4-yl)methanone; (2-(pyrimidin-2-yl)-thiazol-4-yl)-(3,4,5-trimethoxyphenyl)methanone (compound 8y); (4,5-dihydro-2-(pyrimidin-4-yl)thiazol-4-yl)(3,4,5-trimethoxyphenyl)methanone; (3,4,5-trimethoxyphenyl)(2-(pyrimidin-4-yl)thiazolidin-4-yl)methanone; (2-(pyrimidin-4-yl)-oxazol-4-yl)-(3,4,5-trimethoxyphenyl)methanone; (4,5-dihydro-2-(pyrimidin-4-yl)oxazol-4-yl)(3,4,5-trimethoxyphenyl)methanone; (3,4,5-trimethoxyphenyl)(2-(pyrimidin-4-yl)oxazol-4-yl)methanone; (2-(pyrimidin-4-yl)-1H-imidazol-4-yl)-(3,4,5-trimethoxyphenyl)methanone; (4,5-dihydro-2-(pyrimidin-4-yl)-1H-imidazol-4-yl)(3,4,5-trimethoxyphenyl)methanone; (3,4,5-trimethoxyphenyl)(2-(pyrimidin-4-yl)imidazolidin-4-yl)methanone; (2-(thiophen-2-yl)-thiazol-4-yl)-(3,4,5-trimethoxyphenyl)methanone (compound 8z); (4,5-dihydro-2-(thiophen-2-yl)thiazol-4-yl)(3,4,5-trimethoxyphenyl)methanone; (3,4,5-trimethoxyphenyl)(2-(thiophen-2-yl)thiazolidin-4-yl)methanone; (2-(thiophen-2-yl)-oxazol-4-yl)-(3,4,5-trimethoxyphenyl)methanone; (4,5-dihydro-2-(thiophen-2-yl)oxazol-4-yl)(3,4,5-trimethoxyphenyl)methanone; (3,4,5-trimethoxyphenyl)(2-(thiophen-2-yl)oxazolidin-4-yl)methanone; (2-(thiophen-2-yl)-1H-imidazol-4-yl)-(3,4,5-trimethoxyphenyl)methanone; (4,5-dihydro-2-(thiophen-2-yl)-1H-imidazol-4-yl)(3,4,5-trimethoxyphenyl)methanone; (3,4,5-trimethoxyphenyl)(2-(thiophen-2-yl)imidazolidin-4-yl)methanone; (2-(1H-indol-5-yl)thiazol-4-yl)(3,4,5-trimethoxyphenyl)methanone (compound 31); (2-(1H-indol-5-yl)thiazolidin-4-yl)(3,4,5-trimethoxyphenyl)methanone; (4,5-dihydro-2-(1H-indol-5-yl)thiazol-4-yl)(3,4,5-trimethoxyphenyl)methanone; (2-(1H-indol-5-yl)oxazol-4-yl)(3,4,5-trimethoxyphenyl)methanone; (2-(1H-indol-5-yl)oxazolidin-4-yl)(3,4,5-trimethoxyphenyl)methanone; (4,5-dihydro-2-(1H-indol-5-yl)oxazol-4-yl)(3,4,5-trimethoxyphenyl)methanone; (2-(1H-indol-5-yl)imidazol-4-yl)(3,4,5-trimethoxyphenyl)methanone; (2-(1H-indol-5-yl)imidazolidin-4-yl)(3,4,5-trimethoxyphenyl)methanone; (4,5-dihydro-2-(1H-indol-5-yl)imidazol-4-yl)(3,4,5-trimethoxyphenyl)methanone; (2-(1H-indol-2-yl)thiazol-4-yl)(3,4,5-trimethoxyphenyl)methanone (compound 32); (4,5-dihydro-2-(1H-indol-2-yl)thiazol-4-yl)(3,4,5-trimethoxyphenyl)methanone; (2-(1H-indol-2-yl)thiazolidin-4-yl)(3,4,5-trimethoxyphenyl)methanone; (2-(1H-indol-2-yl)oxazol-4-yl)(3,4,5-trimethoxyphenyl)methanone; (4,5-dihydro-2-(1H-indol-2-yl)oxazol-4-yl)(3,4,5-trimethoxyphenyl)methanone; (2-(1H-indol-2-yl)oxazolidin-4-yl)(3,4,5-trimethoxyphenyl)methanone; (2-(1H-indol-2-yl)imidazol-4-yl)(3,4,5-trimethoxyphenyl)methanone; (4,5-dihydro-2-(1H-indol-2-yl)imidazol-4-yl)(3,4,5-trimethoxyphenyl)methanone; (2-(1H-indol-2-yl)imidazolidin-4-yl)(3,4,5-trimethoxyphenyl)methanone; (2-(1H-indol-1-yl)thiazol-4-yl)(3,4,5-trimethoxyphenyl)methanone; (4,5-dihydro-2-(1H-indol-1-yl)thiazol-4-yl)(3,4,5-trimethoxyphenyl)methanone; (2-(1H-indol-1-yl)thiazolidin-4-yl)(3,4,5-trimethoxyphenyl)methanone; (2-(1H-indol-1-yl)oxazol-4-yl)(3,4,5-trimethoxyphenyl)methanone; (4,5-dihydro-2-(1H-indol-1-yl)oxazol-4-yl)(3,4,5-trimethoxyphenyl)methanone; (2-(1H-indol-1-yl)oxazolidin-4-yl)(3,4,5-trimethoxyphenyl)methanone; (2-(1H-indol-1-yl)imidazol-4-yl)(3,4,5-trimethoxyphenyl)methanone; (4,5-dihydro-2-(1H-indol-1-yl)imidazol-4-yl)(3,4,5-trimethoxyphenyl)methanone; (2-(1H-indol-1-yl)imidazolidin-4-yl)(3,4,5-trimethoxyphenyl)methanone; (2-(1H-indol-3-yl)thiazol-4-yl)(3,4,5-trimethoxyphenyl)methanone; (4,5-dihydro-2-(1H-indol-3-yl)thiazol-4-yl)(3,4,5-trimethoxyphenyl)methanone; (2-(1H-indol-3-yl)thiazolidin-4-yl)(3,4,5-trimethoxyphenyl)methanone; (2-(1H-indol-3-yl)oxazol-4-yl)(3,4,5-trimethoxyphenyl)methanone; (4,5-dihydro-2-(1H-indol-3-yl)oxazol-4-yl)(3,4,5-trimethoxyphenyl)methanone; (2-(1H-indol-3-yl)oxazolidin-4-yl)(3,4,5-trimethoxyphenyl)methanone; (2-(1H-indol-3-yl)imidazol-4-yl)(3,4,5-trimethoxyphenyl)methanone; (4,5-dihydro-2-(1H-indol-3-yl)imidazol-4-yl)(3,4,5-trimethoxyphenyl)methanone; (2-

(1H-indol-3-yl)imidazolidin-4-yl)(3,4,5-trimethoxyphenyl)methanone; (2-(1H-indol-4-yl)thiazol-4-yl)(3,4,5-trimethoxyphenyl)methanone; (4,5-dihydro-2-(1H-indol-4-yl)thiazol-4-yl)(3,4,5-trimethoxyphenyl)methanone; (2-(1H-indol-4-yl)thiazolidin-4-yl)(3,4,5-trimethoxyphenyl)methanone; (2-(1H-indol-4-yl)oxazol-4-yl)(3,4,5-trimethoxyphenyl)methanone; (4,5-dihydro-2-(1H-indol-4-yl)oxazol-4-yl)(3,4,5-trimethoxyphenyl)methanone; (2-(1H-indol-4-yl)oxazolidin-4-yl)(3,4,5-trimethoxyphenyl)methanone; (2-(1H-indol-4-yl)imidazol-4-yl)(3,4,5-trimethoxyphenyl)methanone; (4,5-dihydro-2-(1H-indol-4-yl)imidazol-4-yl)(3,4,5-trimethoxyphenyl)methanone; (2-(1H-indol-4-yl)imidazolidin-4-yl)(3,4,5-trimethoxyphenyl)methanone; (2-(1H-indol-6-yl)thiazol-4-yl)(3,4,5-trimethoxyphenyl)methanone; (4,5-dihydro-2-(1H-indol-6-yl)thiazol-4-yl)(3,4,5-trimethoxyphenyl)methanone; (2-(1H-indol-6-yl)thiazolidin-4-yl)(3,4,5-trimethoxyphenyl)methanone; (2-(1H-indol-6-yl)oxazol-4-yl)(3,4,5-trimethoxyphenyl)methanone; (4,5-dihydro-2-(1H-indol-6-yl)oxazol-4-yl)(3,4,5-trimethoxyphenyl)methanone; (2-(1H-indol-6-yl)oxazolidin-4-yl)(3,4,5-trimethoxyphenyl)methanone; (2-(1H-indol-6-yl)imidazol-4-yl)(3,4,5-trimethoxyphenyl)methanone; (4,5-dihydro-2-(1H-indol-6-yl)imidazol-4-yl)(3,4,5-trimethoxyphenyl)methanone; (2-(1H-indol-6-yl)imidazolidin-4-yl)(3,4,5-trimethoxyphenyl)methanone; (2-(1H-indol-7-yl)thiazol-4-yl)(3,4,5-trimethoxyphenyl)methanone; (4,5-dihydro-2-(1H-indol-7-yl)thiazol-4-yl)(3,4,5-trimethoxyphenyl)methanone; (2-(1H-indol-7-yl)thiazolidin-4-yl)(3,4,5-trimethoxyphenyl)methanone; (2-(1H-indol-1-yl)oxazol-4-yl)(3,4,5-trimethoxyphenyl)methanone; (4,5-dihydro-2-(1H-indol-7-yl)oxazol-4-yl)(3,4,5-trimethoxyphenyl)methanone; (2-(1H-indol-7-yl)oxazolidin-4-yl)(3,4,5-trimethoxyphenyl)methanone; (2-(1H-indol-7-yl)imidazol-4-yl)(3,4,5-trimethoxyphenyl)methanone; (4,5-dihydro-2-(1H-indol-7-yl)imidazol-4-yl)(3,4,5-trimethoxyphenyl)methanone; and (2-(1H-indol-7-yl)imidazolidin-4-yl)(3,4,5-trimethoxyphenyl)methanone.

Preferably, the $R^1$ group is substituted or unsubstituted phenyl, substituted or unsubstituted thiophene-yl, or substituted or unsubstituted indolyl; and the $R^2$ group is 3,4,5-trimethoxyphenyl. Thus, of the above-listed compounds, (3,4,5-trimethoxyphenyl)(2-phenylthiazol-4-yl)methanone (compound 8f); (2-p-tolylthiazol-4-yl)(3,4,5-trimethoxyphenyl)methanone (compound 8k); (2-(4-fluorophenyl)-thiazol-4-yl)(3,4,5-trimethoxyphenyl)methanone (compound 8n); (2-(4-nitrophenyl)-thiazol-4-yl)(3,4,5-trimethoxyphenyl)methanone (compound 8p); (2-(4-cyanophenyl)-thiazol-4-yl)(3,4,5-trimethoxyphenyl)methanone (compound 8q); (2-(4-(trifluoromethyl)-phenyl)-thiazol-4-yl)(3,4,5-trimethoxyphenyl)methanone (compound 8t); (2-(4-bromophenyl)-thiazol-4-yl)-(3,4,5-trimethoxyphenyl)methanone (compound 8u); (2-(4-ethylphenyl)-thiazol-4-yl)-(3,4,5-trimethoxy-phenyl)methanone (compound 8v); (2-(4-aminophenyl)-thiazol-4-yl)-(3,4,5-trimethoxy-phenyl)methanone (compound 8w); (2-(thiophen-2-yl)-thiazol-4-yl)-(3,4,5-trimethoxyphenyl)methanone (compound 8z); (2-(1H-indol-5-yl)thiazol-4-yl)(3,4,5-trimethoxyphenyl)methanone (compound 31); (2-(1H-indol-2-yl)thiazol-4-yl)(3,4,5-trimethoxyphenyl)methanone (compound 32); (2-(1H-indol-1-yl)thiazol-4-yl)(3,4,5-trimethoxyphenyl)methanone; (2-(1H-indol-3-yl)thiazol-4-yl)(3,4,5-trimethoxyphenyl)methanone; (2-(1H-indol-4-yl)thiazol-4-yl)(3,4,5-trimethoxyphenyl)methanone; (2-(1H-indol-6-yl)thiazol-4-yl)(3,4,5-trimethoxyphenyl)methanone; and (2-(1H-1-indol-7-yl)thiazol-4-yl)(3,4,5-trimethoxyphenyl)methanone are preferred.

According to another embodiment, the class of compounds has a structure according to formula (III):

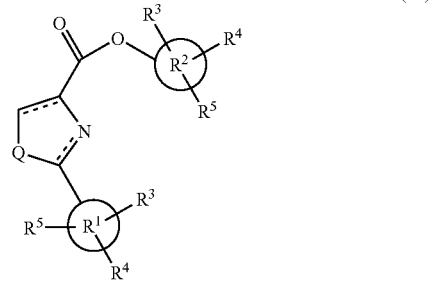

(III)

where X is O=, Y is O, and Q and $R^1$-$R^5$ are defined as above for formula (I).

Exemplary compounds of formula (III) include, without limitation: 3,4,5-trimethoxyphenyl 4,5-dihydro-2-phenylthiazole-4-carboxylate; 3,4,5-trimethoxyphenyl 2-phenylthiazole-4-carboxylate; 3,4,5-trimethoxyphenyl 2-phenylthiazolidine-4-carboxylate; 3,4,5-trimethoxyphenyl 2-phenyloxazolidine-4-carboxylate; 3,4,5-trimethoxyphenyl 4,5-dihydro-2-phenyloxazole-4-carboxylate; 3,4,5-trimethoxyphenyl 2-phenyloxazole-4-carboxylate; 3,4,5-trimethoxyphenyl 2-phenylimidazolidine-4-carboxylate; 3,4,5-trimethoxyphenyl 4,5-dihydro-2-phenyl-1H-imidazole-4-carboxylate; and 3,4,5-trimethoxyphenyl 2-phenyl-1H-imidazole-4-carboxylate.

According to another embodiment, the class of compounds has a structure according to formula (IV):

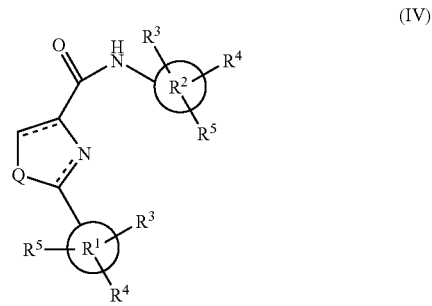

(IV)

where X is O=, Y is —NH—, and Q and $R^1$-$R^5$ are defined as above for formula (I).

Exemplary compounds of formula (IV) include, without limitation: N-(3,4,5-trimethoxyphenyl)-2-phenyloxazolidine-4-carboxamide; 4,5-dihydro-N-(3,4,5-trimethoxyphenyl)-2-phenyloxazole-4-carboxamide; N-(3,4,5-trimethoxyphenyl)-2-phenyloxazole-4-carboxyamide; N-(3,4,5-trimethoxyphenyl)-2-phenyl-1H-imidazole-4-carboxamide; 4,5-dihydro-N-(3,4,5-trimethoxyphenyl)-2-phenyl-1H-imidazole-4-carboxamide; N-(3,4,5-trimethoxyphenyl)-2-phenylimidazolidine-4-carboxamide; 4,5-dihydro-N-(3,4,5-trimethoxyphenyl)-2-phenylthiazole-4-carboxamide; N-(3,4,5-trimethoxyphenyl)-2-phenylthiazole-4-carboxamide; and N-(3,4,5-trimethoxyphenyl)-2-phenylthiazolidine-4-carboxamide.

According to another embodiment, the class of compounds has a structure according to formula (V):

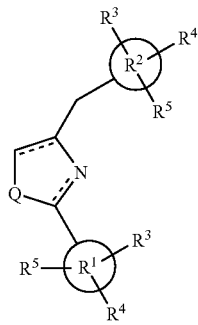

(V)

where X and Y are omitted, and Q and R¹-R⁵ are defined as above for formula (I).

Exemplary compounds of formula (V) include, without limitation: 4-(3,4,5-trimethoxybenzyl)-2-phenylthiazolidine; 4-(3,4,5-trimethoxybenzyl)-4,5-dihydro-2-phenylthiazole; 4-(3,4,5-trimethoxybenzyl)-2-phenylthiazole; 4-(3,4,5-trimethoxybenzyl)-2-phenyloxazole; 4-(3,4,5-trimethoxybenzyl)-4,5-dihydro-2-phenyloxazole; 4-(3,4,5-trimethoxybenzyl)-2-phenyloxazolidine; 4-(3,4,5-trimethoxybenzyl)-2-phenylimidazolidine; 4-(3,4,5-trimethoxybenzyl)-4,5-dihydro-2-phenyl-1H-imidazole; and 4-(3,4,5-trimethoxybenzyl)-2-phenyl-1H-imidazole.

According to another embodiment, the class of compounds has a structure according to formula (VI):

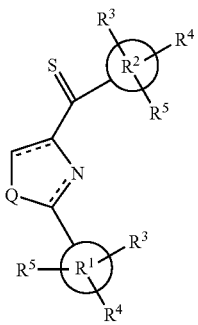

(VI)

where X is S=, Y is omitted, and Q and R¹-R⁵ are defined as above for formula (I).

Exemplary compounds of formula (VI) include, without limitation: phenyl(2-phenylthiazolidin-4-yl)methanethione; phenyl(2-phenyloxazolidin-4-yl)methanethione; (4,5-dihydro-2-phenyloxazol-4-yl)(phenyl)methanethione; phenyl(2-phenyloxazol-4-yl)methanethione; (3,4,5-trimethoxyphenyl)(2-phenylthiazol-4-yl)methanethione; (3,4,5-trimethoxyphenyl)(2-phenylthiazolidin-4-yl)methanethione; (3,4,5-trimethoxyphenyl)(2-phenyloxazolidin-4-yl)methanethione; (4,5-dihydro-2-phenyloxazol-4-yl)(3,4,5-trimethoxyphenyl)methanethione; (3,4,5-trimethoxyphenyl)(2-phenyloxazol-4-yl)methanethione; (4,5-dihydro-2-phenyl-1H-imidazol-4-yl)(3,4,5-trimethoxyphenyl)methanethione; (3,4,5-trimethoxyphenyl)(2-phenyl-1H-imidazol-4-yl)methanethione; and (3,4,5-trimethoxyphenyl)(2-phenylimidazolidin-4-yl)methanethione.

According to another preferred embodiment, the class of compounds has a structure according to formula (VII):

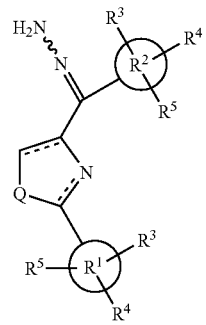

(VII)

where X is =N—NH₂, Y is omitted, and Q and R¹-R⁵ are defined as above for formula (I).

Exemplary compounds according to formula (VII) include, without limitation, (Z)-1-((3,4,5-trimethoxyphenyl) (2-phenylthiazol-4-yl)methylene)hydrazine (compound 33); (E)-1-((3,4,5-trimethoxyphenyl)(2-phenylthiazol-4-yl)methylene)hydrazine (compound 34); (24Z)-1-((4,5-dihydro-2-phenylthiazol-4-yl)(3,4,5-trimethoxyphenyl)methylene)hydrazine; (24E)-1-((4,5-dihydro-2-phenylthiazol-4-yl)(3,4,5-trimethoxyphenyl)methylene)hydrazine; (Z)-1-((3,4,5-trimethoxyphenyl)(2-phenylthiazolidin-4-yl)methylene) hydrazine; (F)-1-((3,4,5-trimethoxyphenyl)(2-phenylthiazolidin-4-yl)methylene)hydrazine; (Z)-1-((3,4,5-trimethoxyphenyl)(2-phenyloxazol-4-yl)methylene) hydrazine; (E)-1-((3,4,5-trimethoxyphenyl)(2-phenyloxazol-4-yl)methylene)hydrazine; (24Z)-1-((4,5-dihydro-2-phenyloxazol-4-yl)(3,4,5-trimethoxyphenyl)methylene)hydrazine; (24E)-1-((4,5-dihydro-2-phenyloxazol-4-yl)(3,4,5-trimethoxyphenyl)methylene) hydrazine; (Z)-1-((3,4,5-trimethoxyphenyl)(2-phenyloxazolidin-4-yl)methylene)hydrazine; (E)-1-((3,4,5-trimethoxyphenyl)(2-phenyloxazolidin-4-yl)methylene) hydrazine; (Z)-1-((3,4,5-trimethoxyphenyl)(2-phenyl-1H-imidazol-4-yl)methylene)hydrazine; (E)-1-((3,4,5-trimethoxyphenyl)(2-phenyl-1H-imidazol-4-yl)methylene) hydrazine; (24Z)-1-((4,5-dihydro-2-phenyl-1H-imidazol-4-yl)(3,4,5-trimethoxyphenyl)methylene) hydrazine; (24E)-1-((4,5-dihydro-2-phenyl-1H-imidazol-4-yl)(3,4,5-trimethoxyphenyl)methylene)hydrazine; (Z)-1-((3,4,5-trimethoxyphenyl)(2-phenylimidazolidin-4-yl)methylene) hydrazine; and (E)-1-((3,4,5-trimethoxyphenyl)(2-phenylimidazolidin-4-yl)methylene)hydrazine.

According to another preferred embodiment, the class of compounds has a structure according to formula (VIII):

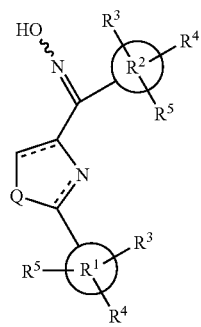

(VIII)

where X is =N—OH, Y is omitted, and Q and R¹-R⁵ are defined as above for formula (I).

Exemplary compounds according to formula (VIII) include, without limitation, (Z)-(2-phenylthiazol-4-yl)(3,4,5-trimethoxyphenyl)methanone oxime (compound 35); (E)-(2-phenylthiazol-4-yl)(3,4,5-trimethoxyphenyl)methanone oxime (compound 36); (24Z)-1-(4,5-dihydro-2-phenylthiazol-4-yl)(3,4,5-trimethoxyphenyl)methanone oxime; (24E)-1-(4,5-dihydro-2-phenylthiazol-4-yl)(3,4,5-trimethoxyphenyl)methanone oxime; (Z)-1-(3,4,5-trimethoxyphenyl)(2-phenylthiazolidin-4-yl)methanone oxime; (E)-1-(3,4,5-trimethoxyphenyl)(2-phenylthiazolidin-4-yl)methanone oxime; (Z)-1-(3,4,5-trimethoxyphenyl)(2-phenyloxazol-4-yl)methanone oxime; (E)-1-(3,4,5-trimethoxyphenyl)(2-phenyloxazol-4-yl)methanone oxime; (24Z)-1-(4,5-dihydro-2-phenyloxazol-4-yl)(3,4,5-trimethoxyphenyl)methanone oxime; (24E)-1-(4,5-dihydro-2-phenyloxazol-4-yl)(3,4,5-trimethoxyphenyl)methanone oxime; (Z)-1-(3,4,5-trimethoxyphenyl)(2-phenyloxazolidin-4-yl)methanone oxime; (E)-1-(3,4,5-trimethoxyphenyl)(2-phenyloxazolidin-4-yl)methanone oxime; (Z)-1-(3,4,5-trimethoxyphenyl)(2-phenyl-1H-imidazol-4-yl)methanone oxime; (E)-1-(3,4,5-trimethoxyphenyl)(2-phenyl-1H-imidazol-4-yl)methanone oxime; (24Z)-1-(4,5-dihydro-2-phenyl-1H-imidazol-4-yl)(3,4,5-trimethoxyphenyl)methanone oxime; (24E)-1-(4,5-dihydro-2-phenyl-1H-imidazol-4-yl)(3,4,5-trimethoxyphenyl)methanone oxime; (Z)-1-(3,4,5-trimethoxyphenyl)(2-phenylimidazolidin-4-yl)methanone oxime; and (E)-1-(3,4,5-trimethoxyphenyl)(2-phenylimidazolidin-4-yl)methanone oxime.

Certain compounds, particularly those possessing acid or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

The compounds of the present invention may also be administered as prodrugs. Thus, certain derivatives which may have little or no pharmacological activity themselves can, when administered into or onto the body, be converted into compounds of the present invention having the desired activity, for example, by hydrolytic cleavage. Further information on the use of prodrugs may be found in *Pro-drugs as Novel Delivery Systems*, Vol. 14, ACS Symposium Series (Higuchi and Stella); and *Bioreversible Carriers in Drug Design*, Pergamon Press (ed. E B Roche, American Pharmaceutical Association) (1987), each of which is hereby incorporated by reference in its entirety.

Prodrugs can, for example, be produced by replacing appropriate functionalities present in the compounds of the present invention with certain moieties known to those skilled in the art as pro-moieties. Examples of such prodrugs include, without limitation, replacement of hydrogen in an alcohol functionality (—OH) by a C1 to C6 alkyl to form an ether; and (ii) replacement of hydrogen in a secondary amino functionality with a C1 to C10 alkanoyl to form an amide.

Compounds of the present invention can also be in the form of a hydrate, which means that the compound further includes a stoichiometric or non-stoichiometric amount of water bound by non-covalent intermolecular forces.

The compounds of the present invention can also be present in the form of a racemic mixture, containing substantially equivalent amounts of stereoisomers. In another embodiment, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 95% pure, more preferably at least about 98% pure, most preferably at least about 99% pure.

A further aspect of the present invention relates to a method of making the compounds according to formula (I). Furthermore, the present invention discloses synthetic methodologies for the preparation of amide, alkoxyamides, ketone, hydrazine, and oxime derivatives of thiazolidines, thiazolines, thiazoles, imidazolines, imidazoles, oxazolidines, oxazolines, and oxazoles.

To synthesize thiazoline and thiazole series compounds, L- or D-cysteine can be reacted with substituted or unsubstituted benzonitrile in methanol and pH 6.4 phosphate buffer solution at ambient temperature for several days (Bergeron et al., "Evaluation of Desferrithiocin and its Synthetic Analogs as Orally Effective Iron Chelators," *J. Med. Chem.* 34:2072-8 (1991); Bergeron et al., "Desazadesmethyldesferrithiocin Analogues as Orally Effective Iron Chelators," *J. Med. Chem.* 42:95-108 (1999); Zamri et al., "An Improved Stereocontrolled Synthesis of Pyochelin, Siderophore of *Pseudomonas aeruginosa* and *Burkholderia cepacia*," *Tetrahedron* 56:249-256 (2000), each of which is hereby incorporated by reference in its entirety). The resulting carboxylic acid intermediates can be easily converted to corresponding Weinreb amides (Nahm et al., "N-Methoxy-N-methylamides as Effective Acylating Agents," *Tetrahedron Lett.* 22:3815-18 (1981), which is hereby incorporated by reference in its entirety) using EDCI/HOBt as coupling reagents. Thiazole intermediates can be obtained from BrCCl$_3$/DBU dehydrogenation of the Weinreb amides. The thiazole intermediates can be reacted with appropriate lithium reagents or Grignard reagents (i.e., bearing the corresponding "C" ring, see Scheme 3 infra) in anhydrous THF to give the final thiazoles (Nahm et al., "N-Methoxy-N-methylamides as Effective Acylating Agents," *Tetrahedron Lett.* 22:3815-18 (1981), which is hereby incorporated by reference in its entirety). Alternatively, the thiazoline Weinreb amides can be reacted directly with appropriate lithium reagents or Grignard reagents, after quenching with saturated NH$_4$Cl solution, which affords mixtures of thiazoline compounds and the corresponding thiazole compounds.

Figure 2:
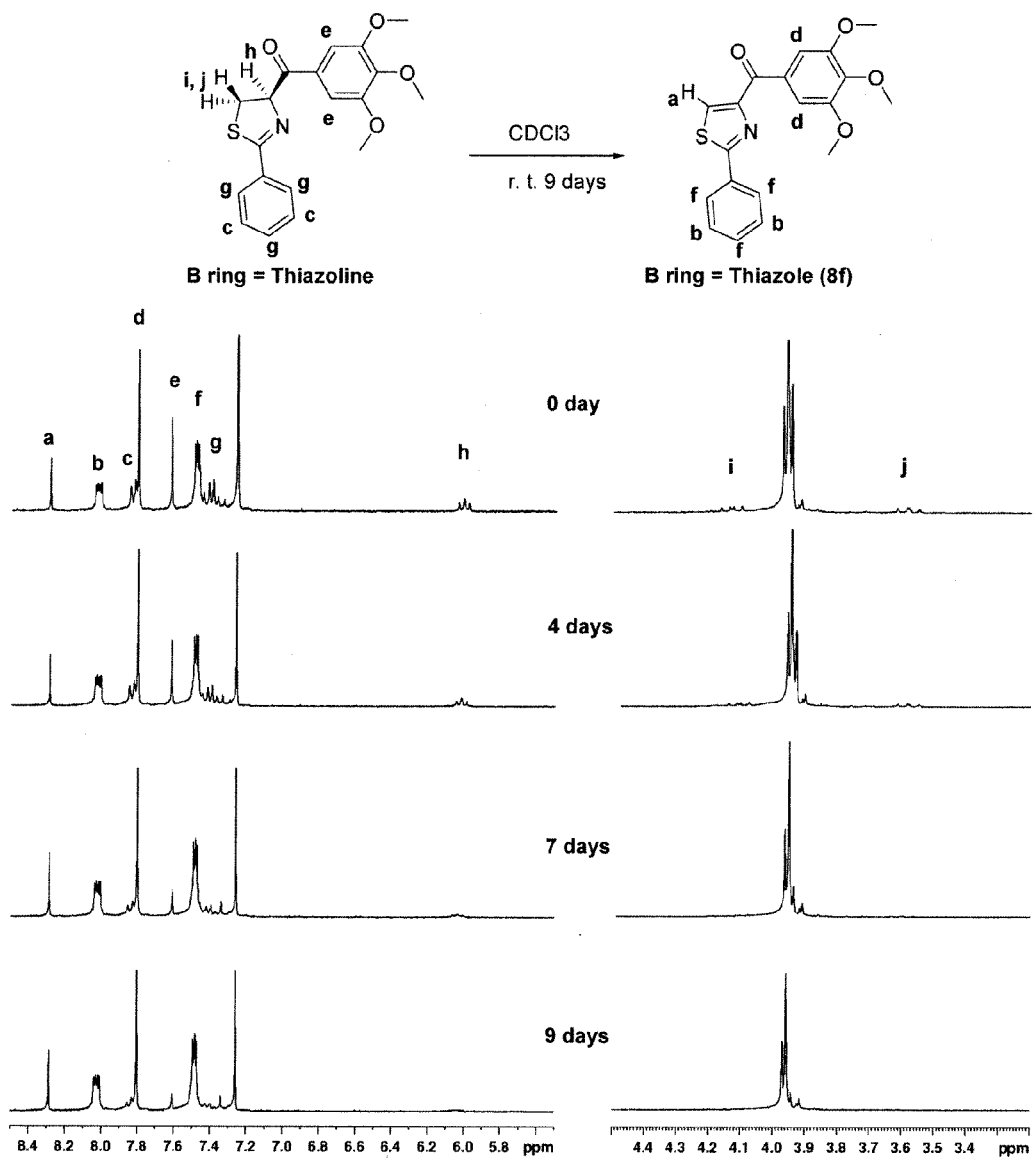
FIG. 2 illustrates NMR studies measuring the auto-dehydrogenation from thiazoline to thiazole compound 8f. At 0 day, NMR sample contained thiazoline and thiazole mixtures in $CDCl_3$; ratio is about 3:2. At 9th day, thiazoline compound was nearly completely converted to thiazole compound 8r.

When thiazoline/thiazole mixtures were placed in the solvent and exposed to air under ambient atmosphere for some time (overnight to several days), the thiazoline ring spontaneously dehydrogenated to thiazoles. As an example, in solution with deuterated chloroform, mixtures of thiazoline/thiazole compounds can be slowly converted to almost pure thiazole compounds after roughly 9 days (see, e.g., FIG. 2).

Formation of thiazolidine compounds is described in U.S. Pat. No. 7,307,093 to Miller et al. and U.S. Patent Application Publ. No. 2007/0155807 to Miller et al., each of which is hereby incorporated by reference in its entirety.

Oxazoline derivatives (carboxylic acids, carboxamides, methanones) according to the present invention are prepared via condensation of imine derivatives (benzonitrile and 1-phenyl-2-methoxy-ethanimine) with enantioneric (L or D) or racemic cysteine or serine ester while using triethylamine as a base (Meyer et al., *Tetrahedron: Asymmetry* 14:2229-2238 (2003), which is hereby incorporated by reference in its entirety)

Imidazoline derivatives are prepared using L-tartaric acid in a condensation reaction with substituted or unsubstituted arylaldehyde to form the imidazoline ring system (Anderson et al., *J. Med. Chem.* 32(1), 119-127 (1989), which is hereby incorporated by reference in its entirety).

Syntheses of thiazole, oxazole, and imidazole can be carried out by dehydrogenation of corresponding thiazoline, oxazoline, and imidazoline. Dehydrogenation according to the present invention can be achieved by initial halogenation of these core ring systems (thiazoline, imidazoline, and oxazoline) followed by elimination to yield the desired thiazole, oxazole, and imidazole derivatives.

Formation of thiocarbonyl linker group (from carbonyl) can be carried out using Lawesson's reagent (Jesberger et al., *Synthesis* 1929-1958 (2003), which is hereby incorporated by reference in its entirety). The thioketone structure with conjugated aromatic rings is stable relative to unhindered thioketones.

The carbonyl linker group can also be reduced to an alcohol using Grignard reaction of an intermediate aldehyde with according Grignard reagents. Alternatively, the carbonyl group can be completely removed with Clemmensen reduction to form the corresponding hydrocarbon (e.g., methylene group). When carbonyl is reduced to an alcohol or methylene, the strong hydrogen acceptor C=O reverses to strong hydrogen donor O—H or hydrocarbon, which totally loses hydrogen bond effects.

The ester and carboxamide linkages can be prepare from the same intermediate acids used to form the ketone linkage, except that the reactants (acid and "C" ring precursor) are exposed to suitable conditions for formation of the respective ester (DCC, NMM) or amide (EDCI, HOBt, Et$_3$N) linkages. Carboxamide linkages are also taught in U.S. Pat. No. 7,307,093 to Miller et al. and U.S. Patent Application Publ. No. 2007/0155807 to Miller et al., each of which is hereby incorporated by reference in its entirety.

It is also appreciated that the compounds and synthetic intermediates of the present invention can be prepared by synthetic processes known to those skilled in the art. Functional groups of intermediates and compounds of the present invention may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl (t-Boc or Boc), benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green et al., *Protective Groups in Organic Synthesis,* 2nd Ed., Wiley-Interscience (1991), which is hereby incorporated by reference in its entirety.

Another aspect of the present invention relates to a pharmaceutical composition including a pharmaceutically acceptable carrier and a compound according to the aspects of the present invention. The pharmaceutical composition can contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg·body wt. The preferred dosages comprise about 0.1 to about 100 mg/kg·body wt. The most preferred dosages comprise about 1 to about 100 mg/kg·body wt. Treatment regimen for the administration of the compounds of the present invention can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Yet another aspect of the present invention relates to a method of treating cancer that includes selecting a subject in need of treatment for cancer, and administering to the subject a pharmaceutical composition comprising a compound according to the first aspect of the present invention and a pharmaceutically acceptable carrier under conditions effective to treat cancer.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The compounds of the present invention are useful in the treatment or prevention of various forms of cancer, particularly prostate cancer, breast cancer, ovarian, skin cancer (e.g., melanoma), lung cancer, colon cancer, leukemia, renal cancer, CNS cancer (e.g., glioma, glioblastoma). Treatment of these different cancers is supported by the Examples herein. Moreover, based upon their believed mode of action as tubulin inhibitors, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

Thus, a further aspect of the present invention relates to a method of destroying a cancerous cell that includes: providing a compound of the present invention and then contacting a cancerous cell with the compound under conditions effective to destroy the contacted cancerous cell. According to various embodiments of destroying the cancerous cells, the cells to be destroyed can be located either in vivo or ex vivo (i.e., in culture).

A still fiber aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to another embodiment, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

As used herein, subject or patient refers to any mammalian patient, including without limitation, humans and other primates, dogs, cats, horses, cows, sheep, pigs, rats, mice, and other rodents.

When the compounds or pharmaceutical compositions of the present invention are administered to treat or prevent a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

EXAMPLES

The Examples set forth below are for illustrative purposes only and are not intended to limit, in any way, the scope of the present invention.

All reagents were purchased from Sigma-Aldrich Chemical Co., Fisher Scientific (Pittsburgh, Pa.), AK Scientific (Mountain View, Calif.), Oakwood Products (West Columbia, S.C.), etc. and were used without further purification. Moisture-sensitive reactions were carried under an argon atmosphere. Routine thin layer chromatography (TLC) was performed on aluminum backed Uniplates. (Analtech, Newark, Del.). Melting points were measured with Fisher-Johns melting point apparatus (uncorrected). NMR spectra were obtained on a Bruker ARX 300 (Billerica, Mass.) spectrometer or Varian Inova-500 spectrometer. Chemical shifts are reported as parts per million (ppm) relative to TMS in $CDCl_3$. Mass spectral data was collected on a Bruker ESQUIRE electrospray/ion trap instrument in positive and negative ion modes. Elemental analyses were performed by Atlantic Microlab Inc., (Norcross, Ga.).

Example 1

Synthesis of Thiazole, Thiazoline, and Thiazolidine Carboxamides

The synthesis of thiazole and thiazolidine carboxamides is generally disclosed in U.S. Pat. No. 7,307,093 to Miller et al. and U.S. Patent Application Publ. No. 2007/0155807 to Miller et al., each of which is hereby incorporated by reference in its entirety. The synthesis of various thiazole, dihydrothiazole, and thiazolidine carboxamides of the present invention is also illustrated in Scheme 1 below.

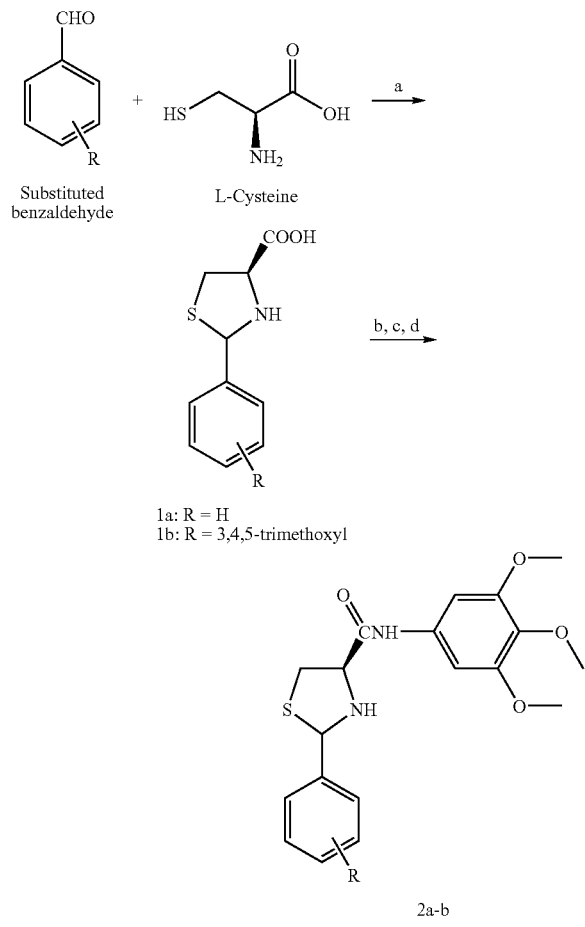

Reagents and conditions: (a) $C_2H_5OH$, $H_2O$, r.t.; (b) $Boc_2O$, 1 N NaOH, 1,4-dioxane, $H_2O$; (c) EDCI, HOBt, TEA, 3,4,5-trimethoxyaniline; (d) TFA, $CH_2Cl_2$.

General Procedure for the preparation of (2RS,4R)-2-Aryl-thiazolidine-4-carboxylic 1: A mixture of L-cysteine (3.16 g, 26.11 mmol) and appropriate aldehyde (26.15 mmol) in ethanol (300 mL) and water (30 mL) was stirred at room temperature for 6-15 h, and the solid that precipitated out was collected, washed with diethyl ether, and dried to afford the according (2RS,4R)-2-aryl-thiazolidine-4-carboxylic acid 1 with yields of 70-99%. At 0° C., 1 (5.95 mmol) was dissolved in 1N NaOH (6 mL) and 1,4-dioxane (15 mL), then di-tert-butyldicarbonate (2.80 g, 12.80 mmol) was added slowly and stirred at room temperature for 1 h. The reaction mixture was concentrated in vacuum and washed with ethyl acetate (20 mL). The aqueous phase was adjusted to pH=4 by adding 1N HCl or 5% $KHSO_4$, then extracted with ethyl acetate, dried with magnesium sulfate, filtered and concentrated on vacuum to give corresponding BOC protected acids as white foam-solids, which were used for next step without further purification.

General Procedure for the preparation of (2RS,4R)-2-Aryl-N-(3,4,5-trimethoxyphenyl)thiazolidine-4-carboxamides 2a, 2b: A mixture of appropriate BOC protected carboxylic acids (0.3-0.5 g), EDCI (1.2 equiv) and HOBT (1.05 equiv) in $CH_2Cl_2$ (20 mL) was stirred at room temperature for 10 min. To this solution, 3,4,5-trimethoxyaniline (1.05 equiv) and $Et_3N$ (1.2 equiv) were added and stirring continued at room temperature for 6-8 h. The reaction mixture was diluted with $CH_2Cl_2$ (30 mL) and sequentially washed with water, satd. $NaHCO_3$, brine and dried over $MgSO_4$. The solvent was removed under reduced pressure to yield a crude oil, which were stirred with TFA (0.6-1 mL) in 20 mL $CH_2Cl_2$ at r. t for 1-8 h to cleave the BOC group. The reaction mixture was concentrated, washed with satd. $NaHCO_3$ and dried over $MgSO_4$. The solvent was removed to yield a crude solid, and compounds 2a-2b were purified by column chromatography. Yield was reported as 2 steps yield.

(2RS,4R)-2-Phenyl-N-(3,4,5-trimethoxyphenyl)thiazolidine-4-carboxamide (compound 2a): Yield: 69.5. M.p. 158-159° C. $^1$H NMR (300 MHz, $CDCl_3$) δ 9.14 (s, 0.8H), 8.61 (s, 0.2H), 7.58-7.32 (m, 5H), 6.90 (s, 1.6H), 6.71 (s, 0.4H), 5.71 (dd, 0.2H, J=9.0 Hz), 5.42 (dd, 0.8H, J=11.7 Hz), 4.53 (dt, 0.8H), 4.19 (m, 0.2H), 3.87, 3.80 (s, s, 6H), 3.82, 3.78 (s, s, 3H), 3.80-3.78 (m, 0.4H), 3.62-3.42 (m, 1.6H), 2.96 (t, 0.2H, S=9.0 Hz), 2.74 (dd, 0.8H, J=11.7 Hz). MS (ESI) m/z 375.1 [M+H]$^+$, 397.1 [M+Na]$^+$. Anal. ($C_{19}H_{22}N_2O_4S$) C, F, N.

(2RS,4R)—N,2-bis(3,4,5-trimethoxyphenyl)thiazolidine-4-carboxamide (compound 2b): Yield: 34.5%. M.p. 147-149° C. $^1$H NMR (300 MHz, $CDCl_3$) δ 9.10 (s, 0.7H), 8.59 (s, 0.3H), 6.90 (s, 1.4H), 6.80 (s, 0.6H), 6.74 (s, 1.4H), 6.71 (s, 0.6H), 5.66 (br, 0.3H), 5.35 (d, br, 0.7H, J=7.5 Hz), 4.52 (br, 0.7H), 4.21 (br, 0.3H), 3.90, 3.87, 3.86, 3.84, 3.82, 3.81, 3.79, 3.78 (all s, 18H), 3.66-3.61, 3.54-3.38 (m, 1.6H), 2.98, 2.72 (br, 1H). MS (ESI) m/z 465.1 [M+H]$^+$, 487.1 [M+Na]$^+$. Anal. ($C_{22}H_{28}N_2O_7S$) C, H, N.

To enhance the activity and to develop more selective agents, this synthesis was extended and, as discussed in the subsequent examples, biological studies were performed to examine the nature of the substituents attached to the carbonyl at the 4 position. The synthesis of these additional compounds is shown in Scheme 2 below,

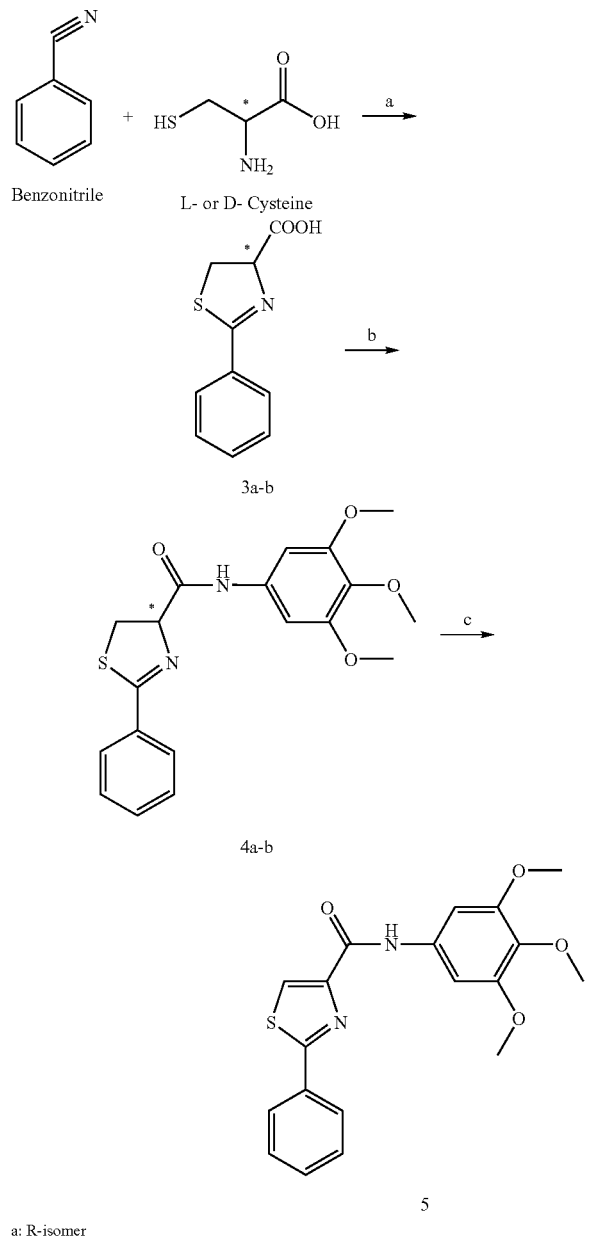

a: R-isomer
b: S-isomer

Reagents and conditions: (a) MeOH/pH=6.4 phosphate buffer, r.t.; (b) EDCI, HOBt, TEA, 3,4,5-trimethoxyaniline; (c) CBrCl₃, DBU.

Synthesis of 2-Phenyl-N-(3,4,5-trimethoxyphenyl)-4,5-dihydrothiazole-4-carboxamides 4a-4-b, 5: Substituted benzonitrile (40 mmol) was combined with L- or D-Cysteine (45 mmol) in 100 mL of 1:1 MeOH/pH6.4 phosphate buffer solution. The reaction was stirred at 40° C. for 3 days (Bergeron et al., "Evaluation of Desferrithiocin and its Synthetic Analogs as Orally Effective Iron Chelators," *J. Med. Chem.* 34:2072-8 (1991), which is hereby incorporated by reference in its entirety). Precipitate was removed through filtration, and MeOH was removed using rotary evaporation. The remaining solution was added 1M HCl to adjust pH=4 under 0° C. The resulting precipitate was extracted into $CH_2Cl_2$, dried and concentrated (Scheme 2). The carboxylic acids 3a, 3b were reacted with 3,4,5-trimethoxyaniline using the same procedures as described for preparation of compounds 2a, 2b, thereby forming compounds 4a, 4b. Conversion of the dihydrothiazoles 4a, 4b to the thiazolidine 5 was carried out by oxidation with $BrCCl_3$/DBU (Williams et al., "Studies of Mild Dehydrogenations in Heterocyclic Systems," *Tetrahedron Lett.* 38:331-334 (1997), which is hereby incorporated by reference in its entirety).

(4R)-2-Phenyl-4,5-dihydrothiazole-4-carboxylic acid (compound 3a): Yield: 58.3%. ¹H NMR (300 MHz, CDCl₃) δ 9.31 (br, 1H), 7.88-7.85 (m, 2H), 7.55-7.41 (m, 3H), 5.38 (t, 1H, 19.6 Hz), 3.75 (dt, 2H, J=9.6 Hz, 2.7 Hz). MS (ESI) m/z 162.0 [M−COOH]⁻.

(4S)-2-Phenyl-4,5-dihydrothiazole-4-carboxylic acid (compound 3b): Yield: 53.9%. ¹H NMR (300 MHz, CDCl₃) δ 7.89-7.85 (m, 2H), 7.55-7.41 (m, 3H), 5.38 (t, 1H, J=9.3 Hz), 3.75 (dt, 2H, J=9.3 Hz, 2.7 Hz). MS (EST) m/z 162.0 [M−COOH]⁻.

(4R)-2-Phenyl-N-(3,4,5-trimethoxyphenyl)-4,5-dihydrothiazole-4-carboxamide (compound 4a): Yield: 98.7%. M.p. 121-122° C. ¹H NMR (300 MHz, CDCl₃) δ 8.98 (s, 1H), 8.02-7.94, 7.62-7.48 (m, 5H), 6.93 (s, 2H), 5.38 (t, 1H, J=9.6 Hz), 3.92-3.85 (m, 2H), 3.87 (s, 6H), 3.82 (s, 3H). MS (ESI) m/z 373.1 [M+H]⁺. Anal. ($C_{19}H_{20}N_2O_4S$) C, H, N.

(4R)-2-Phenyl-N-(3,4,5-trimethoxyphenyl)-4,5-dihydrothiazole-4-carboxamide (compound 4b): Yield: 70.7%. M.p. 122-123° C. ¹H NMR (300 MHz, CDCl₃) δ 8.62 (s, 1H), 7.93-7.90 (m, 2H), 7.55-7.45 (m, 3H), 6.88 (s, 2H), 5.31 (t, 1H, J=9.6 Hz), 3.86 (s, 6H), 3.79 (s, 3H), 3.83-3.70 (m, 2H). MS (ESI) m/z 395.1 [M+Na]⁺, 370.9 [M−1]⁻. Anal. ($C_{19}H_{20}N_2O_4S$) C, H, N.

2-Phenyl-N-(3,4,5-trimethoxyphenyl)thiazole-4-carboxamide (compound 5): Yield: 89.7%. M.p. 157-158° C. ¹H NMR (300 MHz, CDCl₃) δ 9.30 (s, 1H), 8.20 (s, 1H), 8.04-8.01 (m, 2H), 7.53-7.51 (m, 3H), 7.08 (s, 2H), 3.92 (s, 6H), 3.86 (s, 3H). MS (ESI) m/z: 393.1 [M+Na]⁺. Anal. ($C_{19}H_{18}N_2O_4S$) C, H, N.

Example 2

Synthesis of Thiazole and Thiazolidine Methanone Derivatives 2-(substituted-phenyl)-4,5-dihydrothiazole-4-carboxylic acid methoxymethylamide intermediates: As shown in Scheme 3 below, 2-(substituted-phenyl)- and unsubstituted 2-phenyl-4,5-dihydrothiazole-4-carboxylic acids 3 were prepared from appropriate nitriles (e.g., benzonitrile, pyridinyl-nitrile, pyrimidinyl-nitrile, thiophene-yl-nitrile) and L-Cysteine as described above. The obtained carboxylic acids were then used for the synthesis of the methoxymethylamide intermediates. A mixture of appropriate the appropriate carboxylic acid 3 (5 mmol), EDCI (6 mmol) and HOBt (5 mmol) in $CH_2Cl_2$ (50 mL) was stirred for 10 min. To this solution, NMM (5 mmol) and $HNCH_3OCH_3$ (5 mmol) was added and stirring continued at room temperature for 6-8 hours. The reaction mixture was diluted with $CH_2Cl_2$ (100 mL) and sequentially washed with water, Satd. $NaHCO_3$, Brine and dried over $MgSO_4$. The solvent was removed under reduced pressure to yield a crude product 2, which was purified by column chromatography.

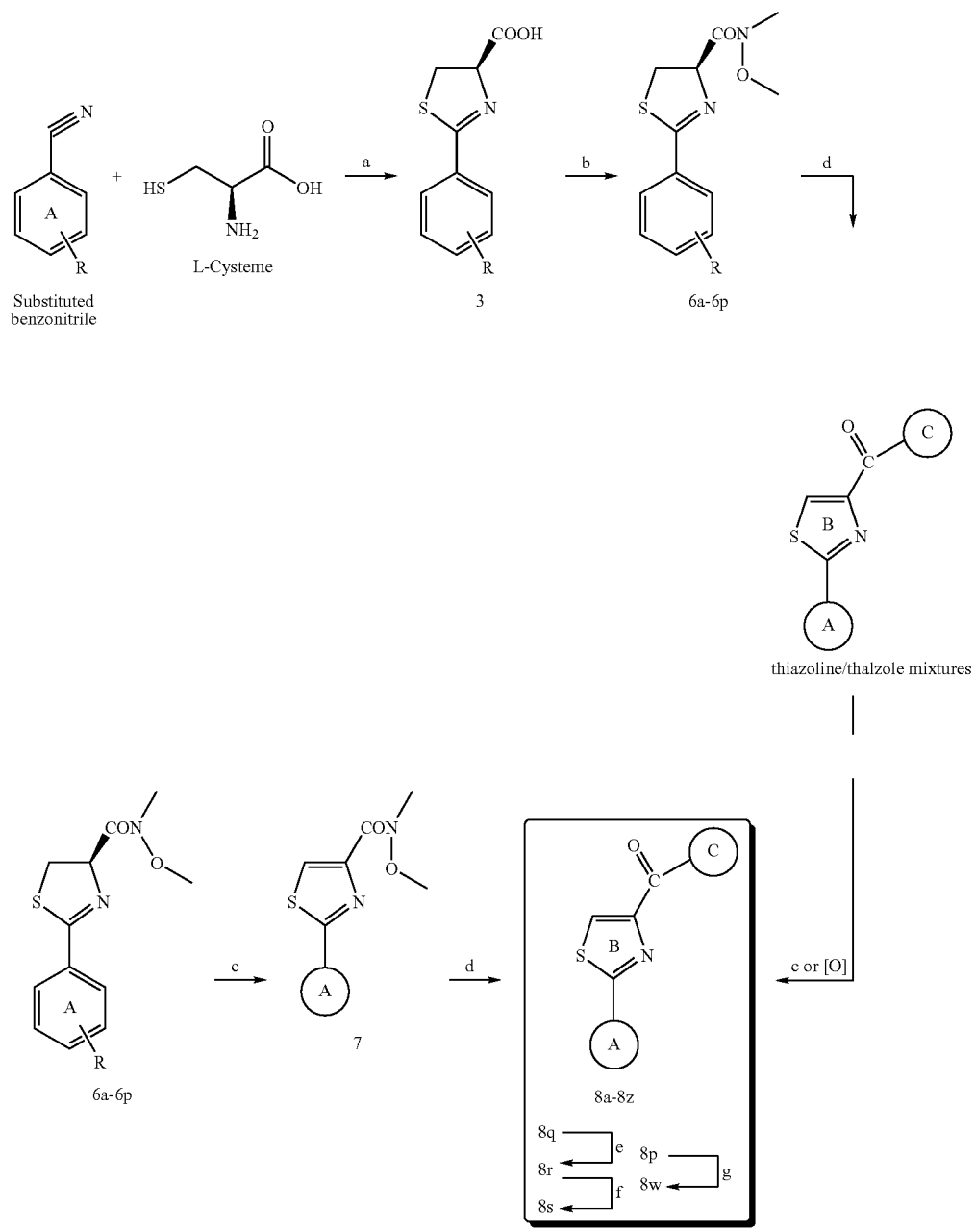
Scheme 3
R or A ring:
6a R = H
6b R = p-CH3
6c R = o-F
6d R = m-F
6e R = p-F
6f R = 3,4-dimethoxyl
6g R = p-NO2
6h R = p-CN
6i R = p-CF3
6j R = p-Br
6k R = p-C2H5
6l A ring = 4-pyridine
6m A ring = 2-pyrimidine
6p A ring = 2-thiophene -continued
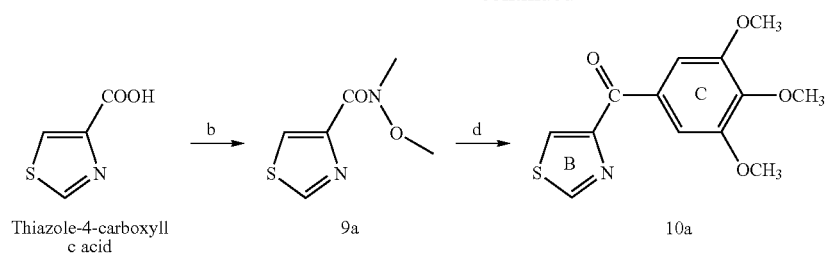
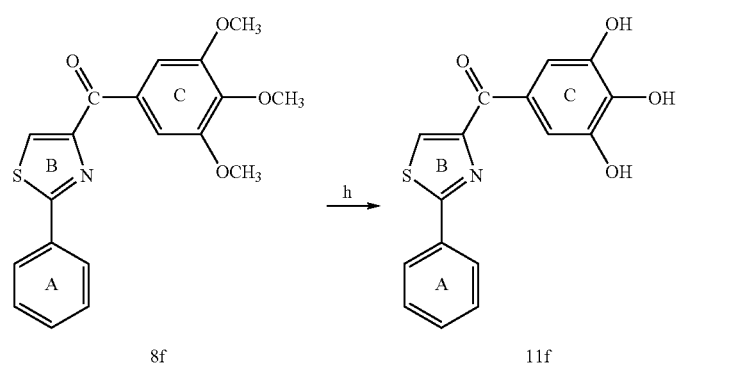
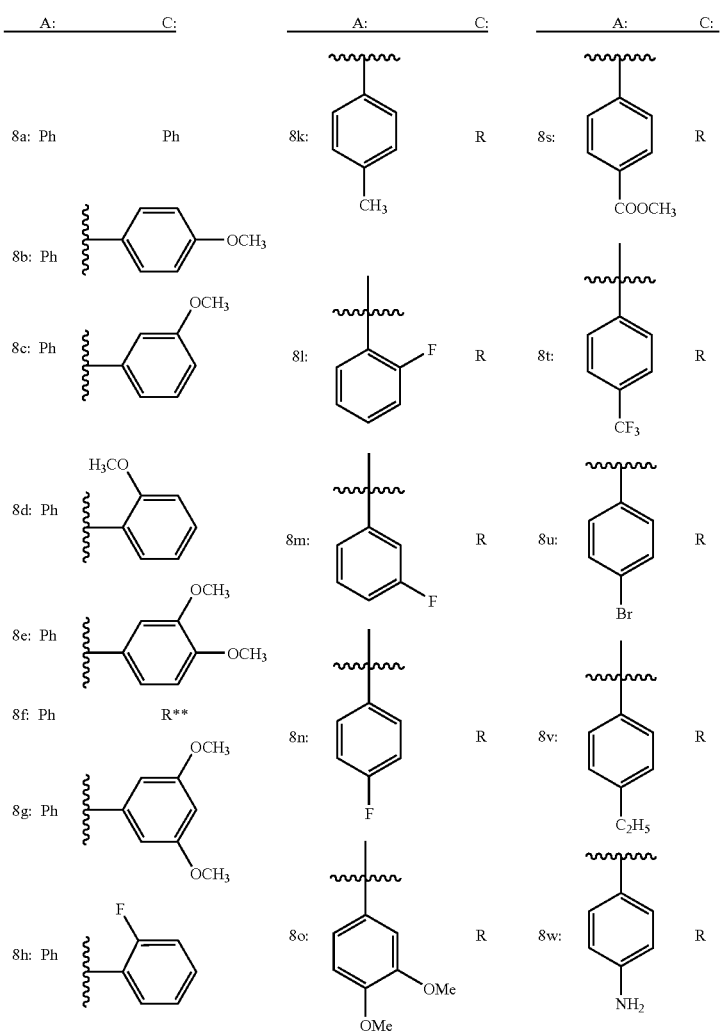

-continued

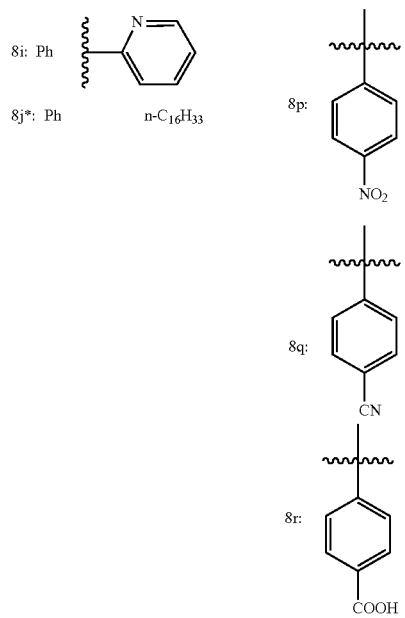
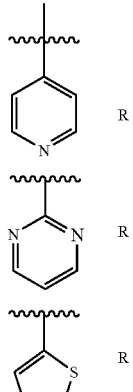

*Compound 8j contains a lipid at "C" position
** R = 3,4,5-trimethoxyphenyl

Reagents and conditions: (a) MeOH/pH=6.4 phosphate buffer, r. t.; (b) EDCI, HOBt, NMM, HNCH$_3$OCH$_3$; (c) CBrCl$_3$, DBU; (d) ArBr/BuLi or ArMgBr, THF; (e) HCl/HOAc; (f) MeOH/CH$_3$COCl; (g) Fe/HOAc; (h) BBr$_3$, CH$_2$Cl$_2$.

(R)—N-Methoxy-N-methyl-2-phenyl-4,5-dihydrothiazole-4-carboxamide (compound 6a). Yield: 92.0%. $^1$H NMR (300 MHz, CDCl$_3$) δ 7.85-7.83 (m, 2H), 7.48-7.36 (m, 3H), 5.66 (t, 1H, J=9.0 Hz), 3.90 (s, 3H), 3.88-3.80 (br, 1H), 3.55-3.47 (dd, 1H, J=10.8 Hz, 9.0 Hz), 3.30 (s, 3H). MS (ESI) m/z 251.0 [M+H]$^+$, 273.0 [M+Na]$^+$.

(R)—N-methoxy-N-methyl-2-p-tolyl-4,5-dihydrothiazole-4-carboxamide (compound 6b). Yield: 55.8%. $^1$H NMR (300 MHz, CDCl$_3$) δ 7.79 (d, 2H, J=7.8 Hz), 7.22 (d, 2H, J=7.8 Hz), 5.68 (t, 1H, J=8.7 Hz), 3.91 (s, 3H), 3.80 (t, 1H, J=9.3 Hz), 3.55 (t, 1H, J=9.3 Hz), 3.30 (s, 3H), 2.93 (s, 3H). MS (ESI) m/z 265.0 [M+H]$^+$, 287.0 [M+Na]$^+$.

(R)-2-(2-fluorophenyl)-N-methoxy-N-methyl-4,5-dihydrothiazole-4-carboxamide (compound 6c). Yield: 39.6%. $^1$H NMR (300 MHz, CDCl$_3$) δ 7.91 (dt, 1H, J=7.5 Hz, 1.8 Hz), 7.43 (m, 1H), 7.19-7.09 (m, 2H), 5.63 (t, 1H), 3.88 (s, 3H), 3.83 (hr, 1H), 3.48 (dd, 1H, J=11.1 Hz, 9.6 Hz), 3.30 (s, 3H). MS (ESI) m/z 291.0 [M+Na]$^+$.

(R)-2-(3-fluorophenyl)-N-methoxy-N-methyl-4,5-dihydrothiazole-4-carboxamide (compound 6d). Yield: 84.3%. $^1$H NMR (300 MHz, CDCl$_3$) δ 7.60-7.56 (m, 2H), 7.38 (dt, 1H, J=8.1 Hz, 6.0 Hz), 7.16 (dt, 1H, J=8.1 Hz, 2.4 Hz), 5.67 (t, 1H), 3.90 (s, 3H), 3.86-3.83 (br, 1H), 3.52 (dd, 1H, S=10.8 Hz, 9.3 Hz), 3.30 (s, 3H). MS (ESI) m/z 291.0 [M+Na]$^+$.

(R)-2-(4-fluorophenyl)-N-methoxy-N-methyl-4,5-dihydrothiazole-4-carboxamide (compound 6e). Yield: 66.0%. $^1$H NMR (300 MHz, CDCl$_3$) δ 7.90 (d, 2H), 7.13 (d, 2H), 5.63 (t, 1H), 3.88 (s, 3H), 3.83 (br, 1H), 3.46 (dd, 1H), 3.31 (s, 3H). MS (ESI) m/z 269.0 [M+Na]$^+$.

(R)-2-(3,4-dimethoxyphenyl)-N-methoxy-N-methyl-4,5-dihydrothiazole-4-carboxamide (compound 6f). Yield: 36.7%. $^1$H NMR (300 MHz, CDCl$_3$) δ 8.11 (d, 1H), 7.93 (s, 1H), 7.19-7.09 (d, 1H), 5.41 (t, 1H), 3.97 (s, 6H), 3.89 (s, 3H), 3.73 (br, 1H), 3.39 (dd, 1H), 3.31 (s, 3H). MS (ESI) m/z 333.1 [M+Na]$^+$.

(R)—N-methoxy-N-methyl-2-(4-nitrophenyl)-4,5-dihydrothiazole-4-carboxamide (compound 6g). Yield: 53.7%. $^1$H NMR (300 MHz, CDCl$_3$) δ 8.25 (d, 2H, J=9.0 Hz), 8.01 (d, 2H, S=9.0 Hz), 5.73 (t, 1H), 3.90 (s, 3H), 3.87 (br, 1H), 3.59 (dd, 1H, J=11.1 Hz, 9.3 Hz), 3.31 (s, 3H). MS (ESI) m/z 318.1 [M+Na]$^+$.

(R)-2-(4-cyanophenyl)-N-methoxy-N-methyl-4,5-dihydrothiazole-4-carboxamide (compound 6h). Yield: 26.7%. $^1$H NMR (300 MHz, CDCl$_3$) δ 7.94 (d, 2H, J=8.1 Hz), 7.69 (d, 2H, J=8.1 Hz), 5.71 (t, 1H, J=9.3 Hz), 3.89 (s, 3H), 3.87 (br, 1H), 3.56 (dd, 1H, J=10.8 Hz, 9.3 Hz), 3.30 (s, 3H). MS (ESI) m/z 298.0 [M+Na]$^+$.

(R)—N-methoxy-N-methyl-2-(4-trifluoromethylphenyl)-4,5-dihydrothiazole-4-carboxamide (compound 6i). Yield: 62.0%. $^1$H NMR (300 MHz, CDCl$_3$) δ 7.95 (d, 2H, J=8.1 Hz), 7.65 (d, 2H, J=8.1 Hz), 5.70 (t, 1H, J=9.6 Hz), 3.89 (s, 3H), 3.85 (br, 1H), 3.55 (dd, 1H, J=10.8 Hz, 9.6 Hz), 3.30 (s, 3H). MS (ESI) m/z 341.0 [M+Na]$^+$.

(R)-2-(4-bromophenyl)-N-methoxy-N-methyl-4,5-dihydrothiazole-4-carboxamide (compound 6j). Yield: 20.0%. $^1$H NMR (300 MHz, CDCl$_3$) δ 7.71, 7.53 (d, d, 4H, J=8.4 Hz), 5.63 (t, 1H, J=9.6 Hz), 3.88 (s, 3H), 3.84 (t, 1H, J=9.6 Hz), 3.52 (dd, 1H, J=10.8 Hz, 9.6 Hz), 3.30 (s, 3H). MS (ESI) m/z 351.0 [M+Na]$^+$.

(R)—N-methoxy-N-methyl-2-(4-ethyl)-4,5-dihydrothiazole-4-carboxamide (compound 6k). Yield: 77.7%. $^1$H NMR (300 MHz, CDCl$_3$) δ 7.75 (d, 2H, J=8.4 Hz), 7.21 (d, 2H, S=8.4 Hz), 5.64 (t, 1H), 3.89 (s, 3H), 3.81 (m, 1H), 3.48 (dd, 1H, J=10.8 Hz, 9.3 Hz), 3.29 (s, 3H), 2.67 (q, 2H), 1.24 (t, 3H). MS (ESI) m/z 301.0 [M+Na]$^+$.

(R)—N-methoxy-N-methyl-2-(pyridin-4-yl)-4,5-dihydrothiazole-4-carboxamide (compound 6l). Yield: 66.6%. $^1$H NMR (300 MHz, CDCl$_3$) δ 8.70 (d, 2H, J=9.0 Hz), 7.67 (d, 2H, J=9.0 Hz), 5.71 (d, 1H, J=9.6 Hz), 3.90 (s, 3H), 3.73 (t, 1H), 3.55 (dd, 1H, J=10.8 Hz, 9.6 Hz), 3.30 (s, 3H). MS (ESI) m/z 252.1 [M+H]⁺, 274.0 [M+Na]⁺.

(R)—N-methoxy-N-methyl-2-(pyrimidin-2-yl)-4,5-dihydrothiazole-4-carboxamide (compound 6m). Yield: 32.5%. $^1$H NMR (300 MHz, CDCl$_3$) δ 8.88 (d, 2H, J=4.8 Hz), 7.38 (t, H, J=4.8 Hz), 5.83 (t, 1H, J=9.0 Hz), 3.87 (s, 3H), 3.56 (dd, 2H, J=9.0 Hz), 3.30 (s, 3H). MS (ESI) m/z 275.0 [M+Na]⁺.

(R)—N-methoxy-N-methyl-2-(thiophen-2-yl)-4,5-dihydrothiazole-4-carboxamide (compound 6p). Yield: 58.5%. $^1$H NMR (300 MHz, CDCl$_3$) δ 7.57 (br, 1H), 7.49 (d, 1H, J=4.8 Hz), 7.09 (dd, 1H, J=3.6 Hz, 4.8 Hz), 5.64 (t, 1H, J=9.0 Hz), 3.90 (s, 3H), 3.85 (br, 1H), 3.57 (dd, 1H, J=9.9, 9.0 Hz), 3.29 (s, 3H). MS (ESI) m/z 279.0 [M+Na]⁺.

N-methoxy-N-methylthiazole-4-carboxamide (compound 9a): Yield: 58.7%. $^1$H NMR (300 MHz, CDCl$_3$) δ 8.82 (d, 1H, J=2.1 Hz), 8.10 (d, 1H, J=2.1 Hz), 3.79 (s, 3H), 3.45 (s, 3H). MS (ESI) m/z 194.9 [M+Na]⁺.

2-(Substituted-phenyl)-thiazole-4-carboxylic acid methoxymethylamides 7a-p: A solution of the resulting dihydrothiazole-4-carboxylic acid methoxymethylamides 6a-6p (1 equiv) in CH$_2$Cl$_2$ was cooled to 0° C., and distilled DBU (2 equiv) was added. Bromotrichloromethane (1.7 equiv) was then introduced dropwise via syringe over 10 min. The reaction mixtures were allowed to warm to room temperature and stirred overnight. Upon washing with satd. aqueous NH$_4$Cl (2×50 mL), the aqueous phase was extracted with EtOAc (3×50 mL). The combined organic layers were dried on MgSO$_4$, filtered and concentrated in vacuo. The residue was purified by flash chromatography as needed providing compounds 7a-p.

2-Phenyl-thiazole-4-carboxylic acid methoxymethylamide (compound 7a): Yield: 73.6%. $^1$H NMR (300 MHz, CDCl$_3$) δ 8.01 (s, 1H), 7.99-7.96 (m, 2H), 7.47-7.44 (m, 3H), 3.88 (s, 3H), 3.49 (s, 3H). MS (ESI) m/z 271.0 [M+Na]⁺.

(2-(substituted-phenyl)-thiazol-4-yl)-(substituted-phenyl)-methanones: As shown in Scheme 3 above, three different methods were utilized for the synthesis of the methanones 8a-8z.

Method 1: To a solution of n-BuLi (1.6M, 0.713 mL) in 8 mL THF was added a solution of 3,4,5-trimethoxybromobenzene (1.09 mmol) in 3 mL THF under −78° C. The mixture was stirred for 2 h and a solution of amides 6 or 7 (1.14 mmol) in 3 mL THF was charged. The mixture was allowed to warm to room temperature and stirred overnight. The reaction mixture was quenched with satd. NH$_4$Cl, extracted with ethyl ether, dried with MgSO$_4$, and exposed in air atmosphere overnight. The solvent was removed under reduced pressure to yield a crude product, which was purified by column chromatography to obtain pure compounds 8a-8z.

Method 2: To a solution of corresponding Grignard reagents (0.5M, 3 mL) in 2 mL THF was charged a solution of amides 6 or 7 (1 mmol) in 3 mL THF at 0° C. The mixtures were stirred for 30 min to 2 hours until amides disappeared on TLC plates. The reaction mixture was quenched with satd. NH$_4$Cl, extracted with ethyl ether, dried with MgSO$_4$ and to set in air atmosphere overnight to yield 6 as starting material. The solvent was removed under reduced pressure to yield a crude product, which was purified by column chromatography to obtain pure compound 8a-8z.

Hydrochloride salts of compounds 8i, 8x, and 8w were also prepared. At 0° C., to a solution of 10 mL HCl in ethyl ether (2 M) solution was added 8i, 8x or 8w (100 mg) in 5 mL CH$_2$Cl$_2$ (5 mL) and stirred overnight. The hydrochloride precipitate was filtered and washed with ethyl ether. Dying under high vacuum yielded the corresponding salts.

Phenyl (2-phenylthiazol-4-yl)-methanone (compound 8a): Yield: 76.3%. M.p. 65-66° C. $^1$H NMR (300 MHz, CDCl$_3$) δ 8.32-8.29 (m, 2H), 8.24 (s, 1H), 8.04-8.00 (m, 2H), 7.64-7.52 (m, 3H), 7.50-7.46 (m, 3H). MS (ESI) m/z 288.0 [M+Na]⁺. Anal. (C$_{16}$H$_{11}$NOS) C, H, N.

(4-Methoxyphenyl)(2-phenylthiazol-4-yl)-methanone (compound 8b): Yield: 74.8%. M.p. 105-106° C. $^1$H NMR (300 MHz, CDCl$_3$) δ 8.41 (d, 2H), 8.22 (s, 1H), 8.02 (dd, 2H), 7.47 (m, 3H), 7.01 (d, 2H), 3.80 (s, 3H). MS (ESI) m/z 318.1 [M+Na]⁺. Anal. (C$_{17}$H$_{13}$NO$_2$S) C, H, N.

(3-Methoxyphenyl)(2-phenylthiazol-4-yl)-methanone (compound 8c): Yield: 58.8%. M.p. 43-44° C. $^1$H NMR (300 MHz, CDCl$_3$) δ 8.23 (s, 1H), 8.05-8.01 (m, 2H), 7.93 (d, 1H), 7.84 (m, 1H), 7.49-7.40 (m, 4H), 7.16-7.15 (m, 1H), 3.89 (s, 3H). MS (ESI) m/z 318.1 [M+Na]⁺. Anal. (C$_{17}$H$_{13}$NO$_2$S) C, H, N.

(2-Methoxyphenyl)(2-phenylthiazol-4-yl)-methanone (compound 8d): Yield: 57.4%. Colorless oil. $^1$H NMR (300 MHz, CDCl$_3$) δ 8.03 (s, 1H), 7.98-7.95 (m, 2H), 7.57-7.47 (m, 2H), 7.47-7.42 (m, 3H), 7.08-7.01 (m, 2H), 3.78 (s, 3H). MS (ESI) m/z 318.1 [M+Na]⁺. Anal. (C$_{17}$H$_{13}$NOS) C, H, N.

(3,4-Dimethoxyphenyl)(2-phenylthiazol-4-yl)-methanone (compound 8e): Yield: 15.3%. M.p. 89-91° C. $^1$H NMR (500 MHz, CDCl$_3$) δ 8.24 (s, 1H), 8.22 (dd, 1H, J=8.5 Hz, 2.0 Hz), 8.04-8.02 (m, 2H), 7.99 (d, 1H, J=2.0 Hz), 7.49-7.47 (m, 3H), 6.98 (d, 1H, J=8.5 Hz), 3.99 (s, 6H). MS (ESI) m/z 348.0 [M+Na]⁺. Anal. (C$_{18}$H$_{15}$NO$_3$S) C, H, N.

(2-Phenyl-thiazol-4-yl)-(3,4,5-trimethoxy-phenyl)-methanone (compound 8f): Yield: 27.3%. M.p. 133-135° C. $^1$H NMR (300 MHz, CDCl$_3$) δ 8.29 (s, 1H), 8.03 (q, 2H), 7.80 (s, 2H), 7.49-7.47 (m, 3H), 3.96 (s, 6H), 3.97 (s, 3H). MS (ESI) m/z 378.1 [M+Na]⁺. Anal. (C$_{19}$H$_{17}$NO$_4$S) C, H, N.

(3,5-Dimethoxyphenyl)(2-phenylthiazol-4-yl)-methanone (compound 8g): Yield: 41.5%. M.p. 84-85° C. $^1$H NMR (300 MHz, CDCl$_3$) δ 8.23 (s, 1H), 8.04-8.01 (m, 2H), 7.99 (d, 2H, J=2.4 Hz), 7.49-7.43 (m, 3H), 6.72 (t, 1H, J=2.4 Hz), 3.87 (s, 6H). MS (EST) m/z 348.3 [M+Na]⁺. Anal. (C$_{18}$H$_{15}$NO$_3$S) C, H, N.

(2-Fluorophenyl)(2-phenylthiazol-4-yl)-methanone (compound 8h): Yield: 66.4%. M.p. 77-79° C. $^1$H NMR (300 MHz, CDCl$_3$) δ 8.48-8.41 (m, 2H), 8.28 (s, 2H), 8.04-7.98 (m, 2H), 7.50-7.46 (m, 3H), 7.26-7.16 (m, 2H). MS (ESI) m/z 306.0 [M+Na]⁺, 283.9 [M−H]⁻. Anal. (C$_{16}$H$_{10}$FNOS) C, H, N.

(2-Phenylthiazol-4-yl)-(pyridin-2-yl)-methanone (compound 8i): Yield: 20.7%. M.p. 95-97° C. $^1$H NMR (300 MHz, CDCl$_3$) δ 9.01 (s, 1H), 8.77 (d, 1H, J=4.8 Hz), 8.28 (d, 1H, J=7.8 Hz), 8.08-8.05 (m, 2H), 7.92 (dt, 1H, J=7.8 Hz, 1.2 Hz), 7.52 (ddd, 1H, J=7.8 Hz, 4.8 Hz, 1.2 Hz), 7.48-7.46 (m, 3H). (compound 8i.HCl salt): Yield: 70.6% M.p. 105-107° C. $^1$H NMR (300 MHz, DMSO-d$_6$) δ 9.03 (s, 1H), 8.79 (d, 1H, J=4.8 Hz), 8.10 (br, 1H), 8.08 (br, 1H), 8.03-8.00 (m, 2H), 7.73-7.69 (m, 1H), 7.56-7.54 (m, 3H). MS (ESI) m/z 267.0 [M+H]⁺. Anal. (C$_{15}$H$_{10}$N$_2$OS, C$_{15}$H$_{10}$N$_2$OS.HCl) C, H, N.

1-(2-phenylthiazol-4-yl)-heptadecan-1-one (compound 8j): Yield: 66.4%. M.p. 63-64° C. $^1$H NMR (300 MHz, CDCl$_3$) δ 8.12 (s, 1H), 8.02-7.99 (m, 2H), 7.49-7.47 (m, 3H), 3.16 (t, 2H, J=7.5 Hz), 1.82-1.72 (m, 2H), 1.26 (s, 26H), 0.88 (t, 3H, J=6.9 Hz). MS (ESI) m/z 414.4 [M+H]⁺. Anal. (C$_{26}$H$_{39}$NOS) C, H, N.

(2-p-Tolylthiazol-4-yl)-(3,4,5-trimethoxyphenyl)-methanone (compound 8k): Yield: 53.2%. M.p. 116-119° C. $^1$H NMR (300 MHz, CDCl$_3$) δ 8.25 (s, 1H), 7.91 (d, 2H, J=8.1 Hz), 7.80 (s, 2H), 7.28 (d, 2H, J=8.1 Hz), 3.96 (s, 3H), 3.95 (s, 6H). MS (ESI) m/z 392.1 [M+Na]⁺. Anal. (C$_{20}$H$_{19}$NO$_4$S) C, H, N.

[2-(2-Fluorophenyl)-thiazol-4-yl]-(3,4,5-trimethoxyphenyl)-methanone (compound 8l): Yield: 39.6%. M.p. 90-102° C. $^1$H NMR (500 MHz, CDCl$_3$) δ 8.40 (s, 1H), 8.33 (dt, 1H, J=1.5 Hz, 8.0 Hz), 7.78 (s, 2H), 7.49-7.44 (m, 1H), 7.30-7.23

(m, 2H), 3.97 (s, 3H), 3.95 (s, 6H). MS (ESI) m/z 396.1 [M+Na]+. Anal. ($C_{19}H_{16}FNO_4S$) C, H, N.

[2-(3-Fluorophenyl)-thiazol-4-yl](3,4,5-trimethoxyphenyl)-methanone (compound 8m): Yield: 14.1%. M.p. 122-124° C. $^1$H NMR (300 MHz, CDCl$_3$) δ 8.31 (s, 1H), 7.79 (s, 2H), 7.76-7.74 (m, 2H), 7.45 (dt, 1H, J=6.0 Hz, 8.4 Hz), 7.18 (dt, 1H, J=1.8 Hz, 8.4 Hz), 3.97 (s, 3H), 3.96 (s, 6H). MS (ESI) m/z 396.1 [M+Na]+. Anal. ($C_{19}H_{16}FNO_4S$) C, H, N.

[2-(4-Fluorophenyl)-thiazol-4-yl]-(3,4,5-trimethoxyphenyl)-methanone (compound 8n): Yield: 40.2%. M.p. 153-155° C. $^1$H NMR (300 MHz, CDCl$_3$) δ 8.27 (s, 1H), 8.04-8.00 (dd, 2H, J=8.4 Hz, 5.7 Hz), 7.75 (s, 2H), 7.21-7.15 (t, 3H, J=8.4 Hz), 3.97 (s, 3H), 3.95 (s, 6H). MS (ESI) m/z 396.1 [M+Na]+. Anal. ($C_{19}H_{16}FNO_4S$) C, H, N.

[2-(3,4-Dimethoxyphenyl)-thiazol-4-yl]-(3,4,5-trimethoxyphenyl)-methanone (compound 8o): Yield: 46.6%. M.p. 145-147° C. $^1$H NMR (300 MHz, CDCl$_3$) δ 8.20 (s, 1H), 7.76 (s, 2H), 7.58-7.54 (m, 2H), 6.94 (d, 2H, J=8.1 Hz), 3.96 (s, 6H), 3.95 (s, s, 9H). MS (ESI) m/z 438.1 [M+Na]+. Anal. ($C_{21}H_{21}NO_6S·¼H_2O$) C, H, N.

[2-(4-Nitrophenyl)-thiazol-4-yl]-(3,4,5-trimethoxyphenyl)-methanone (compound 8p): Yield: 46.4%. M.p. 199-200° C. $^1$H NMR (300 MHz, CDCl$_3$) δ 8.38 (d, 2H, J=8.7 Hz), 8.34 (s, 1H), 8.20 (d, 2H, J=8.7 Hz), 7.73 (s, 2H), 3.98 (s, 3H), 3.95 (s, 6H). MS (ESI) m/z 423.1 [M+Na]+. Anal. ($C_{19}H_{16}N_2O_6S$) C, H, N.

4-[4-(3,4,5-Trimethoxybenzoyl)-thiazol-2-yl]-benzonitrile (compound 8q): Yield: 45.9%. M.p. 181-182° C. $^1$H NMR (300 MHz, CDCl$_3$) δ 8.37 (s, 1H), 8.13 (d, 2H, J=8.4 Hz), 7.78 (d, 2H, J=8.4 Hz), 7.72 (s, 2H), 3.97 (s, 3H), 3.94 (s, 6H). MS (ESI) m/z 403.1 [M+Na]+. Anal. ($C_{20}H_{16}N_2O_4S$) C, H, N.

4-[4-(3,4,5-Trimethoxybenzoyl)-thiazol-2-yl]-benzoic acid (compound 8r): Yield: 61.9%. M.p. >220° C. (dec.). $^1$H NMR (300 MHz, CDCl$_3$) δ 8.65 (s, 1H), 8.00 (d, d, 4H), 7.65 (s, 2H), 3.88 (s, 6H), 3.80 (s, 3H). MS (ESI) m/z 397.9 [M-H]−, 353.9 [M-COOH]−. Anal. ($C_{20}H_{17}NO_6S$) C, H, N.

Methyl-4-[4-(3,4,5-trimethoxybenzoyl)-thiazol-2-yl]-benzoate (compound 8s): Yield: 72.5%. M.p. 172-174° C. $^1$H NMR (300 MHz, CDCl$_3$) δ 8.35 (s, 1H), 8.12 (dd, 4H, J=8.4 Hz), 7.78 (s, 2H), 3.97 (s, 3H), 3.96 (s, 3H), 3.95 (s, 6H). MS (ESI) m/z 436.1 [M+Na]+. Anal. ($C_{21}H_{19}NO_6S$) C, H, N.

(2-(4-(Trifluoromethyl)-phenyl)-thiazol-4-yl)(3,4,5-trimethoxyphenyl)-methanone (compound 8t): Yield: 45.5%. M.p. 144-145° C. $^1$H NMR (300 MHz, CDCl$_3$) δ 8.35 (s, 1H), 8.14, 7.65 (d, d, 4H, J=8.1 Hz), 7.76 (s, 2H), 3.97 (s, 3H), 3.95 (s, 6H). MS (EST) m/z 446.1 [M+Na]+. Anal. ($C_{20}H_{16}F_3NO_4S$) C, H, N.

[2-(4-Bromophenyl)-thiazol-4-yl]-(3,4,5-trimethoxyphenyl)-methanone (compound 8u): Yield: 51.8%. M.p. 149-150° C. $^1$H NMR (300 MHz, CDCl$_3$) δ 8.28 (s, 1H), 7.89, 7.62 (c, d, 4H, J=8.1 Hz), 7.75 (s, 2H), 3.97 (s, 3H), 3.94 (s, 6H). MS (ESI) m/z 456.0, 458.0 [M+Na]+. Anal. ($C_{19}H_{16}BrNO_4S$) C, H, N.

[2-(4-Ethyl-phenyl)-thiazol-4-yl]-(3,4,5-trimethoxy-phenyl)-methanone (compound 8v): Yield: 40.0%. M.p. 86-87° C. $^1$H NMR (300 MHz, CDCl$_3$) δ 8.25 (s, 1H), 7.93, 7.31 (d, d, 4H, J=8.4 Hz), 7.81 (s, 2H), 3.97 (s, 3H), 3.95 (s, 6H). MS (ESI) m/z 406.1 [M+Na]+. Anal. ($C_{21}H_{21}NO_4S$) C, H, N.

[2-(4-Amino-phenyl)-thiazol-4-yl]-(3,4,5-trimethoxyphenyl)-methanone (compound 8w): Yield: 61.8%. M.p. 177-179° C. $^1$H NMR (300 MHz, CDCl$_3$) δ 8.14 (s, 1H), 7.82, 7.65 (d, d, 4H, J=8.4 Hz), 7.78 (s, 2H), 3.96 (s, 3H), 3.94 (s, 6H). (compound 8w.HCl salt): Yield: 50.1%. M.p. 166-169° C. $^1$H NMR (300 MHz, DMSO-d$_6$) δ 8.49 (s, 1H), 7.84, 6.94 (d, d, 4H, J=8.4 Hz), 7.62 (s, 2H), 3.86 (s, 3H), 3.79 (s, 6H). MS (ESI) m/z 393.1 [M+Na]+. Anal. ($C_{19}H_{18}N_2O_4S$, $C_{19}H_{19}N_2O_4S·HCl$) C, H, N.

[2-(Pyridin-4-yl)-thiazol-4-yl]-(3,4,5-trimethoxyphenyl)-methanone (compound 8x): Yield: 29.3%. M.p. 178-180° C. $^1$H NMR (300 MHz, CDCl$_3$) δ 8.77 (dd, 2H, J=6.0 Hz, 1.5 Hz), 8.40 (s, 1H), 7.87 (dd, 2H, J=6.0 Hz, 1.8 Hz), 7.75 (s, 2H), 3.98 (s, 3H), 3.95 (s, 6H). (compound 8x.HCl salt): Yield: 92.7%. M. p. 182-184° C. $^1$H NMR (300 MHz, CDCl$_3$) δ 8.85 (br, 2H), 8.52 (s, 1H), 8.22 (br, 2H), 7.66 (s, 2H), 3.98 (s, 3H), 3.94 (s, 6H). MS (ESI) m/z 379.1 [M+Na]+. Anal. ($C_{18}H_{16}N_2O_4S$, $C_{18}H_{16}N_2O_4S·HCl$) C, H, N.

[2-(Pyrimidin-2-yl)-thiazol-4-yl]-(3,4,5-trimethoxyphenyl)-methanone (compound 8y): Yield: 51.9%. M.p. 190-191° C. $^1$H NMR (300 MHz, CDCl$_3$) δ 8.88 (d, 2H, J=4.8 Hz), 8.44 (s, 1H), 7.73 (s, 2H), 7.37 (t, 1H, J=4.8 Hz), 3.95 (s, 3H), 3.94 (s, 6H). MS (ESI) m/z 380.1 [M+Na]+. Anal. ($C_{17}H_{15}N_3O_4S$) C, H, N.

[2-(Thiophen-2-yl)-thiazol-4-yl]-(3,4,5-trimethoxyphenyl)-methanone (compound 8z): Yield: 30.5%. M.p. 111-113° C. $^1$H NMR (300 MHz, CDCl$_3$) δ 8.25 (s, 1H), 7.90 (s, 2H), 7.58 (dd, 1H, J=3.6, 0.9 Hz), 7.46 (dd, 1H, J=5.4, 0.9 Hz), 7.12 (dd, 1H, J=5.4, 3.6 Hz), 3.98 (s, 6H), 3.97 (s, 3H). MS (ESI) m/z 384.1 [M+Na]+. Anal. ($C_{17}H_{15}NO_4S_2$) C, H, N.

Thiazol-4-yl-(3,4,5-trimethoxy-phenyl)-methanone (compound 10a): Yield: 49.4% M.p. 106-108° C. $^1$H NMR (300 MHz, CDCl$_3$) δ 8.92 (d, 1H, J=2.1 Hz), 8.34 (d, 1H, J=2.1 Hz), 7.61 (s, 2H), 3.94 (s, 3H), 3.93 (s, 6H). MS (ESI) m/z 302.0 [M+Na]+. Anal. ($C_{13}H_{13}NO_4S$) C, H, N.

Method 3: (2-Phenyl-thiazol-4-yl)-(3,4,5-trihydroxy-phenyl)-methanone (11f) was synthesized beginning with compound 8f. To a solution of compound 8f (123 mg, 0.35 mmol) in 5 mL anh. CH$_2$Cl$_2$ was added BBr$_3$ (1M solution in CH$_2$Cl$_2$, 1.75 mL, 5 mmol) under −78° C. The mixture was stirred for 2 h and a solution of amide 7 (1.14 mmol) in 3 mL THF was charged. The mixture was allowed to warm to room temperature slowly and stirred overnight. The reaction mixture was quenched with satd. NH$_4$Cl, extracted with ethyl acetate, dried with MgSO$_4$. The solvent was removed under reduced pressure to yield a crude product, which was purified by column chromatography to obtain pure compound as red crystalline solid. Yield: 50.9%. M.p. 175-176° C. $^1$H NMR (300 MHz, DMSO-d6) δ 8.44 (d, 1H), 8.07-8.04 (m, 2H), 7.57-7.55 (m, 3H), 7.33 (s, 2H). MS (ESI) m/z 336.1 [M+Na]+. Anal. ($C_6H_{11}NO_4S$) C, H, N.

Example 3

X-Ray Crystallography Structure Determination for Compound 8f

Compound 8f was recrystallized from hexane and ethyl acetate, and single colorless crystals suitable for X-ray diffraction were obtained. X-ray crystallographic data for 8f were collected from a single crystal mounted with paratone oil on a nylon cryoloop. Data were collected at 100K on a Bruker Proteum CCD area detector, controlled by Proteum2 software (Proteum2, Bruker AXS Inc., Madison, Wis., USA (2005)), using a rotating-anode generator and Osmic mirrors to generate Cu radiation (λ=1.54178 Å). The data were reduced using SAINT (SAINT, Bruker AXS Inc., Madison, Wis., USA. (1998)), with an absorption correction applied using SADABS (SADABS, Bruker AXS Inc., Madison, Wis., USA. (2000)) based on redundant reflections; this correction included a spherical component. The structure was solved using direct methods (SHELXS[x4]), which revealed all of the heavy atoms. Structure refinement with SHELXL (SHELXL-97, G. M. Sheldrick, University of Göttingen, Germany (1997)) was carried out using full-matrix methods based on $F^2$, and proceeded smoothly. Hydrogen atoms were added to the structural model assuming ideal C—H distances and isotropic ADPs constrained to be similar to that of the bonded carbon atom. In the final model, anisotropic ADPs were refined for all heavy atoms, and isotropic ADPs for chemically-similar hydrogens (e.g. methyl H) were constrained to be identical. The final refinement parameters are: wR2=0.084 for 228 parameters and 3066 independent observations, R1=0.031, S (goodness-of-fit)=1.057.

An ORTEP drawing of 8f with the atom labeling scheme is shown in FIG. 1. The X-ray structure showed that 8f molecule contained a conjugated system composed of three aromatic rings and a carbonyl group linker between "B" and "C" ring as expected ("A" ring=phenyl; "B" ring=thiazole; "C" ring=3,4,5-trimethoxyphenyl). As a result, two C—C bonds adjacent to C=O and C—C— bond between "A" phenyl and "B" thiazole ring display (C1-C7=1.496(2) Å; C7-C8=1.492 (2) Å; C10-C11=1.471(2) Å) shorter bond lengths than normal C—C single bond (1.54 Å) and longer than normal C=C double bond (1.34 Å) (see Table 1 below). Thus, conjugation of the π system is possible for "A", "B", "C" rings and carbonyl group. The carbonyl group is nearly coplanar with the adjacent "B" thiazole ring (O—C7-C1-C6 16.2(2)°, O—C7-C8-C9 9.7(2)°).

TABLE 1

Selected Geometric Parameters of Compound 8f (Å, °)

| | |
|---|---|
| C1-C7 | 1.496(2) |
| C7-O | 1.224(2) |
| C7-C8 | 1.492(2) |
| C8-C9 | 1.371(2) |
| C8-N | 1.380(2) |
| C9-S | 1.711(2) |
| S-C10 | 1.747(2) |
| C10-N | 1.303(2) |
| C10-C11 | 1.471(2) |
| C2-C1-C6 | 121.2(2) |
| C2-C1-C7 | 122.3(2) |
| C6-C1-C7 | 116.4(2) |
| O-C7-C8 | 118.0(2) |
| O-C7-C1 | 120.1(2) |
| C8-C7-C1 | 121.9(2) |
| C9-C8-N | 115.1(2) |
| C9-C8-C7 | 121.7(2) |
| N-C8-C7 | 123.0(2) |
| C8-C9-S | 110.0(1) |
| C9-S-C10 | 89.6(1) |
| N-C10-C11 | 123.5(2) |
| N-C10-S | 113.9(1) |
| C11-C10-S | 122.6(1) |
| C10-N-C8 | 111.4(2) |
| C12-C11-C10 | 122.3(2) |
| C16-C11-C10 | 118.5(2) |

Example 4

In Vitro Assays for Anticancer Cytotoxicity

In vitro assays were tested against both melanoma cell lines and prostate cancer cells lines. In each case, standard sulforhodamine B assay was used. Cells were seeded into 96-well plates at 1000 to 5000 cells/well depending on growth rates. After 12 hours, media were changed and serial dilutions of compounds were added. Cells were incubated with each compound for 48 hours. Fresh media containing the test compound were changed ever 24 hours. Thereafter, total cell protein corresponding to cell numbers (both viable and non-viable cells) were measured using the sulforhodamine B (SRB) assay according to manufacturer's protocol (Sigma-Aldrich, Inc.) (Rubinstein et al., "Comparison of in vitro Anticancer Drug-screening Data Generated with a Tetrazolium Assay Versus a Protein Assay Against a Diverse Panel of Human Tumor Cell Lines," *J. Natl. Cancer Inst.* 82:1113-1118 (1990); Dothager et al., "Synthesis and Identification of Small Molecules that Potently Induce Apoptosis in Melanoma Cells Through G1 Cell Cycle Arrest," *J. Am. Chem. Soc.* 127:8686-8696 (2005), each of which is hereby incorporated by reference in its entirety).

For melanoma assays, one human melanoma cell line (A375) and one mouse melanoma cell line (B16-F1) were used. A375 cells and B16-F1 cells were purchased from ATCC (American Type Culture Collection, Manassas, Va., USA). Fibroblast cells were used as a control to determine the selectivity of these compounds against melanoma. Human dermal fibroblast cells were purchased from Cascade Biologics, Inc., Portland, Oreg., USA. All cell lines were cultured in DMEM (Cellgro Mediatech, Inc., Herndon, Va., USA), supplemented with 5% FBS (Cellgro Mediatech), 1% antibiotic/antimycotic mixture (Sigma-Aldrich, Inc., St. Louis, Mo., USA) and bovine insulin (5 kg/ml; Sigma-Aldrich). Cultures were maintained at 37° C. in a humidified atmosphere containing 5% $CO_2$. Cells were exposed to a wide range of concentrations for 48 h in round-bottomed 96-well plates. Cells were fixed with 10% trichloroacetic acid and washed five times with water. After cells were air-dried overnight and stained with SRB solution, total proteins were measured at 560 nm with a plate reader. $IC_{50}$ (i.e., concentration which inhibited cell growth by 50% of no treatment controls) values were obtained by nonlinear regression analysis with GraphPad Prism (GraphPad Software, San Diego, Calif.).

For prostate cancer assays, four human prostate cancer cell lines (LNCaP, DU 145, PC-3, and PPC-1) were selected. LNCaP, PC-3 and DU 145 cells were purchased from ATCC (American Type Culture Collection, Manassas, Va., USA). Dr. Mitchell Steiner at University of Tennessee Health Science Center kindly provided PPC-1cells. All prostate cancer cell lines were cultured in RPMI 1640 (Cellgro Mediatech, Inc., Herndon, Va., USA), supplemented with 10% FBS (Cellgro Mediatech). Cultures were maintained at 37° C. in a humidified atmosphere containing 5% $CO_2$. 1000 to 5000 cells were plated into each well of 96-well plates depending on growth rate and exposed to different concentrations of a test compound for 96 h in three to five replicates. Cell numbers at the end of the drug treatment were measured by the SRB assay. Briefly, the cells were fixed with 10% of trichloroacetic acid and stained with 0.4% SRB, and the absorbances at 540 nm were measured using a plate reader (DYNEX Technologies, Chantilly, Va.). Percentages of cell survival versus drug concentrations were plotted and the $IC_{50}$ (concentration that inhibited cell growth by 50% of untreated control) values were obtained by nonlinear regression analysis using WinNonlin (Pharsight Corporation, Mountain View, Calif.).

The results of these assays are provided in Tables 2-4 below.

Modifications of the "B" ring from a thiazolidine to thiazole system and the linker from an amide to a ketone. In prior ATCAA compounds, the thiazolidine ring, which contained a free NH at its 3-position, was shown to be important for cytotoxicity. Once the "B" ring thiazolidine moiety was replaced by a thiazoline ring, the antiproliferative activity decreased sharply from 0.6 μM to over 50 μM on WM-164 cell lines (Li et al., "Synthesis and Antiproliferative Activity of Thiazolidine Analogs for Melanoma," *Bioorg. Med. Chem. Lett.* 17:4113-7 (2007), which is hereby incorporated by reference in its entirety). The ATCAA-1 fatty amide derivative that was most effective against melanoma and prostate cancer cell lines were examined and shown to have an $IC_{50}$ 0.4-2.2 µM (see Table 2). Replacement of the long fatty chain with a certain aromatic bulky subsistent such as fluorene (ATCAA-2) showed inhibitory activity on both cancer cell lines ($IC_{50}$=1.6-3.9 µM). The fluorene group in 4-carboxylic amide position was also replaced by 3,4,5-trimethoxylphenyl group (2a and 2b), but the potency against both cancer cell lines was lost. The subsequent "B" ring modification from saturated thiazolidine compound 2a to unsaturated thiazole 5 did not show any cytotoxicity against either cancer cell line tested. But thiazoline enantiomers 4a and 4b (R-isomer and S-isomer, with similar antiproliferative activities) showed improved activity ($IC_{50}$=3.4-38.3 µM) compared with 2a, 2b and 5. When the amide CONH linkage between "B" ring and "C" ring was replaced by a carbonyl linker, the mixtures of thiazoline/thiazole ketone 8f were obtained instead of desired thiazoline ketone, because the auto-dehydrogenation between thiazoline and thiazole occurred (the conversion was shown in FIG. 2). Surprisingly, introduction of the carbonyl group linker and thiazole "B" ring led to a significant enhancement of growth inhibition of examined cancer cell lines with a low nanomolar level (8f, $IC_{50}$=0.021-0.071 µM) that is comparable to the natural anticancer agent Colchicine. Consequently, a series of the related compounds with "B" as a thiazole ring were designed and synthesized based on the discovery of 8f. Their anticancer activity was also evaluated against melanoma and prostate cancer.

Modifications of the "C" ring also had significant effects. Variation of the phenyl substituents has a remarkable change in effect on potency. The in vitro assay results shown in Table 3 provide interesting results, but only the 3,4,5-trimethoxylphenyl "C" ring (8f) showed excellent inhibition against all cancer cells ($IC_{50}$=21-71 nM, average $IC_{50}$=41 nM). Compound 8g, with a 3,5-dimethoxyphenyl group, showed 6-fold average cytotoxicity lower than 8f against six different cell lines ($IC_{50}$=170-424 nM, calcd. average $IC_{50}$=261 nM). Modifications of 8f by removal of one methoxy at meta-position (8e) or two methoxy groups (8b, 8c and 8d) from 8f led to a dramatic loss in activity ($IC_{50}$>20 µM). Although ortho-substituted monomethoxy compound 8d exhibited weak activity against a certain cell lines compared with meta-/para-MeO substituted 8c/8b and dimethoxyphenyl compound 8e, none of them showed significant potency in inhibition compared with 8f. Similar trends were also seen in 8h and 8j with 2-fluorophenyl and hexadecyl in "C" ring modifications.

Modifications of the "A" ring using different para-substituted electron withdrawing groups (EWG) and electron donor groups (EDG) did not show clear influence on antiproliferative activity. Introduction of a weak EWG (4-F in 8n, $IC_{50}$ values: 6-43 nM) or weak EDG (4-CH$_3$ in 8k, $IC_{50}$s: 5-21 nM), both increased the potency compared with 8f (see Table 4). The replacement of para-position with strong EWG such as $NO_2$ (8p), CN (8q), $CF_3$ (8t) or introducing strong EDG (3,4-dimethoxy) to "A" phenyl ring (8o) exhibited comparable antiproliferative activity.

To compare the effects of ortho-, meta- and para-substitutions, a fluoro atom was introduced to different positions of "A" phenyl ring (8l, 8m, and 8n). The various o-, m-, p-substituents did not exhibit equal activities. p-Fluoro substituted 8n has the best activity for examined prostate cancer cells (6-13 nM) while o-fluoro substituted 8l showed the lowest $IC_{50}$ values (27-30 nM) against melanoma cells. 8n has similar average $IC_{50}$ values (33-43 nM) against melanoma compared with 8l. But o-fluoro substituted 8l has lowest potency ($IC_{50}$ values: 52-114 nM) among the three substituted compounds on prostate cancer cells. Meta-substituted compound 8m showed lowest activity on melanoma cells ($IC_{50}$ values: 287-304 nM) but showed moderate inhibition on prostate cancer cells ($IC_{50}$ values: 23-46 nM).

Turning to the effects of steric hindrance group on the "A" phenyl ring substituents, it was found that p-bromo (8u, $IC_{50}$ values: 18-44 nM) caused a decrease in antiproliferative activity relative to p-fluoro position (8n, $IC_{50}$ values: 6-12 nM) but only against prostate cancer cells. Reduced activity against both cancer cell lines occurred when p-methyl (8k, $IC_{50}$ values: 5-21 nM) was replaced with a p-ethyl group (8v, $IC_{50}$ values: 17-70 nM).

To investigate if the phenyl ring played an essential role at the "A" ring site, phenyl at 2-thiazole position was removed and compound 10 was obtained. This modification caused a total loss of activity compared with 8f. The replacement of the "A" ring by pyridine (compound 8x) had the same effect. Moreover, substituting 2-pyrimidine in "A" ring (compound 8y) also caused a significant loss of activity ($IC_{50}$s: 11.8-41.0 µM). However, introducing the thiophene replacement of phenyl (8z) into "A" position improved the potency calcd. 1-3 folds on all examined cell lines ($IC_{50}$s: 9-38 nM) compared to 8f ($IC_{50}$s: 21-71 nM).

Because many of the compounds show poor water-solubility, three water-soluble salts were prepared after introducing a hydrophilic group such as $NH_2$ (8w) and COOH (8r) into "A" ring to form HCl or sodium salts. Another modification is replacing "A"/"C" rings in 8a with pyridine (8i, 8x, 8y) or pyrimidine rings, which could also be converted into HCl salts. These modifications reduced the calculated LogP values (LogP=2.74-3.90) compared with 8a and 8f (LogP=4.46 and 4.08; see Table 5). Introducing p-amino to "A" phenyl (8w) is the only case to increase the antiproliferative activity (HCl salt, $IC_{50}$ values: 11-29 nM) compared with 8f against all cell lines. Although replacing phenyl with pyrimidine (8y) kept partial activity against both cancer cells, the potency range was markedly reduced from nM to µM compared with 8f. Unfortunately, introducing COOH to para-phenyl "A" ring and pyridine to "A" or "C" rings (8i, 8r, 8x) all resulted in the total loss of the anti-cancer activity. A total loss of potency was seen in the methyl ester 8s of acid 8r against both cancer cell lines. Demethylation of compound 8f afforded water soluble 3,4,5-trihydroxyphenyl at "C" ring compound 11f, but this demethylation results in complete loss of antiproliferative activity against all tested cancer cells, which also points out the importance of 3,4,5-trimethoxyphenyl at "C" position of the methanones.

Given these results, compound 8f was also subjected to in vitro testing in an NCI-60 screening assay, which measures the ability of the compound to act against six leukemia cell lines, eight non-small cell lung cancer cell lines, seven colon cancer cell lines, six CNS cancer (e.g., glioma/glioblastoma) cell lines, eight melanoma cell lines, six ovarian cancer cell lines, seven renal cancer cell lines, two prostate cancer cell lines, and eight breast cancer cell lines. The results of the NCI-60 assay showed broad activity against all of these cancers, with $GI_{50}$ values in the nanomolar range ($<1.0\times10^{-8}$) against most cell lines and TGI values in the micromolar range against most cell lines. TGI values in the nanomolar range were obtained against several leukemia cell lines, one lung cancer cell line, several colon cancer cell lines, several ovarian cancer cell lines, and several breast cancer cell lines.

TABLE 2

In Vitro Inhibitory Effects of Modified ATCAA Compounds against the Proliferation of Melanoma (A375, B16-F1) and Prostate Cancer Cells (DU145, PC-3, LNCaP, PPC-1)

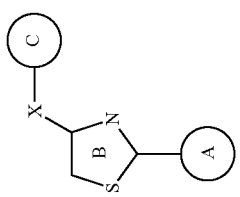

| | A ring | B ring[a] | C ring[b] | X | B16-F1 | A375 | DU 145 | PC-3 | LNCaP | PPC-1 |
|---|---|---|---|---|---|---|---|---|---|---|
| | | | | | | | IC$_{50}$ ± SEM (µM) | | | |
| ATCAA-1 | p-NHAc-Ph | TZD | C$_{16}$H$_{33}$ | CONH | 2.2 ± 0.3 | 2.1 ± 0.2 | 1.7 ± 0.1 | 1.2 ± 0.1 | 1.0 ± 0.1 | 0.4 ± 0.1 |
| ATCAA-2 | p-NHAc-Ph | TZD | 9H-fluoren-1-yl | CONH | 3.9 ± 0.3 | 2.1 ± 0.1 | 1.9 ± 0.3 | 2.1 ± 0.1 | 3.5 ± 0.7 | 1.6 ± 0.1 |
| 2a | Ph | TZD | 3,4,5-triMeO-Ph | CONH | >100 | >100 | >20 | >20 | >20 | >20 |
| 2b | 3,4,5-triMeO-Ph | TZD | 3,4,5-triMeO-Ph | CONH | >100 | >100 | >20 | >20 | >20 | >20 |
| 4a(4R) | Ph | TZL | 3,4,5-triMeO-Ph | CONH | 38.3 ± 3.2 | 22.8 ± 1.6 | >20 | >20 | >20 | 5.3 ± 0.3 |
| 4b(4S) | Ph | TZL | 3,4,5-triMeO-Ph | CONH | 30.4 ± 2.8 | 13.6 ± 1.2 | >20 | 13.2 ± 2.1 | 16.8 ± 1.8 | 3.4 ± 0.2 |
| 5 | Ph | TZ | 3,4,5-triMeO-Ph | CONH | >100 | >100 | >20 | >20 | >20 | >20 |
| 8f | Ph | TZ | 3,4,5-triMeO-Ph | CO | 0.055 ± 0.005 | 0.028 ± 0.005 | 0.071 ± 0.004 | 0.021 ± 0.001 | 0.028 ± 0.004 | 0.043 ± 0.005 |
| Colchicine | | | | | 0.029 ± 0.005 | 0.020 ± 0.003 | 0.010 ± 0.002 | 0.011 ± 0.001 | 0.016 ± 0.004 | 0.020 ± 0.001 |

[a]TZD = Thiazolidine, TZL = Thiazoline, TZ = Thiazole;
[b]For ATCAA-1, "C" position contains a lipid chain. ATCAA-1 and ATCAA-2 were prepared using appropriate starting materials according to Scheme 1 of Example 1 (see also Li et al., "Synthesis and Antiproliferative Activity of Thiazolidine Analogs for Melanoma," Bioorg. Med. Chem. Lett. 17:4113-7 (2007); Gududuru et al., "Discovery of 2-Arylthiazolidine-4-Carboxylic Acid Amides as a New Class of Cytotoxic Agents for Prostate Cancer," J. Med. Chem. 48:2584-2588 (2005), each of which is hereby incorporated by reference in its entirety).

TABLE 3

In Vitro Growth Inhibitory Effects of Compounds 8a-8j with Different "C" Rings against Proliferation of Melanoma (A 375, B16-F1) and Prostate Cancer Cells (DU145, PC-3, LNCaP, PPC-1)

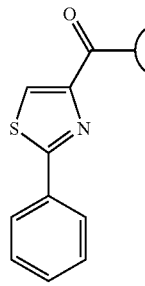

| Compounds 8 | | C Ring | IC$_{50}$ ± SEM (µM) | | | | | |
|---|---|---|---|---|---|---|---|---|
| | | | B16-F1 | A375 | DU 145 | PC-3 | LNCaP | PPC-1 |
| | 8a | Ph | >100 | >100 | >20 | >20 | >20 | >20 |
| | 8b | 4-MeO-Ph | >100 | >100 | >20 | >20 | >20 | >20 |
| | 8c | 3-MeO-Ph | >100 | >100 | >20 | >20 | >20 | >20 |
| | 8d | 2-MeO-Ph | 59.4 ± 21.2 | 70.3 ± 32.5 | >20 | >20 | >20 | >20 |
| | 8e | 3,4-diMeO-Ph | >100 | >100 | >20 | >20 | >20 | >20 |
| | 8f | 3,4,5-triMeO-Ph | 0.055 ± 0.005 | 0.028 ± 0.005 | 0.071 ± 0.004 | 0.021 ± 0.001 | 0.028 ± 0.004 | 0.043 ± 0.005 |
| | 8g | 3,5-diMeO-Ph | 0.350 ± 0.2 | 0.170 ± 0.1 | 0.424 ± 0.098 | 0.301 ± 0.030 | 0.323 ± 0.041 | 0.242 ± 0.014 |
| | 8h | 2-Fluoro-Ph | >100 | >100 | >20 | >20 | >20 | >20 |
| | 8j | Hexadecyl[a] | 18.6 ± 17.5 | 16.0 ± 15.2 | >20 | >20 | >20 | >20 |

[a]Compound 8j has a lipid chain at "C" ring position.

TABLE 4

In Vitro Growth Inhibitory Effects of Compounds 8f, 8k-8q, 8t-v, 8x-z, and 10 with different "A" Rings against the Proliferation of Melanoma (A 375, B16-F1) and Prostate Cancer Cells (DU145, PC-3, LNCaP, PPC-1)

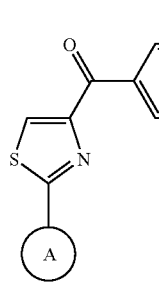

| Compounds 8 | | A-Ring | IC$_{50}$ ± SEM (nM) | | | | | |
|---|---|---|---|---|---|---|---|---|
| | | | B16-F1 | A375 | DU 145 | PC-3 | LNCaP | PPC-1 |
| | 8f | Ph | 55 ± 5 | 28 ± 5 | 71 ± 4 | 21 ± 1 | 28 ± 4 | 43 ± 5 |
| | 8k | 4-Methyl-Ph | 21 ± 10 | 11 ± 5 | 7 ± 1 | 5 ± 1 | 6 ± 1 | 6 ± 1 |
| | 8l | 2-Fluoro-Ph | 27 ± 11 | 30 ± 9 | 114 ± 3 | 82 ± 9 | 53 ± 4 | 52 ± 3 |
| | 8m | 3-Fluoro-Ph | 287 ± 36 | 304 ± 25 | 35 ± 3 | 24 ± 2 | 11 ± 2 | 21 ± 1 |
| | 8n | 4-Fluoro-Ph | 43 ± 21 | 33 ± 14 | 12 ± 1 | 13 ± 1 | 6 ± 1 | 8 ± 1 |
| | 8o | 3,4-diMeO-Ph | 161 ± 29 | 34 ± 10 | 102 ± 2 | 69 ± 3 | 38 ± 6 | 56 ± 2 |
| | 8p | 4-Nitro-Ph | 56 ± 12 | 38 ± 9 | 95 ± 5 | 56 ± 1 | 39 ± 4 | 34 ± 1 |
| | 8q | 4-Cyano-Ph | 53 ± 16 | 59 ± 24 | 52 ± 2 | 30 ± 7 | 15 ± 4 | 19 ± 2 |
| | 8t | 4-Trifluoromethyl-Ph | 92 ± 16 | 23 ± 5 | 50 ± 5 | 58 ± 4 | 94 ± 1 | 76 ± 1 |
| | 8u | 4-Bromo-Ph | 32 ± 5 | 13 ± 2 | 21 ± 4 | 18 ± 3 | 44 ± 3 | 21 ± 5 |
| | 8v | 4-Ethyl-Ph | 70 ± 8 | 17 ± 2 | 31 ± 4 | 27 ± 4 | 60 ± 5 | 22 ± 3 |
| | 8x | 4-Pyridine | >100000 | >100000 | >20000 | >20000 | >20000 | >20000 |
| | 8y | 2-Pyrimidine | 2300 ± 860 | 4100 ± 740 | 2813 ± 92 | 2657 ± 40 | 2370 ± 85 | 1186 ± 22 |
| | 8z | 2-Thienyl | 38 ± 15 | 20 ± 7 | 22 ± 1 | 17 ± 2 | 9 ± 1 | 13 ± 1 |
| | 10 | H[a] | >100000 | >100000 | >20000 | >20000 | >20000 | >20000 |

[a]Compound 10 has a proton at "A" ring position.

Example 5

Synthesis and In Vitro Cytotoxicity of Additional Methanone Compounds

The A ring indole of compounds 31 and 32 was synthesized using the same approach as 8f described in Scheme 3 above from 1H-indole-5-carbonitrile or 1H-indole-2-carbonitrile as starting material. Crude product was purified by column chromatography.

(2-(1H-indol-5-yl)thiazol-4-yl)(3,4,5-trimethoxyphenyl)methanone (Compound 31): Yield: 36.3%. $^1$H NMR (300 MHz, CDCl$_3$) δ 8.36 (br, 1H), 8.31 (br, 1H), 8.21 (s, 1H), 7.92-7.89 (dd, 1H), 7.83 (s, 2H), 7.47 (d, 1H), 7.29 (t, 1H), 6.64 (t, br, 1H), 3.98 (s, 3H), 3.97 (m, 6H). MS (ESI) m/z 417.1 [M+Na]$^+$, 392.9 [M−H]$^−$.

(2-(1H-indol-2-yl)thiazol-4-yl)(3,4,5-trimethoxyphenyl)methanone (Compound 32): Yield, 45.8%. $^1$H NMR (500 MHz, CDCl$_3$) δ 9.26 (br, 1H), 8.11 (s, 1H), 7.67 (d, 2H), 7.46 (s, 2H), 7.42 (d, 1H), 7.29 (t, 1H), 7.16 (t, 1H), 7.10 (s, 1H), 3.97 (s, 3H), 3.93 (m, 6H). MS (ESI) m/z 417.1 [M+Na]$^+$, 392.9 [M−H]$^−$ The activity of compound 31 was assessed by in vitro cytotoxicity assay as described in Example 4 above. It was determined that compound 31 exhibited enhanced activity against the PC-3, A375, and B16 cell lines.

TABLE 5

In Vitro Growth Inhibitory Effects of Compounds 31-32
Against Proliferation of Prostate and Melanoma Cancer Cells

| | | IC$_{50}$ (nM) | | | | | | |
|---|---|---|---|---|---|---|---|---|
| Compound | Structure | RH7777 | DU 145 | PC-3 | LNCaP | PPC-1 | A375 | B16 |
| 31 | 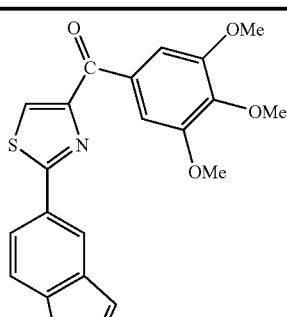 C$_{21}$H$_{18}$N$_2$O$_4$S<br>Mol Wt 394.44<br>C, 63.94, H, 4.60, N, 7.10, O, 16.22, S, 8.13 | ND | ND | 7.6 | ND | ND | 25.0 | 8.3 |
| 32 | 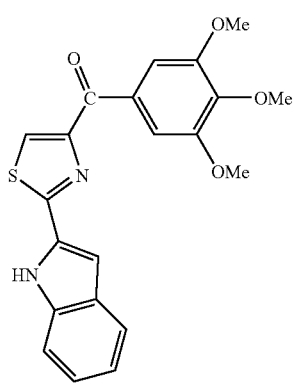 [SMILES: COc1cc(C(=O)c2csc(-c3cc4ccccc4[nH]3)n2)cc(OC)c1OC] C$_{21}$H$_{18}$N$_2$O$_4$S<br>Mol Wt 394.44<br>C, 63.94, H, 4.60, N, 7.10, O, 16.27, S, 8.13 | ND | ND | ND | ND | ND | ND | ND |

ND = not determined.

Example 6

Determining Mechanism of Action for Compound 8f

Figure 3A:
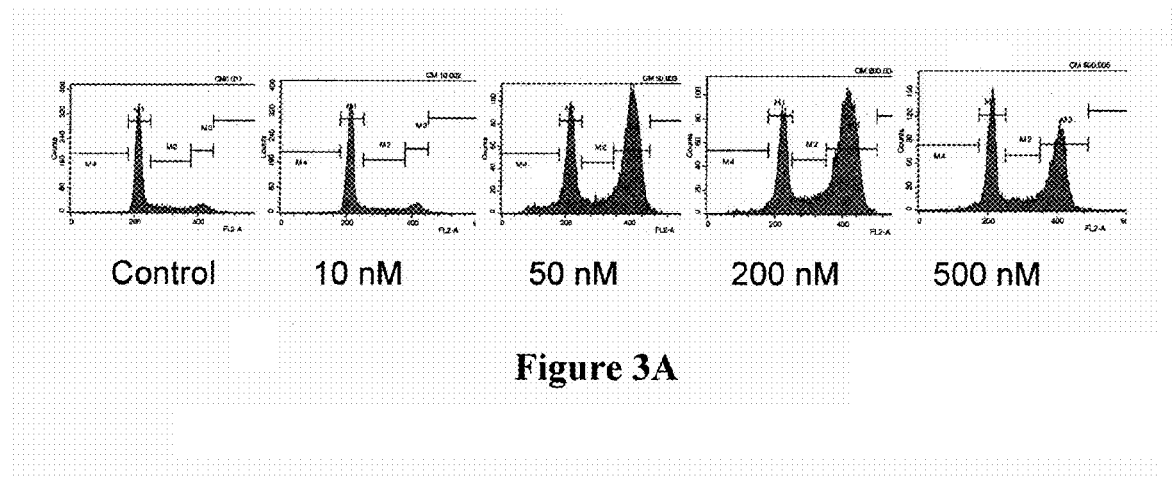
FIGS. 3A-B illustrate the effect of compound 8f on cell cycle distribution of LNCaP prostate cancer cells.
Figure 3B:
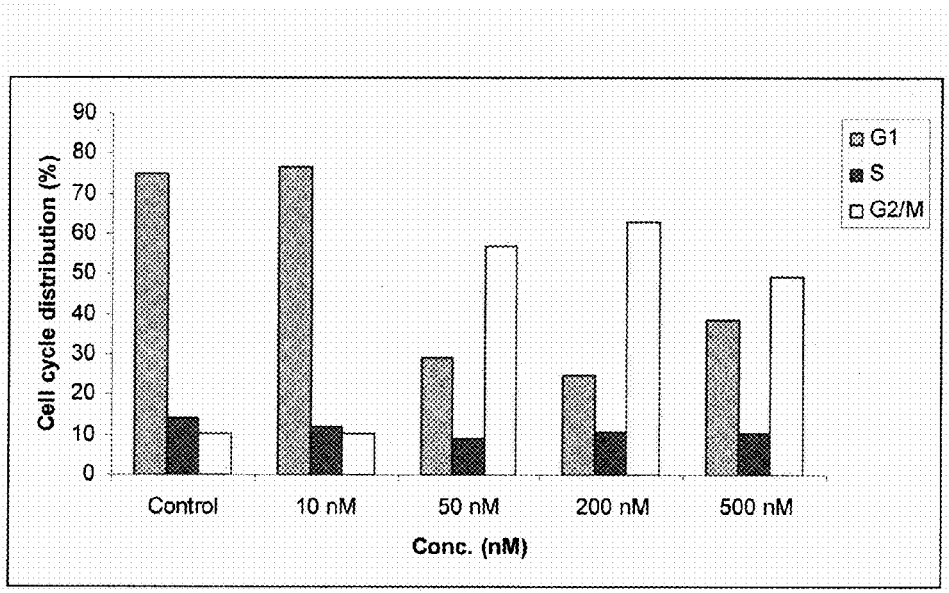

To understand the target for these highly potent compounds, cell cycle analysis was performed using compound 8f. LNCaP prostate cancer cells were exquisitely sensitive to compound 8f (IC$_{50}$=29 nM). LNCaP cells were treated with compound 8f (10 to 500 nM) for 24 h prior to staining with propidium iodide and performing cell cycle analysis. Although compound 8f had no effect on cell cycle distribution at a 10 nM (below the IC$_{50}$), the proportion of cells in G2/M phase increased in proportion to the concentration of compound 8f at higher concentrations. About 10% of untreated cells were observed in G2/M phase, whereas the cells treated with more than 50 nM showed a greater proportion of cells in G2/M phase (57, 63, and 49%, respectively, for 50, 200, and 500 nM). The results are shown in FIGS. 3A-B. The increase in G2/M phase cells was accompanied by a decrease in G1 populations, relative to control. These data indicate that compound 8f may inhibit tubulin action in a manner similar to paclitaxel, the vinca alkaloids, and cochicine (Margolis et al., "Addition of Colchicine—Tubulin Complex to Microtubule Ends: The Mechanism of Substoichiometric Colchicine Poisoning," *Proc. Nat'l Acad. Sci. USA* 74:3466-70 (1977), which is hereby incorporated by reference in its entirety).

Figure 4:
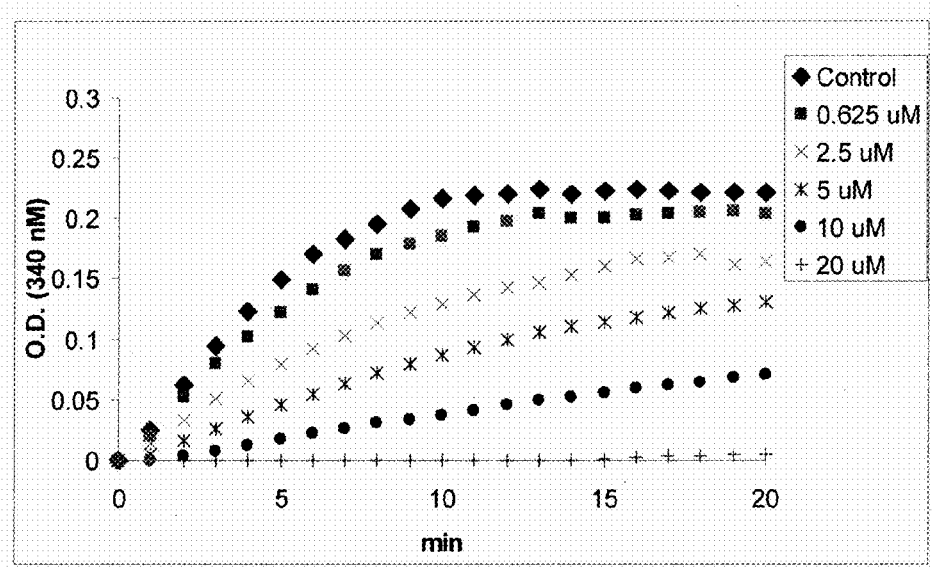
FIG. 4 is a graph illustrating the effect of compound 8f on tubulin assembly.

Based on these results, an in vitro microtubule polymerization assay was performed. Bovine brain tubulin (0.4 mg) (Cytoskeleton, Denver, Colo.) was mixed with various concentrations (0.625-20 µM) of compound 8f and incubated in 120 µl of general tubulin buffer (80 mM PIPES, 2.0 mM MgCl$_2$, 0.5 mM EGTA, pH 6.9 and 1 mM GTP). The absorbance of wavelength at 340 nm was monitored every 60 s for 20 min by the SYNERGY 4 Microplate Reader (Bio-Tek Instruments, Winooski, Vt.). The spectrophotometer was set at 37° C. for tubulin polymerization. The IC$_{50}$ value was defined as the concentration which can inhibit 50% of microtubule polymerization. The results are shown in FIG. 4. Compared with non-treated control, compound 8f inhibits tubulin polymerization. The effect of 8f on tubulin assembly was examined at concentrations from 0.625 µM to 20 µM. The observed results demonstrate that compound 8f inhibited tubulin polymerization in a dose-dependent manner with an IC$_{50}$ value of 4.23 µM.

Example 7

Figures 5A, 5B:
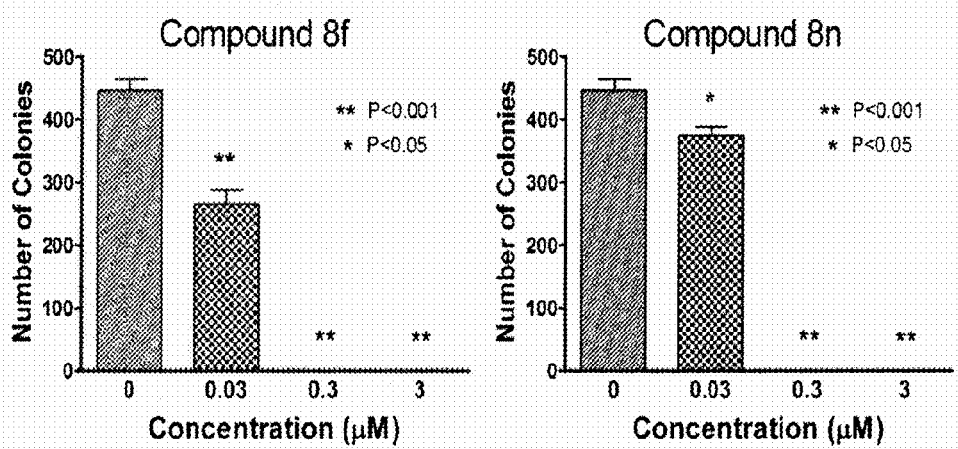
FIGS. 5A-B are graphs illustrating the ability of compounds 8f and 8n significantly to inhibit A375 melanoma colony formation in an in vitro assay. At 0.3 μM or above, colony formation is completely inhibited.

In Vitro Cytotoxicity of Compounds 8f and 8n Against A375 Melanoma Cell Line Human A375 malignant melanoma cells were plated at a colony-forming density (200 cells per well on six well plates). Cells were grown in DMEM medium (GIBCO, Invitrogen Corp., Carlsbad, Calif.) supplemented with charcoal-stripped fetal bovine serum (HyClone, Logan, Utah) and an antibiotic-antimycotic solution (Sigma, St. Louis, Mo.) at 37° C. in an atmosphere of 95% air and 5% $CO_2$. Cells were treated with compounds 8f and 8n at different concentrations (0, 0.03, 0.3, and 3 μM). Cells were grown for 10 days and colonies were fixed with 4% paraformaldehyde in PBS at 4° C. The fixed colonies were washed with distilled water, stained with 0.1% crystalline blue for 30 min and rinsed with distilled water to remove excess of the dye. Plates were photographed and colony formations were examined by eye and under the microscope. Both of compounds 8f and 8n significantly inhibit melanoma colony formation at 0.03 μM. At the two higher concentrations tested (0.3 and 3 μM), colony formations were completely inhibited, with no colonies visible under the microscope (FIGS. 5A-B).

Example 8

In Vivo Cytotoxicity of Compound 8n Against Melanoma Xenograft Tumor

Figure 6:
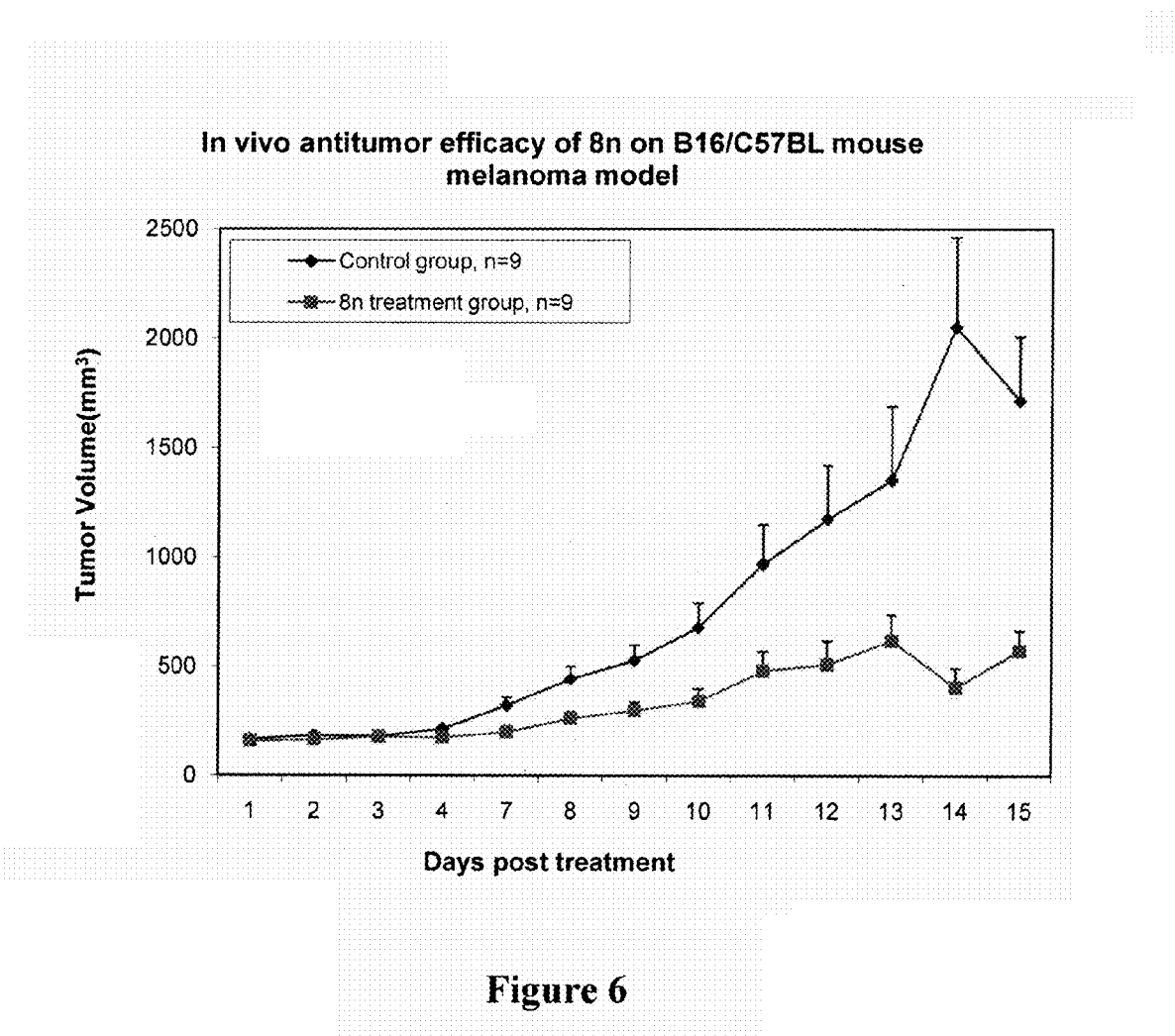
FIG. 6 is a graph illustrating the ability of compound 8n (6 mg/kg, IP daily injection) to inhibit B16 melanoma tumor growth in vivo.

The efficacy of compound 8n was assessed using B16-F1 mouse melanoma cells injected in C57 black mice. B16 tumors will grow in a fully immunocompetent host, in which case the tumor progression may more accurately replicate melanoma growth. Logarithmic growth phase B16-F1 (3.8× $10^5$) cells were injected s.c. into the right dorsal flank of C57BL/6 mice. When tumors were palpable, mice were randomized into a control and a treatment group (n=9). Mice were dosed by daily i.p. injection with 30 μl of vehicle (control group) or 8n solution (treatment group, 6 mg/kg). Tumor volume was measured once daily with a Traceable® electronic digital caliper and calculated by using the formula a×$b^2$×0.5, where a and b represented the larger and smaller diameters, respectively. Body weights were also recorded. Tumor volume was expressed as cubic millimeters. Data were expressed as Mean±SE for each group and plotted as a function of time. At the end of treatment, all mice were euthanized by $CO_2$ inhalation followed by cervical dislocation. Compound 8n showed significant tumor growth inhibition at this relatively low dose (6 mg/kg) as shown in FIG. 6. There was no significant body weight loss (<5%), and all mice had normal activities during the experiments.

Example 9

Synthesis of Compound 8f Derivatives with Hydrazine or Oxime

Carbonyl group linkers were modified into oxime and hydrazine linkers (compounds 33-36) as illustrated in Scheme 4. Compound 8f was used as starting material.

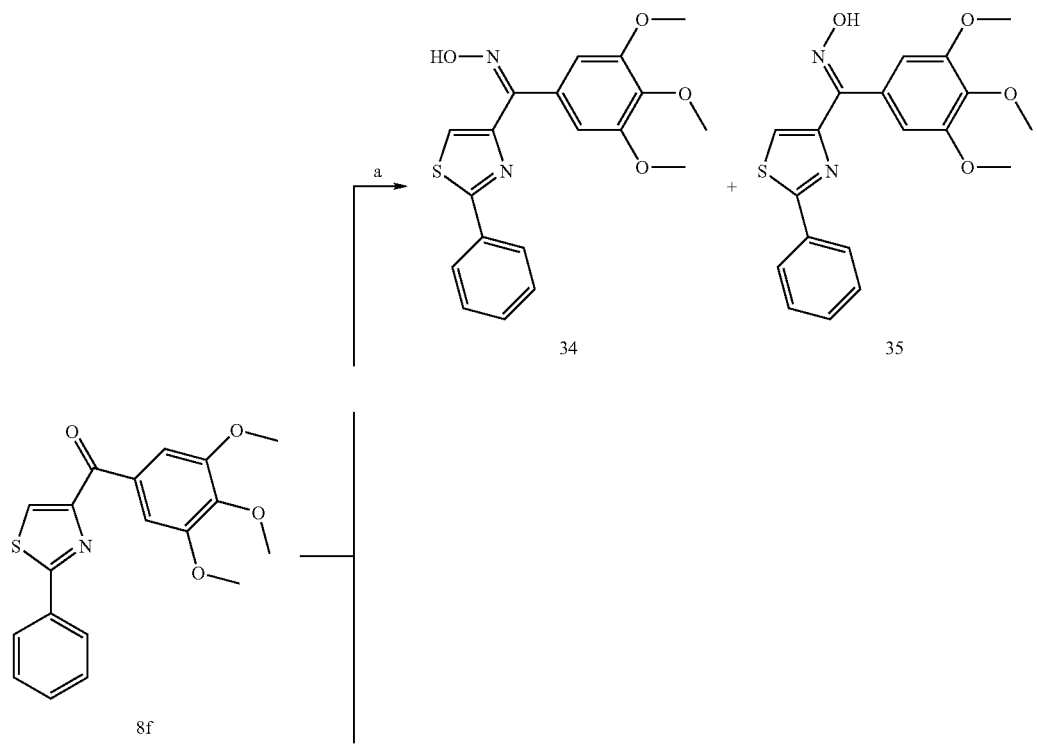

-continued

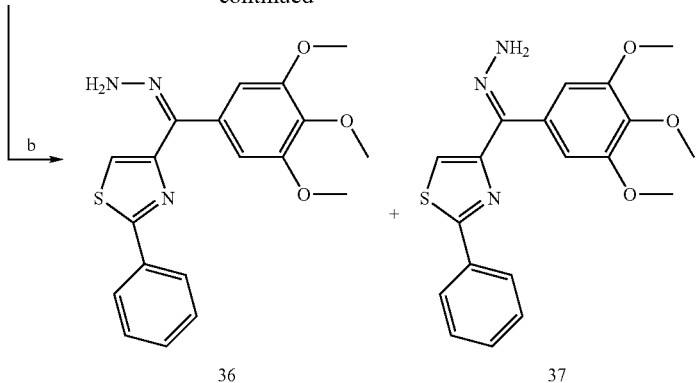

Reagents (a) NH₂OH. HCl, C₂H₅OH, H₂O, NaOH, 51%; (b) NH₂NH₂xH₂O, CH₁₂Cl₂, C₂H₅OH, 57%.

To a suspension of 50 mg 8f in 2 mL ethyl alcohol was added a 0.5 mL aqueous solution of 34 mg hydroxylamine hydrochloride. Then 13 mg sodium hydroxide in 0.5 mL H₂O was added and stirred at room temperature for 10 min. Then heating to 60° C. and stirred for 3 h. Oxime isomers 33 and 34 were separated from the reaction mixtures by flash chromatograph as white crystals with a 50% overall yield.

(Z)-(2-phenylthiazol-4-yl)(3,4,5-trimethoxyphenyl) methanone oxime (compound 33): M.p 150-153° C. ¹H NMR (300 MHz, CDCl₃) δ 11.94 (br, 1H), 8.35 (br, 1H), 7.91-7.89 (m, 2H), 7.81-7.75 (d, 1H), 7.50-7.49 (m, 3H), 6.85 (s, 2H), 3.73 (s, 6H), 3.71 (s, 3H). MS (ESI) m/z 393.3 [M+Na]⁺, 368.9 [M−H]⁻.

(E)-(2-phenylthiazol-4-yl)(3,4,5-trimethoxyphenyl) methanone oxime (compound 34): M.p 176-177° C. ¹H NMR (500 MHz, DMSO-d₆) δ 11.48 (br, 1H), 7.92-7.90 (m, 2H), 7.64 (br, 1H), 7.52-7.48 (d, TH), 7.52-7.48 (m, 3H), 6.75 (s, 2H), 3.75 (s, 6H), 3.72 (s, 3H). MS (ESI) m/z 393.1 [M+Na]⁺, 368.9 [M−H]⁻

To a solution of 2 mL hydrazine in 6 mL ethyl alcohol was added a solution of 230 mg 8f in 2 mL methylene chloride. The mixtures was refluxed overnight and absorbed on silicon gel. Hydrazone isomers 35 and 36 was separated from the flash chromatograph as white crystals with a 56.9% overall yield.

(Z)-4-(hydrazono(3,4,5-trimethoxyphenyl)methyl)-2-phenylthiazole (compound 35): M.p 117-119° C. ¹H NMR (300 MHz, CDCl₃) δ 8.01-7.98 (m, 2H), 7.49-7.46 (m, 5H), 7.33 (s, 1H), 6.82 (s, 2H), 3.87 (s, 3H), 3.85 (s, 6H). MS (ESI) m/z 370.1 [M+H]⁺.

(E)-4-(hydrazono(3,4,5-trimethoxyphenyl)methyl)-2-phenylthiazole (compound 36): M.p 65-66° C. ¹H NMR (300 MHz, CDCl₃) δ 8.04-8.00 (m, 2H), 7.44-7.40 (m, 3H), 6.95 (s, 1H), 6.62 (s, 2H), 5.62 (s, 2H), 3.93 (s, 3H), 3.87 (s, 6H). MS (ESI) m/z 370.1 [M+H]⁺.

TABLE 6

Antiproliferative effects of compounds 33-36

| Compound | | IC₅₀ (nM) | | | | | |
|---|---|---|---|---|---|---|---|
| | | B16 | A375 | Fibroblast | DU145 | PC-3 | LNCaP | PPC-1 |
| 33 | 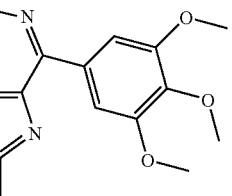 | 0.32 | 0.18 | 0.36 | 0.10 | 0.12 | 0.19 | 0.16 |
| 34 | 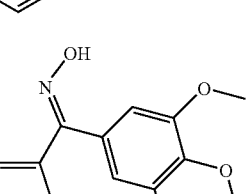 | 11.4 | 7.8 | 10.1 | >1 | >1 | >1 | >1 |

TABLE 6-continued

Antiproliferative effects of compounds 33-36

| Compound | IC$_{50}$ (nM) | | | | | | |
|---|---|---|---|---|---|---|---|
| | B16 | A375 | Fibroblast | DU145 | PC-3 | LNCaP | PPC-1 |
| 35 | 2.0 | 0.9 | 1.9 | 1.21 | 1.12 | 1.80 | 0.87 |
| 36 | 1.8 | 0.6 | 1.0 | 1.21 | 1.04 | 1.30 | 0.97 |

Example 10

Design of Additional Derivatives

Compound 8f will be further modified to thioketone analogs 41 and 42 (Scheme 5 below). Compounds 8a-z will be similarly modified. The carbonyl group can be converted into a thiocarbonyl group by the action of Lawesson's reagent (Jesberger et al., *Synthesis* 1929-1958 (2003), which is hereby incorporated by reference in its entirety). The thioketone structure with conjugated aromatic rings is stable relative to unhindered thioketones. The thiazole compound can be obtained after dehydronation. (Riedrich et al., *Angewandre Chemie, International Edition*, 46(15):2701-2703 (2007), which is hereby incorporated by reference in its entirety). This conversion will decrease the hydrogen bond acceptor ability from O—H in ketone to S—H in thione. It will be helpful to examine the importance of hydrogen acceptor position in these molecules.

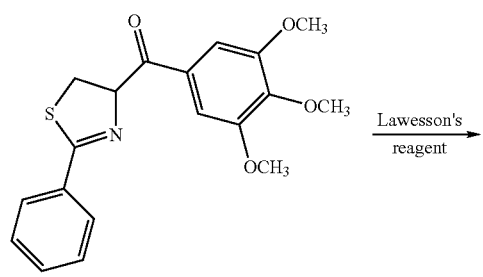

Scheme 5

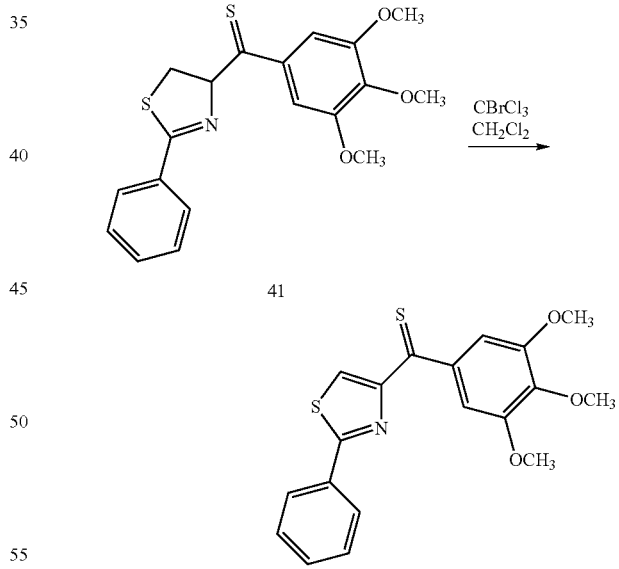

New analogs in which the carbonyl has been reduced to an alcohol (43 and 44, Scheme 6A below) or reduced to methylene (45 and 46, Scheme 6B below) will be synthesized. The alcohol 43 and 44 can be obtained using Grignard reaction of intermediate aldehyde with according Grignard reagents. Analogs 45 and 46 can be prepared with Clemmensen reduction of ketone function group to produce the corresponding hydrocarbon. When carbonyl is reduced to an alcohol or methylene, the strong hydrogen acceptor C═O reverses to strong hydrogen donor O—H or hydrocarbon, which totally loses hydrogen bond effects. This modification will provide insight as to the importance of carbonyl group and if it has a specific function in the anti-cancer activity.
Scheme 6A
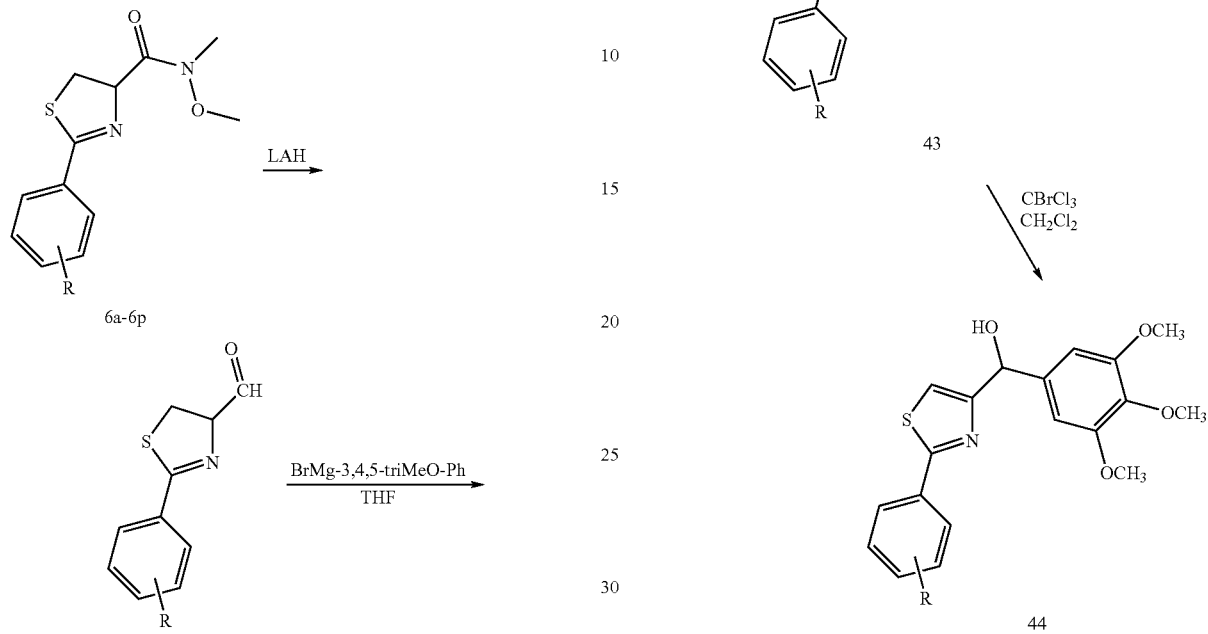
6a-6p
-continued
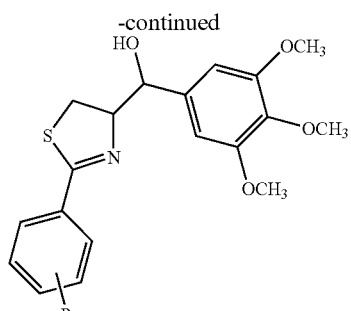
43
Scheme 6B
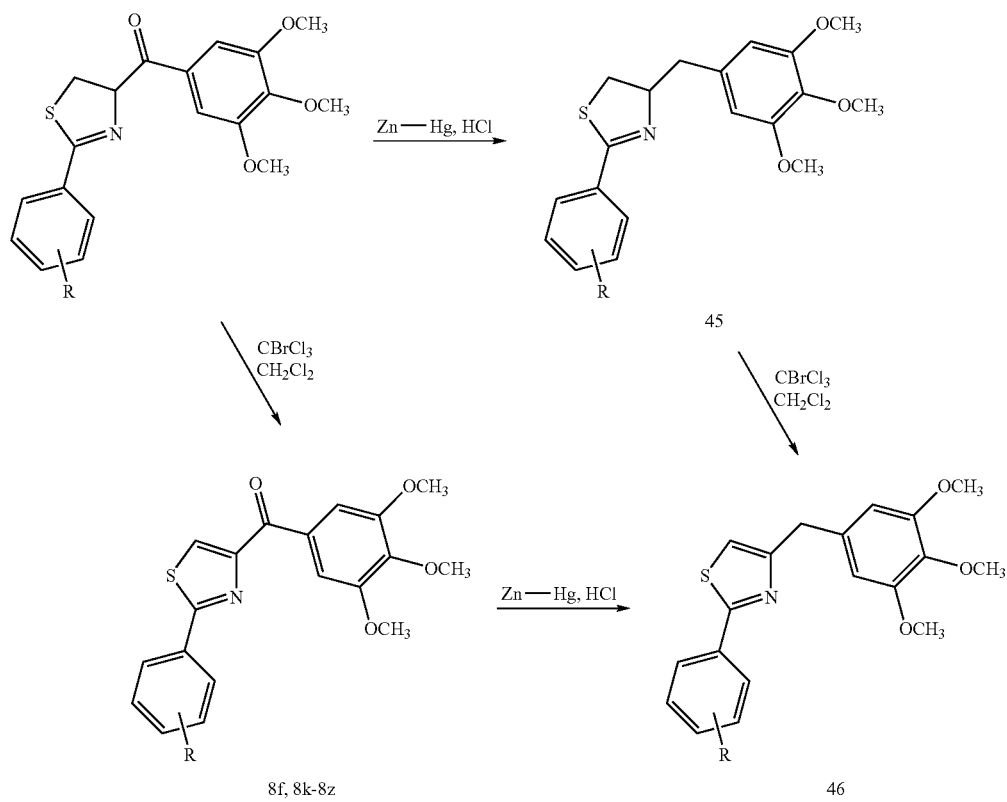
8f, 8k-8z
45
46

To examine the importance of ketone on antiproliferation in cancer cells, this linker will be converted into amide and ester analogs (47-50, Scheme 7 below). Finding activity in any of these series of analogs, the different linkages between the rings optimized to enhance activity and metabolic stability. As Scheme 7 below shows, consistent with the results demonstrated in the preceding examples, thiazoline and thiazole rings will be obtained from reaction of benzonitrile (including substituted benzonitrile) and cysteine (Bergeron et al., *J. Med. Chem.* 48:821-831 (2005), which is hereby incorporated by reference in its entirety). The resulting acid intermediates will be used to prepare the ester and amide linkages. These analogs will be compared for antiproliferation activity on prostate cancer cells and/or melanoma cells, and control cells, and compared to Compounds 8f and 8n.

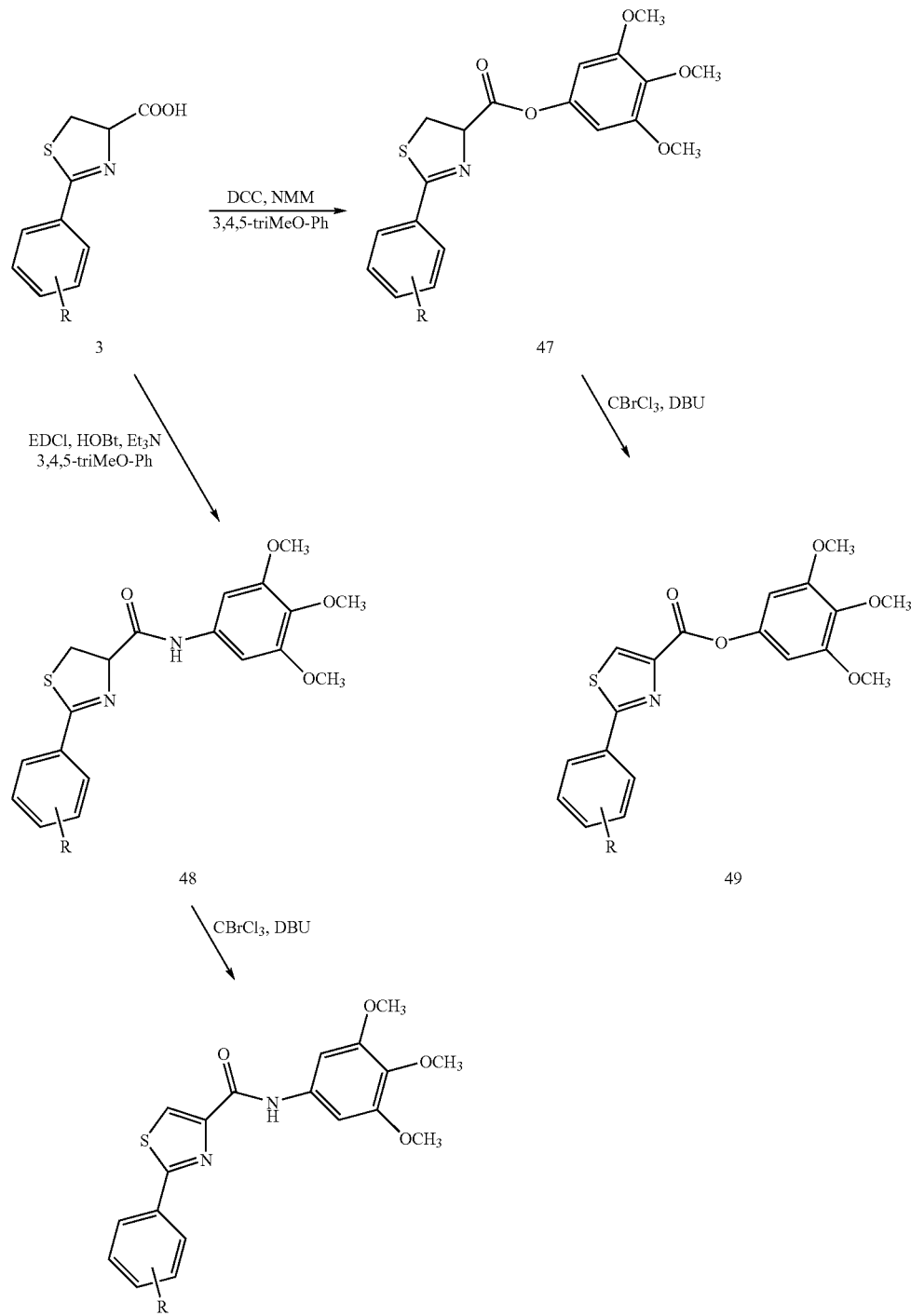

Compounds will also be prepared with the trimethoxyphenyl group replaced with different substituted aromatic rings, saturated or unsaturated alkyls and various heterocyclic groups as defined herein. This can be accomplished by using different Grignard reagents. These analogs will allow for optimization of the "C" ring with best activities, lowest toxicity, and best metabolic stability for prostate cancer, melanoma, and other cancers.

Replacement of the central thiazoline and thiazole rings with corresponding imidazoline (51), imidazole (52), oxazoline (53) and oxazole (54) ring systems will also be performed. Ethyl benzimidate hydrochloride salt reacted with 2,3-diaminopropanoic acid to give imidazoline ring system (see Scheme 8A below). (Hsu et al., *J. Med. Chem.* 23(11), 1232-1235 (1980), which is hereby incorporated by reference in its entirety). Dehydrogenation of imidazolines will afford desired imidazole compounds. Oxazolines can be prepared according to the classical condensation of phenyl imino ether with serine ester using triethylamine as a base (see Scheme 8B below) (Meyer et al., *Tetrahedron: Asymmetry* 14:2229-2238 (2003), which is hereby incorporated by reference in its entirety). Dehydrogenation of oxazolines will give the desired oxazole compounds.

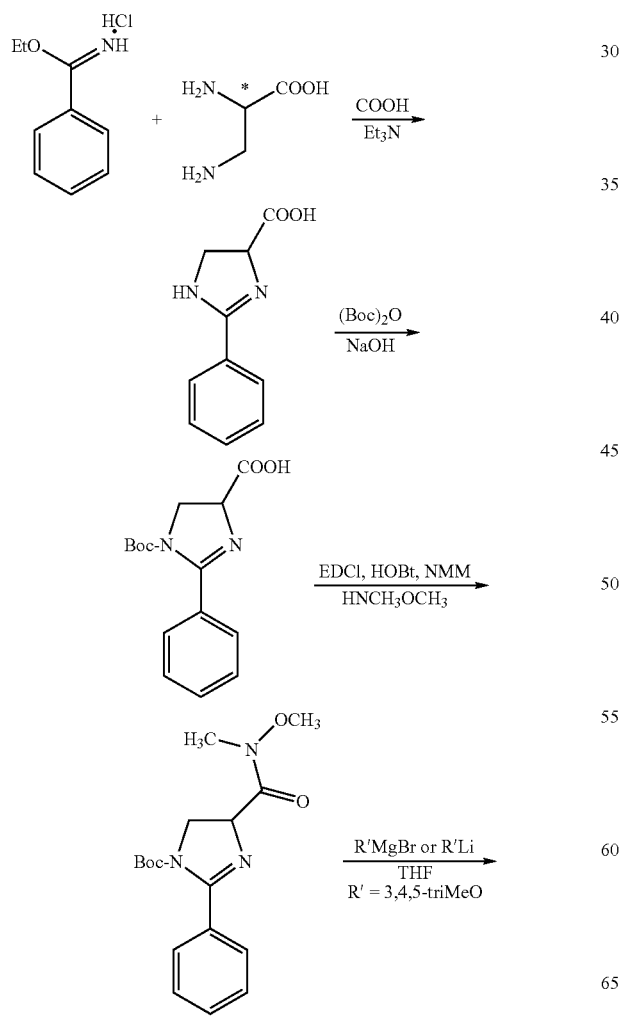

Scheme 8A

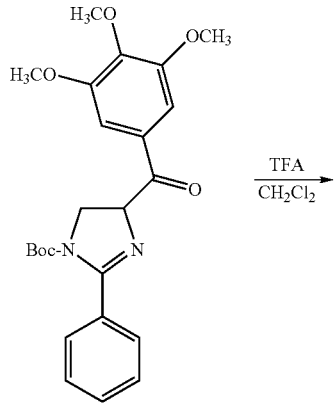

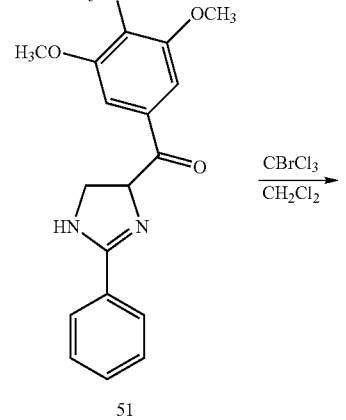

51

52

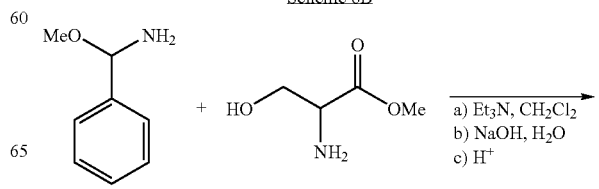

Scheme 8B

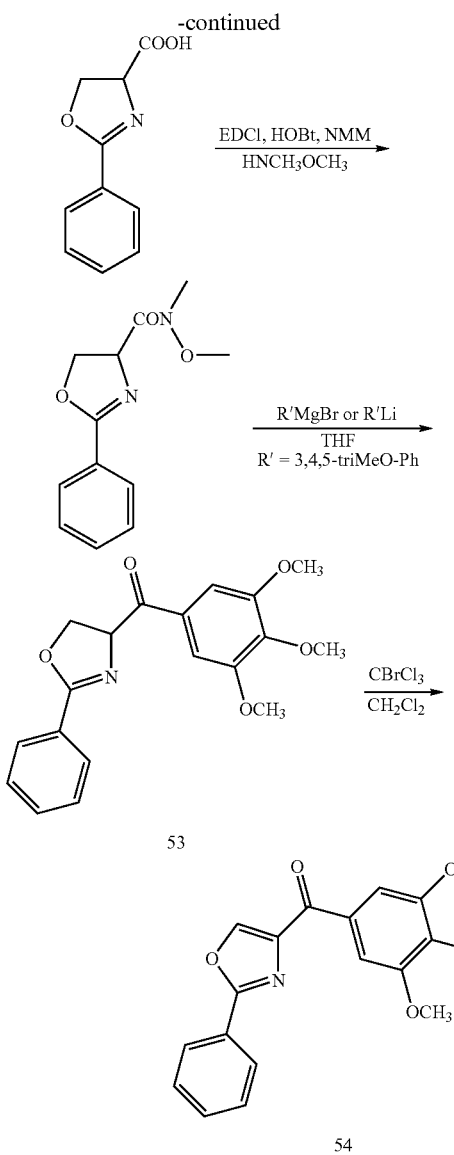

53

54

Optically pure isomers of compounds 8a-8z will also be prepared to investigate the importance of chirality at 4-position of thiazoline. This will be carried out using D- or L-Cysteine to synthesize the chiral intermediate ketones from protected D- or L-Cysteine. Condensation of the intermediate ketones with benzonitrile will afford R- or S-thiazoline isomers. Thiazoles can be prepared by dehydrogenation.

From previous studies on structure-relationship of thiazolidine carboxylic acid amides, reversed electronic effects of substituents on phenyl in C-2 position of thiazolidine ring resulted in significant different activity on prostate cancer cell lines. Derivatives with different aromatic ring substitutions from various substituted benzonitrile reactants will also be prepared (e.g., 4-dimethylamino-benzonitrile, 3-hydroxybenzonitrile, 4-methoxybenzonitrile, 3,4-dimethoxybenzonitrile, 3,4,5-trimethoxybenzonitrile, 4-acetamidobenzonitrile, 4-fluorobenzonitrile, 4-bromobenzonitrile, 4-nitrobenzonitrile, 4-cyanobenzonitrile, 3,5-difluorobenzonitrile, 4-methylbenzonitrile, 3-bromo-4-fluorobenzonitrile, 2,6-dichlorobenzonitrile, phenylbenzonitrile, indolenitrile and substituted indolylnitriles, pyridine-nitrile and substituted pyridinylnitriles, furan-nitrile and substituted furanylnitriles) to induce both electron withdrawing and electron donating substituents in ring substituent of C-2 position in thiazoline ring. It is believed that the best substituents of C-2 phenyl, indolyl, furanyl, thiophen-yl, and pyridinyl groups can be found after screening the resulting analogs.

All of the features described herein (including any accompanying claims, abstract and drawings), and/or all of the steps of any method or process so disclosed, may be combined with any of the above aspects in any combination except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A compound according to formula (I)

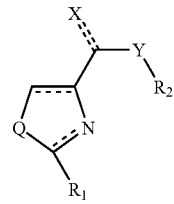

(I)

wherein,
Q is S;
X is O=, S=, =N—NH$_2$, =N—OH, or —OH;
Y is optional, and can be C$_1$ to C$_{20}$ hydrocarbon;
R$_1$ is substituted or unsubstituted furanyl, indolyl, phenyl, biphenyl, triphenyl, diphenylmethane, thiophene-yl, adamantane-yl, or fluorene-yl; wherein said substituents are selected from hydroxyl, an aliphatic straight- or branched-chain C$_1$ to C$_{10}$ hydrocarbon, aryloxy, nitro, cyano, halo, haloalkyl, dihaloalkyl, trihaloalkyl, amino, alkylamino, mesylamino, dialkylamino, arylamino, amido, urea, alkyl-urea, alkylamido, haloalkylamido, arylamido, aryl, C$_5$ to C$_7$ cycloalkyl and arylalkyl, and combinations thereof; and
R$_2$ is substituted or unsubstituted furanyl, indolyl, pyridinyl, phenyl, biphenyl, triphenyl, diphenylmethane, thiophene-yl, adamantane-yl, or fluorene-yl; wherein said substituents are selected from hydroxyl, an aliphatic straight- or branched-chain C$_1$ to C$_{10}$ hydrocarbon, alkoxy, aryloxy, nitro, cyano, halo, haloalkyl, dihaloalkyl, trihaloalkyl, alkylamino, mesylamino, dialkylamino, arylamino, amido, urea, alkyl-urea, alkylamido, haloalkylamido, arylamido, C$_5$ to C$_7$ cycloalkyl and arylalkyl, and combinations thereof; or
a pharmaceutically acceptable salt, or prodrug thereof.
2. The compound of claim 1, wherein formula (I) is

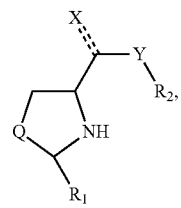

(Ia)

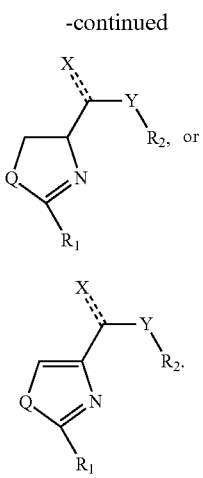

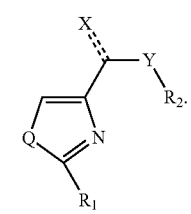

3. The compound of claim 1, wherein $R_1$ and $R_2$ are each a substituted or unsubstituted phenyl.

4. The compound of claim 1, wherein X is O=.
5. The compound of claim 1, wherein X is S=.
6. The compound of claim 1, wherein X is OH.
7. The compound of claim 1, wherein X is =N—NH$_2$.
8. The compound of claim 1, wherein X is =N—OH.
9. The compound of claim 1, wherein Y is absent, and $R_2$ is bound directly to —C(X)—.
10. The compound of claim 1, wherein $R_2$ is 3,4,5-trimethoxyphenyl.
11. The compound of claim 10, wherein $R_1$ is a substituted or unsubstituted phenyl, substituted or unsubstituted thiophene-yl, or substituted or unsubstituted indolyl.
12. The compound of claim 11, wherein $R_1$ is phenyl, thiophene-yl, or indolyl substituted with one or more substituents selected from the group of methyl, ethyl, fluoro, bromo, cyano, nitro, trifluoromethyl, and amino.
13. The compound of claim 1, wherein the compound is selected from the group of:
  (3,4,5-trimethoxyphenyl)(2-phenylthiazol-4-yl)methanone;
  (2-p-tolylthiazol-4-yl)(3,4,5-trimethoxyphenyl)methanone;
  (2-(4-fluorophenyl)-thiazol-4-yl)(3,4,5-trimethoxyphenyl)methanone;
  (2-(4-nitrophenyl)-thiazol-4-yl)(3,4,5-trimethoxyphenyl)methanone;
  (2-(4-cyanophenyl)-thiazol-4-yl)(3,4,5-trimethoxyphenyl)methanone;
  (2-(4-(trifluoromethyl)-phenyl)-thiazol-4-yl)(3,4,5-trimethoxyphenyl)methanone;
  (2-(4-bromophenyl)-thiazol-4-yl)-(3,4,5-trimethoxyphenyl)methanone;
  (2-(4-ethylphenyl)-thiazol-4-yl)-(3,4,5-trimethoxy-phenyl)methanone;
  (2-(4-aminophenyl)-thiazol-4-yl)-(3,4,5-trimethoxy-phenyl)methanone;
  (2-(thiophen-2-yl)-thiazol-4-yl)-(3,4,5-trimethoxyphenyl)methanone;
  (2-(1H-indol-5-yl)thiazol-4-yl)(3,4,5-trimethoxyphenyl)methanone;
  (2-(1H-indol-2-yl)thiazol-4-yl)(3,4,5-trimethoxyphenyl)methanone;
  (2-(1H-indol-1-yl)thiazol-4-yl)(3,4,5-trimethoxyphenyl)methanone;
  (2-(1H-indol-3-yl)thiazol-4-yl)(3,4,5-trimethoxyphenyl)methanone;
  (2-(1H-indol-4-yl)thiazol-4-yl)(3,4,5-trimethoxyphenyl)methanone;
  (2-(1H-indol-6-yl)thiazol-4-yl)(3,4,5-trimethoxyphenyl)methanone; and
  (2-(1H-indol-7-yl)thiazol-4-yl)(3,4,5-trimethoxyphenyl)methanone.

14. A pharmaceutical composition comprising a compound according to claim 1 and a pharmaceutically acceptable carrier.

15. A method of treating cancer comprising:
  administering a compound according to claim 1 to a subject having cancer under conditions effective to treat the cancer.

16. The method of claim 15, wherein the cancer is selected from the group consisting of prostate cancer, breast cancer, ovarian cancer, skin cancer, lung cancer, colon cancer, leukemia, renal cancer, CNS cancer, and combinations thereof.

17. The method according to claim 15, wherein said administering is carried out systemically.

18. The method according to claim 15, wherein said administering is carried out directly to a site where cancer cells are present.

19. The method according to claim 15, wherein said administering is carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes.

20. The method according to claim 15, wherein the compound is administered at a dosage rate of about 0.01 to about 100 mg/kg·body weight.

21. The method according to claim 15, wherein said administering is repeated periodically.

22. The method according to claim 15, wherein said administering is carried out in combination with another cancer therapy.

23. A method of destroying a cancerous cell comprising:
  providing a compound according to claim 1; and
  contacting the cancerous cell with the compound under conditions effective to kill the cancer cell.

24. A method of making a compound according to claim 1 comprising:
  reacting intermediate

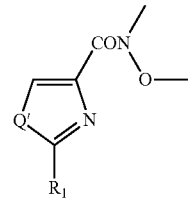

with either a Grignard reagent containing $R_2$ or Br—$R_2$ under conditions effective to form a compound according to formula (I) having a methanone linker group, where $R_1$ and $R_2$ are defined as in claim 1 and Q' is the same as Q.

25. The method according to claim 24 further comprising:
  reacting the compound having a methanone linker group with hydroxylamine hydrochloride under conditions effective to form a compound of formula (I) having a methanone oxime linker group.

26. The method according to claim 24 further comprising:
  reacting the compound having a methanone linker group with hydrazine under conditions effective to form a compound of formula (I) having a hydrazono linker group.

27. The method according to claim 24 further comprising: reacting the compound having a methanone linker group with Zn—Hg under acid conditions to form a compound of formula (I) having a methylene linker group.

28. The method according to claim 24 further comprising: forming the intermediate by dehydrogenation of a precursor

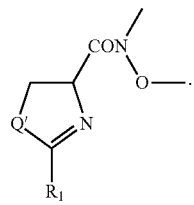

29. A method of making a compound according to claim 1 comprising
reacting intermediate

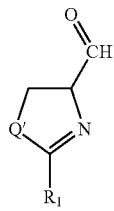

with a Grignard reagent containing $R_2$ under conditions effective to form a compound according to formula (I) having a —CH(OH)— linker group, where $R_1$ and $R_2$ are defined as in claim 1 and Q' is the same as Q.

30. The method according to claim 29 further comprising: dehydrogenating the resulting compound of formula (I) to form a thiazole, ring.

31. A method of making a compound according to claim 1 comprising:
reacting an intermediate

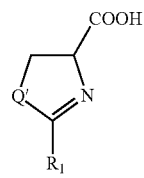

with Br—$R_2$ under conditions effective to form a compound according to formula (I) having an ester or amide linker group, where $R_1$ and $R_2$ are defined as in claim 1 and Q' is the same as Q.

32. The method according to claim 31 further comprising:
dehydrogenating the resulting compound of formula (I) to form a thiazole ring.

* * * * *